US 6,679,833 B2
(12) United States Patent
Smith et al.

(10) Patent No.: US 6,679,833 B2
(45) Date of Patent: Jan. 20, 2004

(54) DEVICES AND METHODS FOR PERCUTANEOUS SURGERY

(75) Inventors: Maurice M. Smith, Cordova, TN (US); Kevin T. Foley, Germantown, TN (US); Thomas E. Roehm III, Braden, TN (US); William Barry Null, Olive Branch, MS (US)

(73) Assignee: SDGI Holdings, Inc., Wilmington, DE (US)

( * ) Notice: Subject to any disclaimer, the term of this patent is extended or adjusted under 35 U.S.C. 154(b) by 163 days.

(21) Appl. No.: 09/815,693

(22) Filed: Mar. 23, 2001

(65) Prior Publication Data

US 2002/0022764 A1 Feb. 21, 2002

Related U.S. Application Data

(63) Continuation-in-part of application No. PCT/US99/21866, filed on Sep. 21, 1999, and a continuation-in-part of application No. 09/233,879, filed on Jan. 20, 1999, now Pat. No. 6,217,509, which is a division of application No. 08/736,626, filed on Oct. 24, 1996, now Pat. No. 5,902,231, which is a continuation-in-part of application No. 08/620,933, filed on Mar. 22, 1996, now Pat. No. 5,792,044.

(51) Int. Cl.[7] .............................. A61B 1/00; A61B 1/313
(52) U.S. Cl. ....................................... 600/114; 600/102
(58) Field of Search ................................ 600/101, 102, 600/114, 125, 136; 604/164, 167, 264, 283

(56) References Cited

U.S. PATENT DOCUMENTS

| 2,235,979 A | 3/1941 | Brown | |
|---|---|---|---|
| 3,486,505 A | 12/1969 | Morrison | |
| 3,941,127 A | 3/1976 | Froning | 128/215 |
| 3,964,480 A | 6/1976 | Froning | 128/215 |
| 4,461,281 A | 7/1984 | Carson | 128/3 |
| 4,498,902 A | 2/1985 | Ash et al. | 604/164 |

(List continued on next page.)

FOREIGN PATENT DOCUMENTS

| DE | 1 566 116 | 1/1970 |
|---|---|---|
| DE | 31 08 766 A1 | 9/1982 |
| DE | 3936811 A1 | 9/1990 |
| DE | 299 16 026 U1 | 11/1999 |
| DK | 1012010 | 11/2000 |
| EP | 0 303 824 A2 | 2/1989 |
| EP | 0 528 562 A2 | 7/1992 |
| FR | 2 701 379 A1 | 8/1994 |
| FR | 2 714 285 | 6/1995 |
| GB | 2 234 906 A | 2/1991 |
| WO | WO92/19146 | 11/1992 |
| WO | WO 93/14801 | 8/1993 |
| WO | WO 93/15647 | 8/1993 |
| WO | WO 95/22285 | 8/1995 |
| WO | WO 00 18306 A | 4/2000 |
| WO | WO 01 54560 | 8/2001 |

OTHER PUBLICATIONS

*Metrx System*™ *MicroEndoscopic Discectomy Surgical Technique*, Medtronic Sofamor Danek, 1999.

*Primary Examiner*—John P. Leubecker
(74) *Attorney, Agent, or Firm*—Woodard, Emhardt, Moriarty, McNett & Henry LLP

(57) ABSTRACT

Methods and devices for performing surgery in a patient are provided. A cannula provides a working channel for access to a location in the patient. A clamp assembly is removably engaged to the cannula. The clamp assembly allows use of an endoscopic viewing system or can be removed to allow use of a microscopic viewing system in order to view the surgical site in the patient through the working channel. The clamp assembly includes a viewing element mounting portion having a length along which an endoscopic viewing element can be selectively positioned.

34 Claims, 29 Drawing Sheets

U.S. PATENT DOCUMENTS

| | | |
|---|---|---|
| 4,538,594 A | 9/1985 | Boebel et al. |
| 4,545,374 A | 10/1985 | Jacobson .................... 128/303 |
| 4,573,448 A | 3/1986 | Kambin ........................ 128/1 |
| 4,586,491 A | 5/1986 | Carpenter ...................... 128/4 |
| 4,638,799 A | 1/1987 | Moore ........................ 128/303 |
| 4,655,216 A | 4/1987 | Tischer ....................... 128/303 |
| 4,674,501 A | 6/1987 | Greenberg .................. 128/305 |
| 4,678,459 A | 7/1987 | Onik et al. .................... 604/22 |
| 4,696,544 A * | 9/1987 | Costella .................. 356/241.1 |
| 4,700,694 A | 10/1987 | Shishido ........................ 128/6 |
| 4,736,738 A | 4/1988 | Lipovsek et al. ............. 128/92 |
| 4,750,475 A | 6/1988 | Yoshihashi ..................... 128/6 |
| 4,750,487 A | 6/1988 | Zanetti ....................... 128/303 |
| 4,762,120 A | 8/1988 | Hussein ......................... 128/6 |
| 4,875,897 A | 10/1989 | Lee ............................ 604/283 |
| 4,899,729 A | 2/1990 | Gill et al. ....................... 128/3 |
| 4,905,082 A | 2/1990 | Nishigaki et al. ........... 358/898 |
| 4,972,827 A | 11/1990 | Kishi et al. ..................... 128/3 |
| 5,004,457 A | 4/1991 | Wyatt et al. ................. 604/158 |
| 5,071,410 A | 12/1991 | Pazell ......................... 604/164 |
| 5,125,396 A | 6/1992 | Ray ............................. 128/20 |
| 5,158,543 A | 10/1992 | Lazarus ...................... 604/164 |
| 5,171,279 A | 12/1992 | Mathews ...................... 623/17 |
| 5,195,541 A | 3/1993 | Obenchain .................. 128/898 |
| 5,201,729 A | 4/1993 | Hertzmann et al. ............ 606/2 |
| 5,242,444 A | 9/1993 | MacMillan .................. 606/61 |
| 5,334,150 A | 8/1994 | Kaali .......................... 604/164 |
| 5,354,302 A | 10/1994 | Ko ................................ 606/61 |
| 5,357,983 A | 10/1994 | Mathews .................... 128/898 |
| 5,376,076 A | 12/1994 | Kaali .......................... 604/164 |
| 5,380,291 A | 1/1995 | Kaali .......................... 604/164 |
| 5,392,766 A | 2/1995 | Masterson et al. ............. 128/4 |
| 5,395,317 A | 3/1995 | Kambin ....................... 604/51 |
| 5,396,880 A | 3/1995 | Kagan et al. ................... 128/6 |
| 5,437,637 A | 8/1995 | Lieber et al. ................. 604/96 |
| 5,439,449 A | 8/1995 | Mapes et al. ............... 604/164 |
| 5,439,464 A | 8/1995 | Shapiro ....................... 606/83 |
| 5,441,041 A | 8/1995 | Sauer et al. ................. 600/106 |
| 5,445,142 A | 8/1995 | Hassler, Jr. ................. 600/105 |
| 5,472,426 A | 12/1995 | Bonati et al. ................ 604/164 |
| 5,512,034 A | 4/1996 | Finn et al. ................... 600/138 |
| 5,520,607 A * | 5/1996 | Frassica et al. ................ 248/56 |
| 5,534,009 A | 7/1996 | Lander ....................... 606/185 |
| 5,551,947 A | 9/1996 | Kaali .......................... 604/264 |
| 5,556,371 A * | 9/1996 | Schulken et al. ........... 600/105 |
| 5,562,696 A | 10/1996 | Nobles et al. .............. 606/185 |
| 5,569,205 A | 10/1996 | Hart et al. ................... 604/167 |
| 5,588,949 A * | 12/1996 | Taylor et al. ................ 600/101 |
| 5,667,472 A | 9/1997 | Finn et al. ................... 600/104 |
| 5,667,473 A | 9/1997 | Finn et al. ................... 600/104 |
| 5,667,478 A | 9/1997 | McFarlin et al. ........... 600/182 |
| 5,735,792 A | 4/1998 | Vanden Hoek et al. ...... 600/138 |
| 5,772,661 A | 6/1998 | Michelson ................... 606/61 |
| 5,921,917 A * | 7/1999 | Barthel et al. .......... 128/200.26 |
| 5,928,137 A * | 7/1999 | Green ......................... 600/104 |
| 5,954,635 A | 9/1999 | Foley et al. ................. 600/114 |
| 5,997,471 A * | 12/1999 | Gumb et al. ................. 600/102 |
| 6,142,931 A * | 11/2000 | Kaji ............................ 600/102 |
| 6,152,871 A | 11/2000 | Foley et al. ................. 600/114 |
| 6,258,024 B1 * | 7/2001 | van Der Weegen ......... 600/114 |
| 6,361,488 B1 * | 3/2002 | Davison et al. ............. 600/102 |

\* cited by examiner

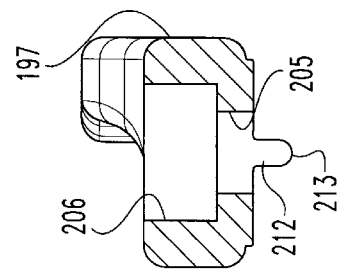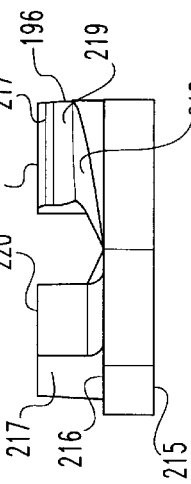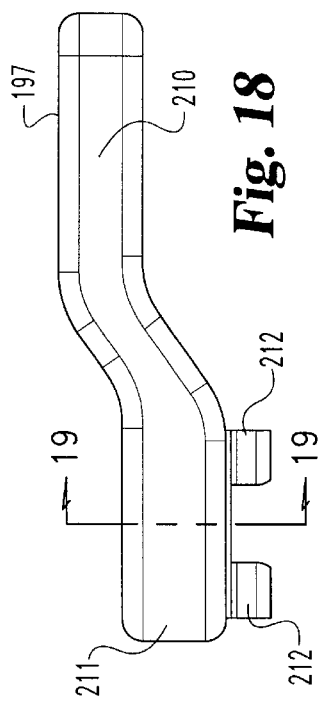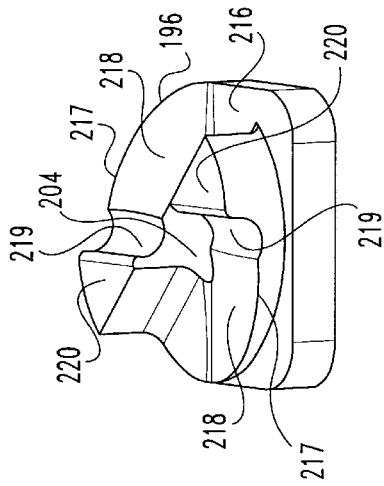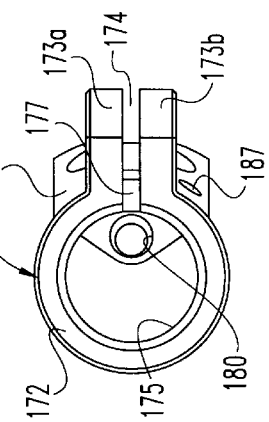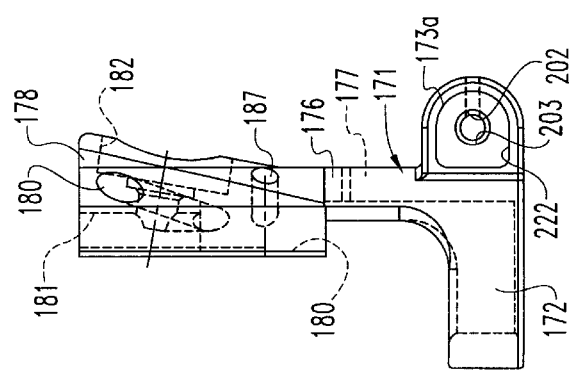

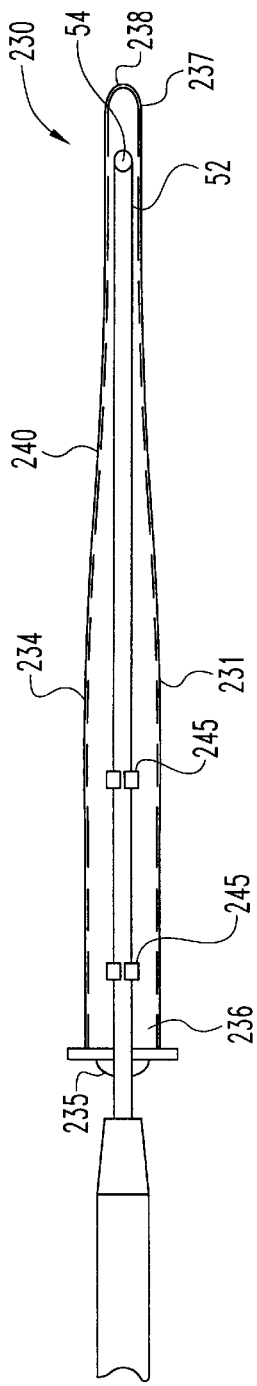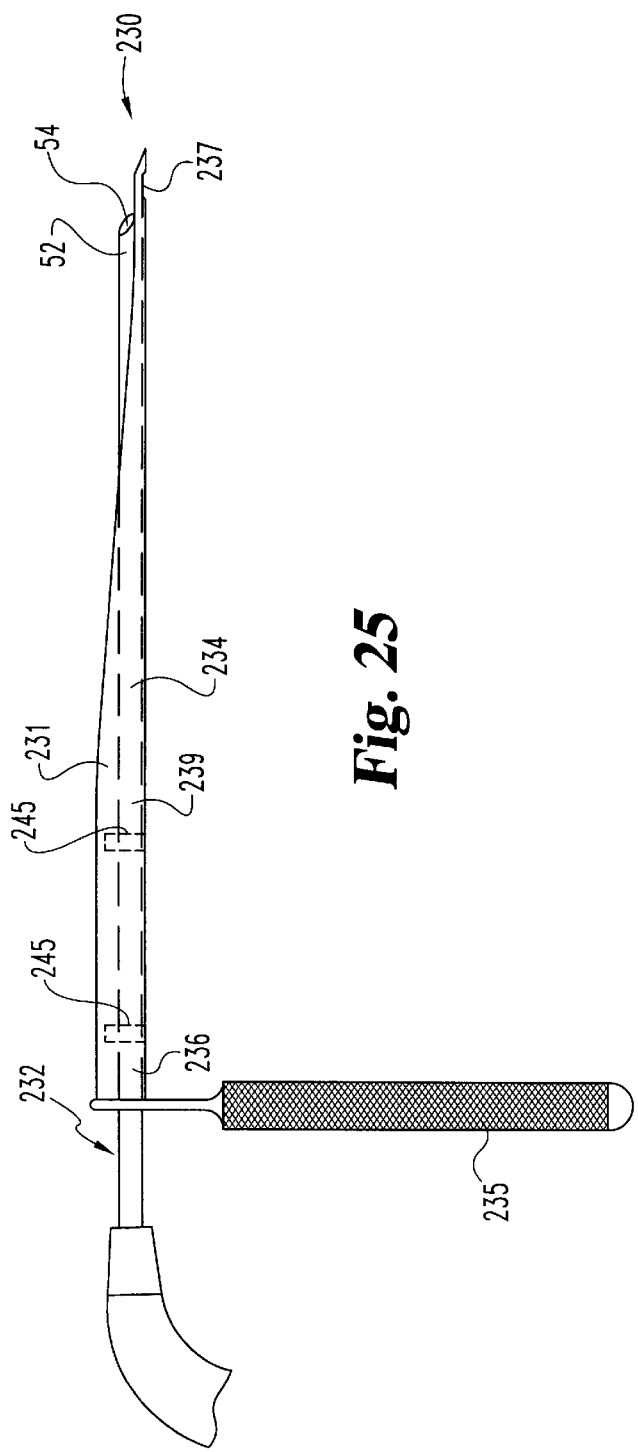

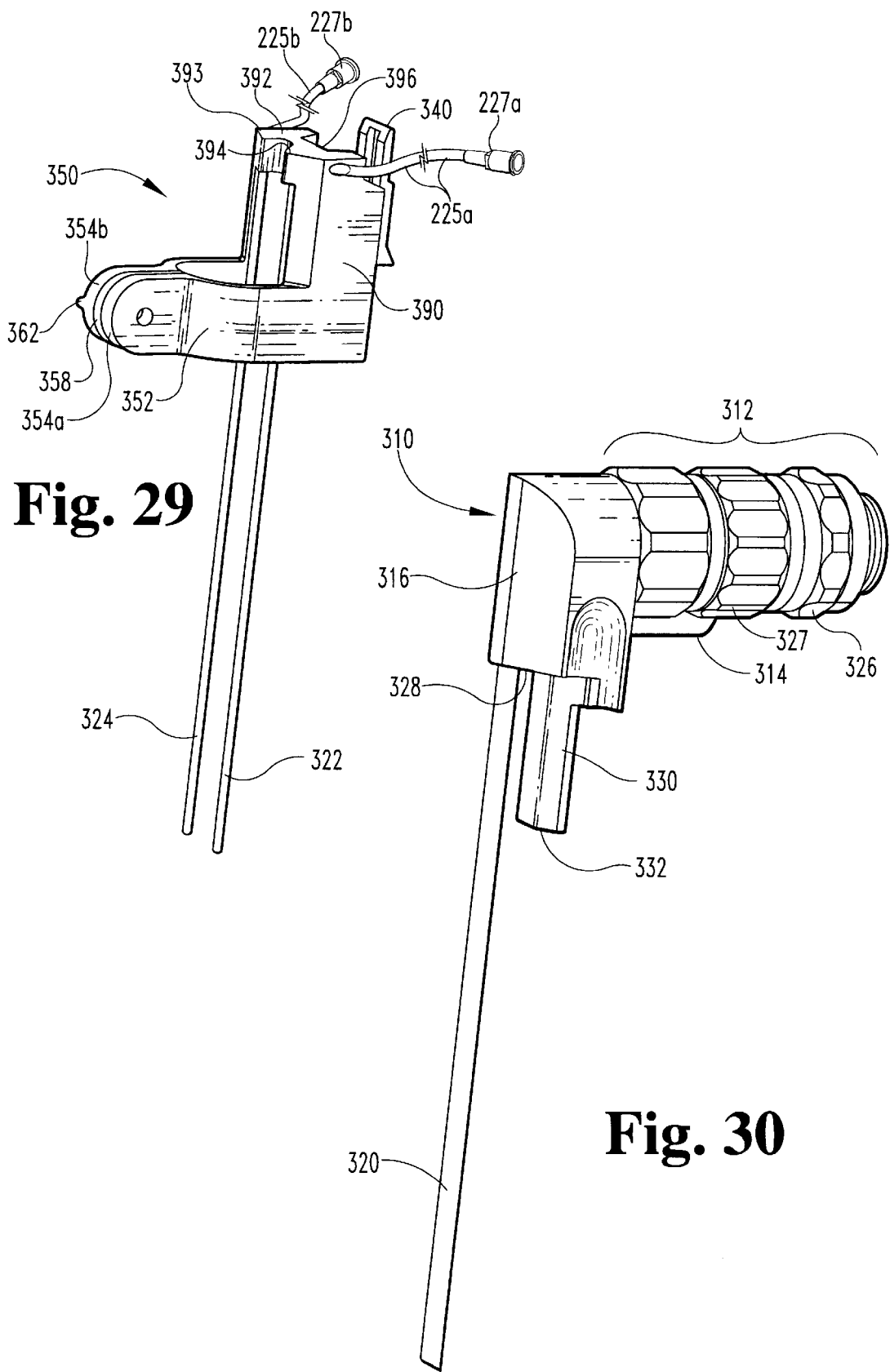

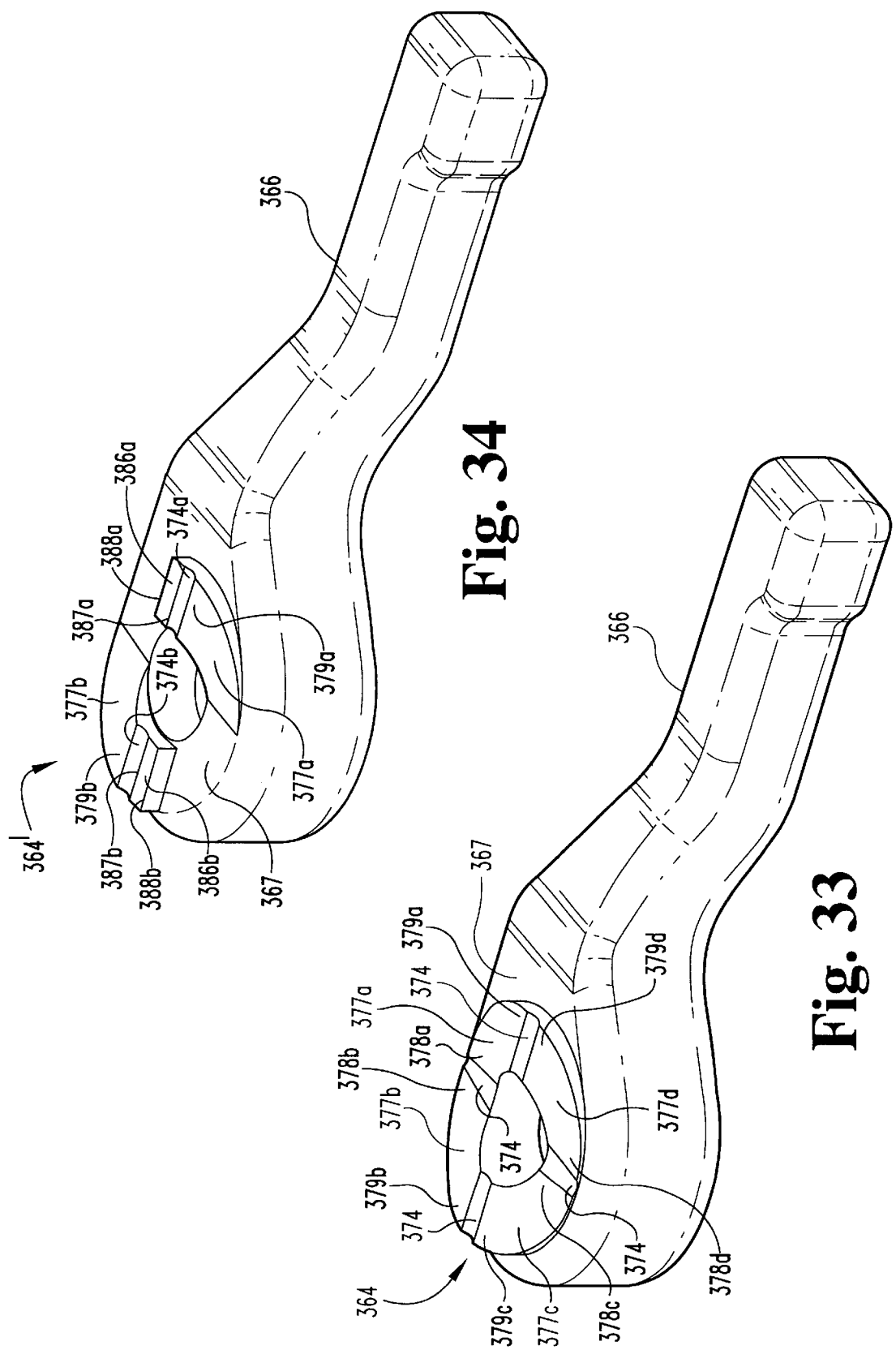

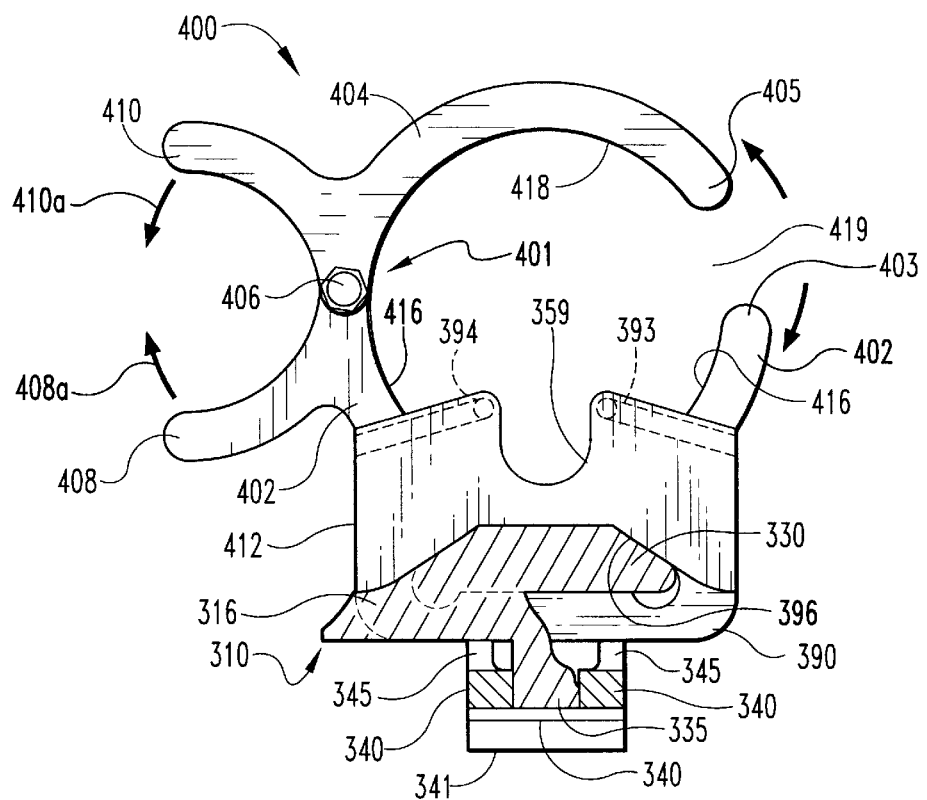
Fig. 35
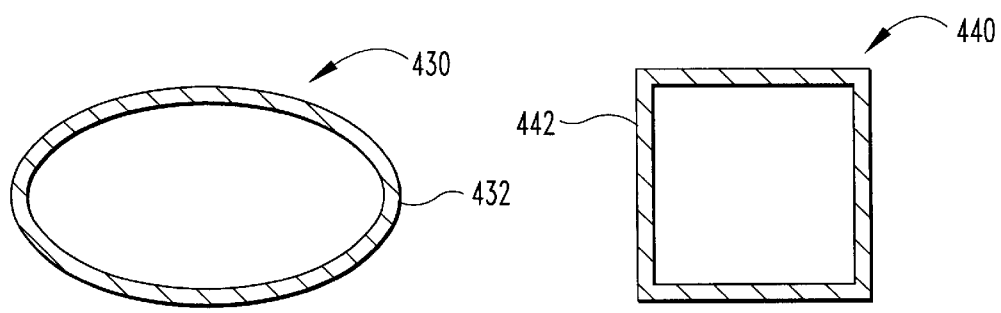
Fig. 36  Fig. 37

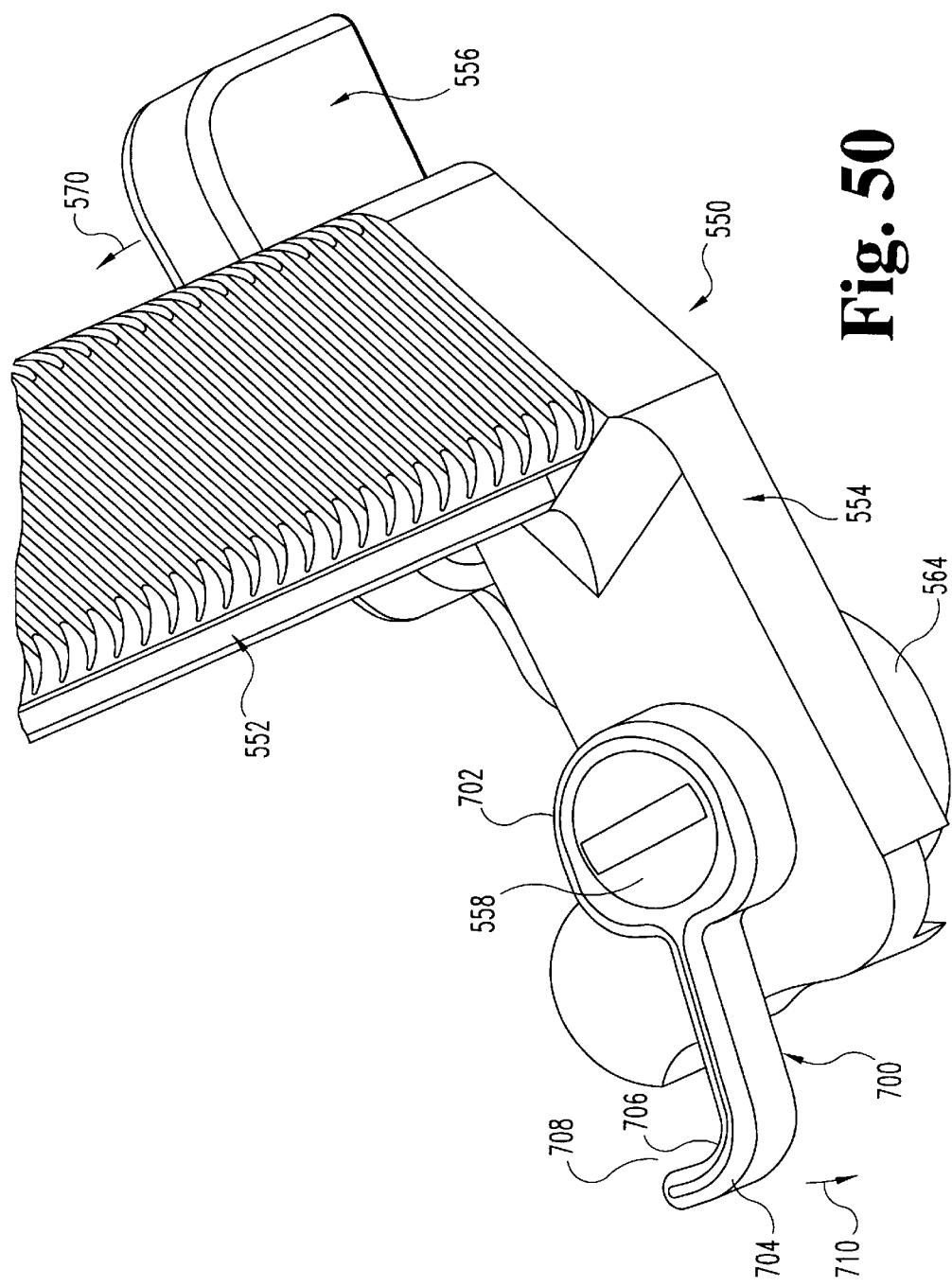

DEVICES AND METHODS FOR PERCUTANEOUS SURGERY

CROSS-REFERENCE TO RELATED APPLICATIONS

The present application is a continuation-in-part of International Patent Application No. PCT/US99/21866, Sep. 21, 1999, which is hereby incorporated by reference. The present application is also a continuation-in-part of U.S. patent application Ser. No. 09/233,879 filed Jan. 20, 1999, now U. S. Pat. No. 6,217,509 which is a division of U.S. patent application Ser. No. 08/736,626, filed on Oct. 24, 1996, now U.S. Pat No. 5,902,231, which is a continuation-in-part of U.S. patent application Ser. No. 08/620,933 file Mar. 22, 1996, now U.S. Pat. No. 5,792,044.

BACKGROUND OF THE INVENTION

The present invention relates to devices, instruments and methods for performing percutaneous surgeries, particularly at locations deep within the body. One specific application of the invention concern devices, instruments and techniques for percutaneous, minimally invasive spinal surgery. In another aspect of the invention, the percutaneous surgery is performed under direct vision at any location in the body.

Traditional surgical procedures for pathologies located deep within the body can cause significant trauma to the intervening tissues. These open procedures often require a long incision, extensive muscle stripping, prolonged retraction of tissues, denervation and devascularization of tissue. Most of these surgeries require room time of several hours and several weeks of post-operative recovery time due to the use of general anesthesia and the destruction of tissue during the surgical procedure. In some cases, these invasive procedures lead to permanent scarring and pain that can be more severe than the pain leading to the surgical intervention.

Minimally invasive alternatives such as arthroscopic techniques reduce pain, post-operative recovery time and the destruction of healthy tissue. Orthopedic surgical patients have particularly benefited from minimally invasive surgical techniques. The site of pathology is accessed through portals rather than through a significant incision thus preserving the integrity of the intervening tissues. These minimally invasive techniques also often require only local anesthesia. The avoidance of general anesthesia reduces post-operative recovery time and the risk of complications.

Minimally invasive surgical techniques are particularly desirable for spinal and neurosurgical applications because of the need for access to locations deep within the body and the danger of damage to vital intervening tissues. For example, a common open procedure for disc herniation, laminectomy followed by discectomy requires stripping or dissection of the major muscles of the back to expose the spine. In a posterior approach, tissue including spinal nerves and blood vessels around the dural sac, ligaments and muscle must be retracted to clear a channel from the skin to the disc. These procedures normally take at least one-two hours to perform under general anesthesia and require post-operative recovery periods of at least several weeks. In addition to the long recovery time, the destruction of tissue is a major disadvantage of open spinal procedures. This aspect of open procedures is even more invasive when the discectomy is accompanied by fusion of the adjacent vertebrae. Many patients are reluctant to seek surgery as a solution to pain caused by herniated discs and other spinal conditions because of the severe pain sometimes associated with the muscle dissection.

In order to reduce the post-operative recovery time and pain associated with spinal and other procedures, microsurgical techniques have been developed. For example, in microsurgical discectomies, the disc is accessed by cutting a channel from the surface of the patient's back to the disc through a small incision. An operating microscope or loupe is used to visualize the surgical field. Small diameter microsurgical instruments are passed through the small incision and between two laminae and into the disc. The intervening tissues are disrupted less because the incision is smaller. Although these micro-surgical procedures are less invasive, they still involve some of the same complications associated with open procedures, such as injury to the nerve root and dural sac, perineural scar formation, reherniation at the surgical site and instability due to excess bone removal.

Other attempts have been made for minimally invasive procedures to correct symptomatic spinal conditions. One example is chemonucleolysis which involved the injection of an enzyme into the disc to partially dissolve the nucleus to alleviate disc herniation. Unfortunately, the enzyme, chymopapain, has been plagued by concerns about both its effectiveness and complications such as severe spasms, post-operative pain and sensitivity reactions including anaphylactic shock.

The development of percutaneous spinal procedures has yielded a major improvement in reducing recovery time and post-operative pain because they require minimal, if any, muscle dissection and they can be performed under local anesthesia. For example, U.S. Pat. No. 4,545,374 to Jacobson discloses a percutaneous lumbar discectomy using a lateral approach, preferably under fluoroscopic X-ray. This procedure is limited because it does not provide direct visualization of the discectomy site.

Other procedures have been developed which include arthroscopic visualization of the spine and intervening structure. U.S. Pat. Nos. 4,573,448 and 5,395,317 to Kambin disclose percutaneous decompression of herniated discs with a posterolateral approach. Fragments of the herniated disc are evacuated through a cannula positioning against the annulus. The '317 Kambin patent discloses a biportal procedure which involves percutaneously placing both a working cannula and a visualization cannula for an endoscope. This procedure allows simultaneous visualization and suction, irrigation and resection in disc procedures.

Unfortunately, disadvantages remain with these procedures and accompanying tools because they are limited to a specific application or approach. For example, Jacobson, Kambin, and other references require a lateral or a posterolateral approach for percutaneous discectomy. These approaches seek to avoid damage to soft tissue structures and the need for bone removal because it was thought to be impractical to cut and remove bone through a channel. However, these approaches do not address other spinal conditions which may require a mid-line approach, removal of bone, or insertion of implants or other technique.

U.S. Pat. No. 5,439,464 to Shapiro discloses a method and instruments for performing arthroscopic spinal surgeries such as laminectomies and fusions with a mid-line or medial posterior approach using three cannulae. Each of the cannulae requires a separate incision. While Shapiro discloses an improvement over prior procedures which were limited to a posterolateral or lateral approach for disc work, Shapiro's procedure still suffers from many of the disadvantages of known prior percutaneous spinal surgery techniques and tools. One disadvantage of the Shapiro procedure is its requirement of a fluid work space. Another significant detriment is that the procedure requires multiple portals into the patient.

Fluid is required in these prior procedures to maintain the working space for proper function of optics fixed within a prior art cannula and inserted percutaneously. Irrigation, or the introduction of fluid into the working space, can often be logistically disadvantageous and even dangerous to the patient for several reasons. The introduction of fluid into the working space makes hemostasis more difficult and may damage surrounding tissue. Excess fluid may dangerously dilute the sodium concentration of the patient's blood supply which can cause seizures or worse. The fluid environment can also make drilling difficult due to cavitation. The requirement for a fluid environment generally increases expenses associated with the surgery and adds to the complexity of the surgery, due in part to the relatively high volume of fluid required.

A need has remained for devices and methods that provide for percutaneous minimally invasive surgery for all applications and approaches. A significant need is also present in this field for techniques and instruments that permit surgical procedures in the working space under direct vision while employing microscopic and endoscopic viewing systems. Procedures that reduce the number of entries into the patient are also highly desirable. The fields of spinal and neuro surgery particularly require devices and techniques that minimize the invasion into the patient and that are streamlined and concise in their application.

SUMMARY OF THE INVENTION

The present invention is directed to methods and devices for performing surgery in a patient. In one preferred form, the present invention contemplates a cannula that includes a working channel to provide access to a location in the patient along with the selective employment of an endoscopic viewing system or a microscopic viewing system to view the location through the working channel. In another preferred form, the present invention contemplates mounting of a clamp assembly on the proximal end of a cannula. The clamp assembly includes a viewing element mounting portion having a length along which a viewing element can be selectively positioned.

The present invention further contemplates an elongated cannula sized for introduction into a patient. The cannula defines a length and a working channel between a distal working end and an opposite proximal end. A clamp assembly having a viewing element mounting portion can be engaged to the cannula with the viewing element mounting portion extending proximally from the cannula. A viewing element can be selectively engaged at various positions along the length of the viewing element mounting portion.

In a further form, the present invention contemplates a device for supporting a viewing element during surgery in a patient. The device includes a cannula having a working channel defined by an inner surface that extends between a proximal end and a distal end of the cannula. A clamp assembly is engageable to the cannula by applying a clamping force to the inner surface and the outer surface of the cannula. The clamp assembly includes a viewing element mounting portion that extends proximally from the cannula. In one embodiment, the clamp assembly includes a foot that extends from the viewing element mounting portion. The foot has a channel positionable over the proximal end of the cannula. A lever arm is pivotably attached to the foot. The lever arm includes a cam member with a cam surface frictionally engageable to the outer surface of the cannula.

In yet another form, a device for performing surgery in a patient is provided that includes a cannula with a distal working end and a proximal end and a working channel extending therethrough. The cannula has a length between the proximal end and the distal end such that the proximal end is positioned at the skin level of the patient when said distal end is positioned at a desired location in the patient. A clamp assembly that supports a viewing element is engageable to the proximal end of the cannula. In a preferred form the viewing element includes an optics cannula that extends into the working channel.

According to another aspect of the invention, a kit for use in percutaneous surgery is provided. The kit includes an elongated cannula having a working channel extending between a distal working end and an opposite proximal end. The kit further includes a clamp assembly removably engageable to the cannula and a viewing element supportable by the clamp assembly with an optics cannula of the viewing element in the working channel. The kit also includes a microscope positionable over the proximal end of the cannula.

The present invention also contemplates surgical methods and techniques employing the instruments and devices described herein.

These and other aspects, forms, features, objects, and advantages are further described in the following description of the illustrated embodiments.

DESCRIPTION OF THE FIGURES

FIG. 16 is a side elevational view of a scope body forming part of the fixture depicted in FIGS. 13 and 14.

FIG. 17 is a bottom elevational view of the scope body shown in FIG. 16.

FIG. 18 is a top elevational view of a lever arm forming part of a barrel clamp mechanism used with the fixture depicted in FIG. 14.

FIG. 19 is an end cross-sectional view of the lever arm shown in FIG. 18 taken along line 19—19 as viewed in the direction of the arrows.

FIG. 20 is a top elevational view of a barrel cam forming part of a barrel clamp mechanism incorporated into the fixture depicted in FIG. 14.

FIG. 21 is a side elevational view of the barrel cam shown in FIG. 20.

FIG. 25 is a side elevational view of a tissue retractor incorporating an optical viewing device.

FIG. 26 is a top elevational view of the tissue retractor incorporating an optical viewing device as shown in FIG. 25.

FIG. 29 is a side perspective view of one embodiment of a modular clamp for use with the assembly of FIG. 28.

FIG. 30 is a side perspective view of one embodiment of an endoscope for use with the assembly of FIG. 29.

FIG. 33 is a perspective view of one embodiment of a lever arm forming part of the barrel clamp mechanism shown in FIG. 32.

FIG. 34 is a perspective view of another embodiment of a lever arm forming part of the barrel clamp mechanism of FIG. 32.

FIG. 35 is a partially fragmented cross-sectional view of an alternate embodiment of the device illustrated in FIG. 32.

FIG. 36 is a sectional view of an alternate embodiment cross-section of a cannula for use with the present invention.

FIG. 37 is a sectional view of another alternate embodiment cross-section of a cannula for use with the present invention.

FIG. 50 is a perspective view of a clamp assembly comprising a portion of the device of FIG. 49.

DESCRIPTION OF THE PREFERRED EMBODIMENTS

Figure 1:
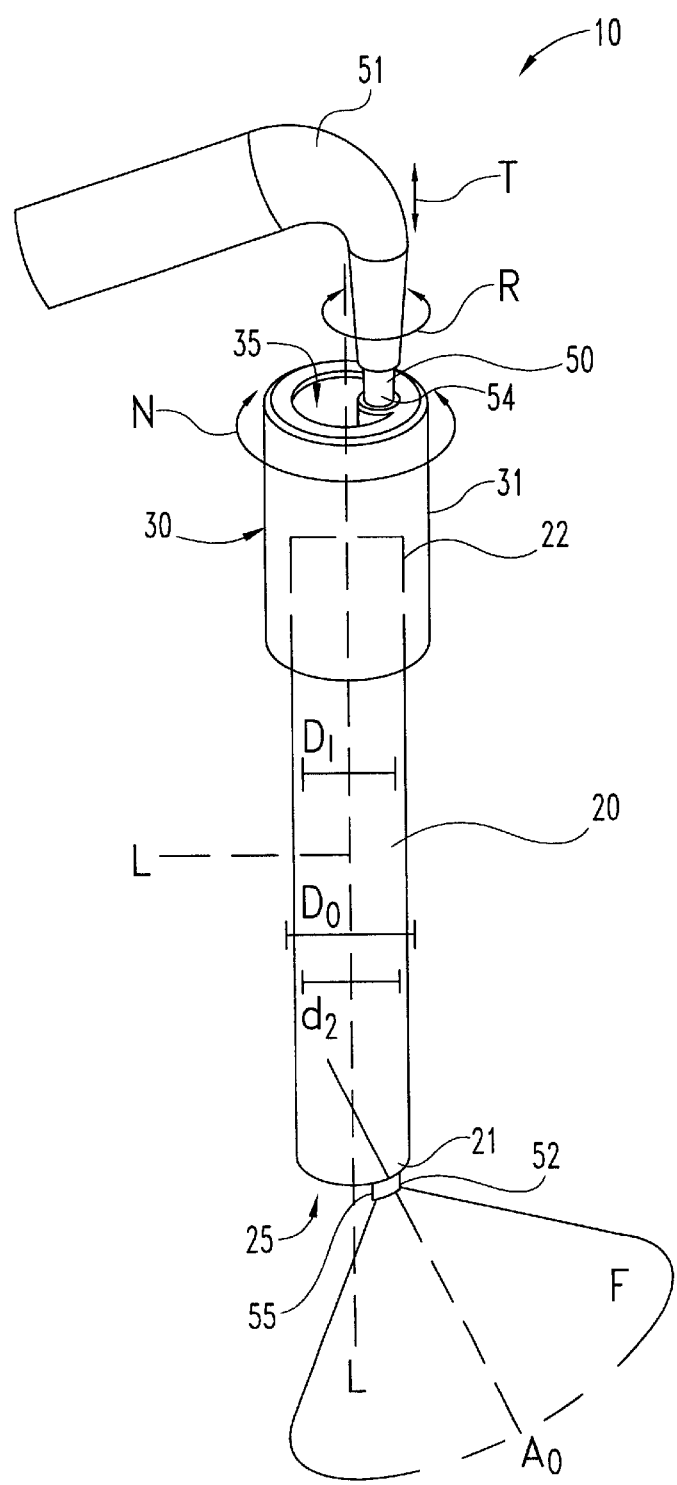
FIG. 1 is a side elevational view of a device according to this invention.

For the purposes of promoting an understanding of the principles of the invention, reference will now be made to the embodiments illustrated in the drawings and specific language will be used to describe the same. It will nevertheless be understood that no limitation of the scope of the invention is thereby intended, such alterations and further modifications in the illustrated devices and described methods, and such further applications of the principles of the invention as illustrated therein being contemplated as would normally occur to one skilled in the art to which the invention relates.

The present invention provides instruments and methods for performing percutaneous surgery, including spinal applications such as laminotomy, laminectomy, foramenotomy, facetectomy or discectomy, with a single working channel endoscope. The present inventors have discovered that many percutaneous surgeries may be performed without a fluid workspace through the use of optics which move independently of the cannula. The present invention contemplates techniques and instruments that can be implemented with or without a fluid environment.

This invention also brings the advantages of percutaneous procedures to applications that previously required open surgery. One advantage is based upon the further discovery that bone work can be performed percutaneously through a large working channel. Another advantage is realized in the use of a single portal within the patient to perform a wide range of simultaneous procedures.

According to one embodiment of the present invention, as depicted in FIG. 1, a device 10 is provided for use in percutaneous surgery which includes an elongated cannula 20 having a first inner diameter $D_I$ and an outer diameter $D_O$ sized for percutaneous introduction into a patient. The cannula 20 also includes a distal working end 21 and an opposite proximal end 22. The cannula defines a working channel 25 between the ends 21, 22 having a second diameter $d_2$ equal to the first inner diameter $D_I$ sized for receiving a tool therethrough. The cannula has a length along its longitudinal axis L that is sized to pass through the patient from the skin to an operative site or working space. In some cases, the working space may be adjacent a vertebra or disc, or in the spinal canal.

An elongated viewing element 50 is mountable inside cannula 20 adjacent the working channel 25. The viewing element 50 has a first end 51 connectable to a viewing apparatus, such as an eyepiece or camera, and an opposite second end 52 disposed or positionable adjacent the distal working end 21 of the cannula 20. The particular elongated viewing element 50 is not critical to the invention. Any suitable viewing element is contemplated that creates an optical or image transmission channel. In one embodiment, the elongated viewing element 50 includes a fiber optic scope 54 and a lens 55 at the second end 52. Preferably, the fiber optic scope includes illumination fibers and image transmission fibers (not shown). Alternatively, the viewing element may be a rigid endoscope or an endoscope having a steerable or bendable tip.

One advantage of this invention is that it provides optics which are movable relative to the cannula 20. Because the optics are movable, it is not necessary to provide a fluid-maintained work space. The optics can be removed, cleaned and replaced while the cannula is percutaneously positioned within the patient over the working space. Any configuration which allows the optics to be movably supported adjacent the working channel 25 is contemplated. In one embodiment, shown in FIGS. 1–3, a fixture 30 is provided for mounting the elongated viewing element 50 to the cannula 20. Preferably, the fixture 30 includes a housing 31 attachable to the proximal end 22 of the cannula 20. The working channel opening 35 is sized to substantially correspond to the second diameter $d_2$ of the working channel 25 to receive tools. The fixture 30 includes a housing 31 which defines a working channel opening 35 arranged to communicate with the working channel 25 when the fixture 30 is mounted to the cannula 20. The working channel opening 35 is sized to receive tools therethrough for passage through the working channel 25. In the embodiments shown in FIGS. 1–3, the fixture 30 is configured to mount the viewing element 50 within the working channel 25.

The housing 31 also defines an optics bore 60 adjacent the working channel opening 35. The optics bore 60 has a longitudinal axis l that is preferably substantially parallel to the axis L of the cannula and working channel. The optics bore 60 is preferably sized to removably receive the elongated viewing element 50 therethrough. The fixture 30 preferably supports the viewing element 50 for movement within the optics bore 60 along the longitudinal axis l of the bore 60 to extend or retract the lens 55 relative to the distal working end 21 of the cannula 20. The retractable/extendable feature of the optics of this invention provides an advantage over prior endoscopes because it eliminates the requirement for a fluid workspace. While the device 10 and its viewing element 50 can be easily used in a fluid environment, the fluid is not essential for the system to operate, contrary to prior systems. Furthermore, many of the prior endoscopes were not suited to access certain areas because of their large diameters. For example, prior endoscopes could not access the spinal canal. However, with this invention, access to the spinal canal is not limited by the diameter of the channel or cannula. The cannula 20 can be left behind in the soft tissue or supported by the lamina while the second end 52 of the elongated viewing element 50 can be advanced into the spinal canal along with any spinal instruments which have been inserted into the working channel 25.

Preferably the fixture 30 also supports the viewing element 50 for the rotation within the optics bore 60 about the longitudinal axis l of the bore 60. The lens 55 of the viewing element 50 defines an optical axis $A_O$. As in many endoscopes, the optical axis $A_O$ can be offset at an angle relative to the longitudinal axis l of the optics bore 60. This feature allows the optical axis $A_O$ of the lens to be swept through a conical field of the view F for greater visibility of the working space. The fixture 30 can further be configured so that the viewing element 50 is rotatable relative to the cannula 20. In this embodiment, the housing 31 is rotatable relative to the cannula 20 so that the second longitudinal axis l of the optics bore 60 rotates about the longitudinal axis L of the working channel 25. The rotatable features of this invention allows visualization of the entire working space. This feature also aids in simplifying the surgical procedure because the optics 50 and accompanying fittings can be moved out of the way of the surgeon's hands and tools passing through the working channel.

Figure 3:
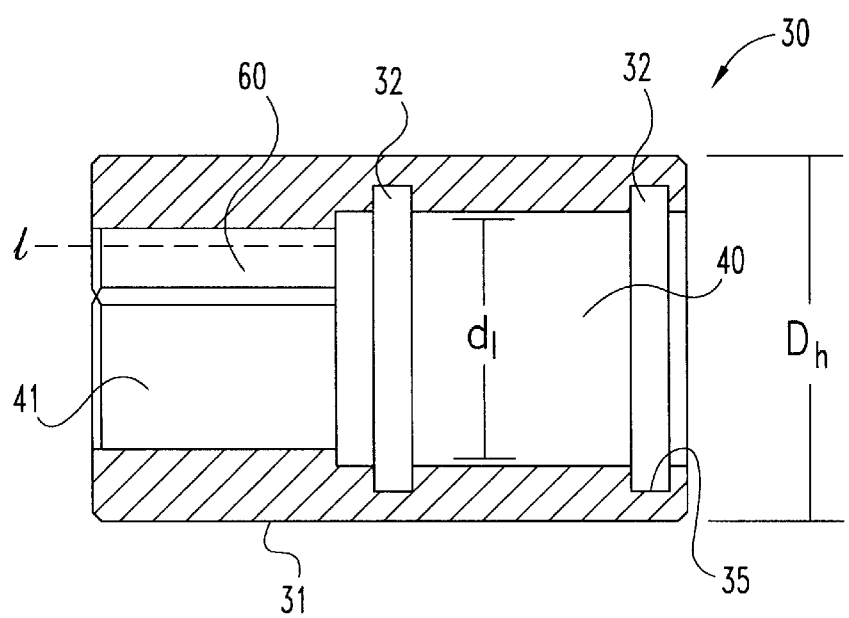
FIG. 3 is a side cross-sectional view of the fixture shown in FIG. 2.

In one embodiment depicted in FIG. 3, the housing 31 defines a receiver bore 40 having an inner diameter $d_r$ slightly larger than the outer diameter $D_O$ of the cannula 20. In this configuration, the proximal end 22 of the cannula 20 can be received within the receiver bore 40 so that the housing 31 can rotate about the proximal end 22 of the cannula 20. As shown in FIG. 3, the housing 31 also includes an upper bore 41 which is contiguous with the working channel opening 35 and the receiver bore 40. In one embodiment, the optics bore 60 is disposed within the upper bore 41 of the housing 31.

Figure 2:
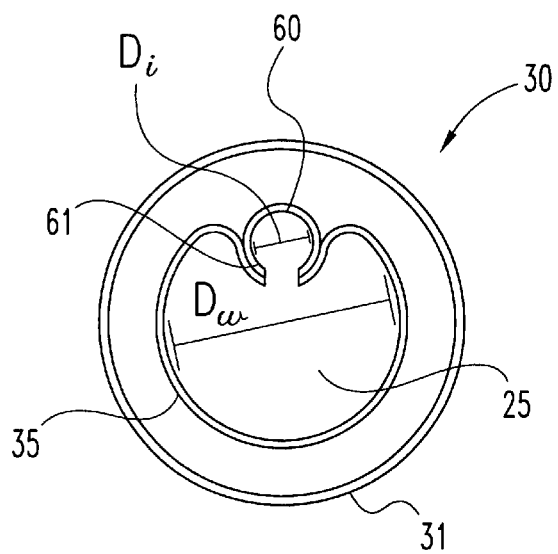
FIG. 2 is a top elevational view of a fixture for supporting a viewing device within a cannula according to this invention.

In a preferred embodiment depicted in FIG. 2, the optics bore 60 is defined by a C-shaped clip 61 disposed within the upper bore 41. Preferably, the C-shaped clip 61 is formed of a resilient material and the optics bore 60 defined by the clip 61 has an inner diameter $D_i$ that is slightly less than the outer diameter of the elongated viewing element 50. When the viewing element 50 is pushed into the optics bore 60 it resiliently deflects the C-shaped clip 61. The resilience of the clip 61 provides a gripping force on the element 50 to hold it in the desired position, while still allowing the element 50 to be repositioned. Alternatively, the optics bore 60 can have an inner diameter larger than the outer diameter of the viewing element. In this instance, the viewing element 50 can be supported outside the device 20, either manually or by a separate support fixture.

Preferably the device 10 provides engagement means for securely yet rotatably engaging the fixture 30 to the cannula 20. Most preferably, the fixture 30 is configured to engage a standard cannula 20. Engagement means can be disposed between the housing 31 and the cannula 20 when the fixture 30 is mounted to the proximal end 22 of the cannula 20 for providing gripping engagement between the housing 31 and the cannula 20. In one embodiment depicted in FIG. 3 the engagement means includes a number of grooves 32 within the receiver bore 40 and a resilient sealing member, such as an O-ring (see FIG. 11) disposed in each groove 32. The sealing members, or O-rings, disposed between the housing 31 and the outer diameter $D_O$ of the cannula 20 rotatably secure the fixture 30 to the cannula 20. The O-rings provide sufficient resistance to movement to hold the fixture 30 in a selected position on the cannula. In another embodiment, the housing 31 defines a receiver bore 40 which has an inner diameter $d_1$ which is only slightly larger than the outer diameter $D_O$ of the cannula 20 so that the housing 31 can rotate freely about the cannula 20.

The working channel 25 and the working channel opening 35 are both sized to receive a tool or instrument therethrough. Preferably, the working channel opening 35 of the housing 31 has a diameter Dw which is substantially equal to the inner diameter $d_2$ of the working channel 25 so that the effective diameter of the working channel is not reduced by the fixture 30. This configuration provides a maximum amount of space for the insertion of tools into the working channel 25. The present invention is advantageous because standard micro-surgical spinal tools can be inserted into the working channel and manipulated to perform a surgical procedure. The present invention is particularly advantageous because the working channel 25 will simultaneously accept a plurality of movable instruments. No other known prior art device has a working channel that accepts more than one movable instrument at a time through a single port. Therefore, according to this invention, an entire percutaneous surgical procedure can be performed through the working channel 25 of the device 10 under direct visualization using the viewing element 50 disposed within the optics bore 60.

In accordance with the present embodiment, the components of the device 10 are cylindrical in configuration. In other words, the cannula 20, working channel 25 and fixture 30 have corresponding cylindrical configurations which yield the various diameters $D_i$, $D_o$, $D_w$ and $d_2$. In accordance with other embodiments contemplated as part of the invention, these diameters may be non-circular inner and outer dimensions, such as oval or square shaped. For example, a cannula 20 modified to a square cross-section, such as illustrated in FIG. 37, would still provide a large working channel, such as working channel 25. In another embodiment, the cross-section is oval, such as that illustrated in FIG. 36.

Likewise, a corresponding fixture 30 have a square cross-section would also provide a large working channel opening $D_w$. In the case of the non-circular configurations, the fixture 30 in accordance with the present embodiment would be unable to rotate around the circumference of the cannula 20, as permitted by the circular configurations. On the other hand, even the non-circular configurations will permit axial movement of the optical viewing element and rotation of the viewing element about its own axis, as set forth more fully herein.

In accordance with a further variation of the present invention, the cannula 20 can be replaced by a similar device that is capable of maintaining a large working channel 25. For example, the cannula 20 can be replaced by an expanding cannula or dilator apparatus. In one specific embodiment, the apparatus can be a spiral wound tube that is unwound or expanded to provide the working channel dimension. Alternatively, multiple tissue dilators, such as speculae, can be expanded to create a working space. In these configurations, the fixture 30 may still be used to support the optical viewing element 50 once the expandable dilator or tissue retractor reaches its full working channel dimension.

Although standard micro-surgical instruments may be used with the present invention, this invention also contemplates certain novel tools which capitalize on and enhance the advantages of this invention.

Figure 4:
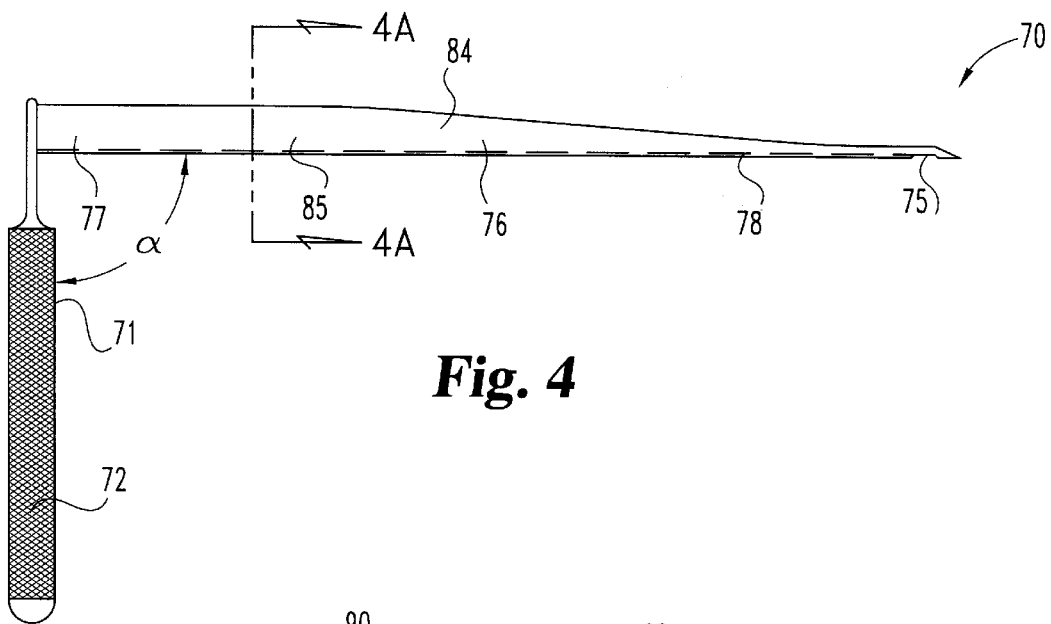
FIG. 4 is a side elevational view of a retractor according to one embodiment of this invention.
Figure 4A:
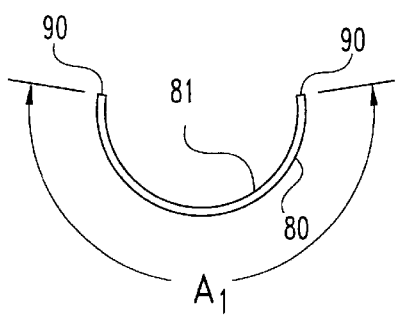
FIG. 4A is an end cross-sectional view of the retractor of FIG. 4 taken along lines A—A.
Figure 5:
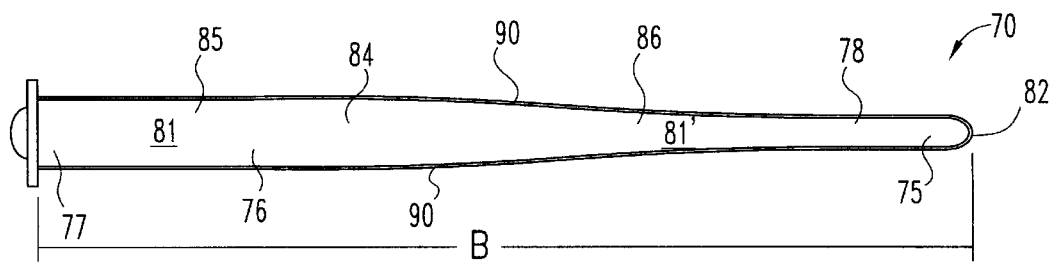
FIG. 5 is a top elevational view of the retractor shown in FIG. 4.
Figure 6:
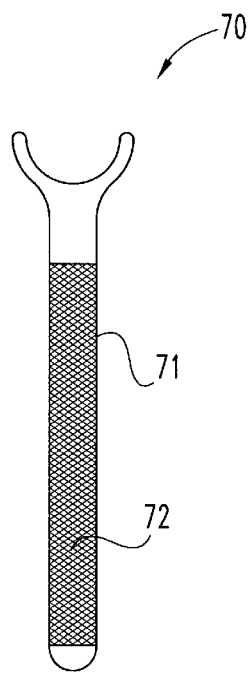
FIG. 6 is an end elevational view of the retractor shown in FIGS. 4 and 5.

According to one preferred embodiment of the invention, a tissue retractor 70 is provided as depicted in FIGS. 4–6. The retractor 70 is removably and rotatably insertable through the working channel 25 and the working channel opening 35 of the device 10. The tissue retractor 70 includes a working tip 75 configured to atraumatically displace tissue as the retractor 70 is manipulated through the tissue and a body 76 having a proximal first end 77 and a distal second end 78. The second end 78 can be integral with the working tip 75 which preferably has a blunt curved end 82. In addition, the working tip 75 is also preferably bent or curved away from the body 76, as shown in FIG. 4. The body 76 is sized to be rotatably received within the cannula 20 and has a length B from the first end 77 to the second end 78 sufficient so that the first end 77 and the working tip 75 can both extend outside the cannula 20 when the body 76 is within the cannula 20.

This invention contemplates any suitable retractor for use through the working channel 25. However, retractors such as the retractor 70 depicted in FIGS. 4–6 are preferred in which the body 76 includes a curved plate 84 that is configured to conform to the inner cylindrical surface 26 of the cannula without substantially blocking the working channel 25. The curved plate 84 has a convex surface 80 and an opposite concave surface 81. In one embodiment, the curved plate 84 includes a first plate portion 85 defining a first convex surface 80 and an opposite first concave surface 81. A second plate portion 86 is integral with the first plate portion 85 and is disposed between the first plate portion 85 and the working tip 75. The second plate portion 86 defines a second convex surface (not shown) and an opposite second concave surface 81'. Both the first plate portion 85 and the second plate portion 86 include opposite edges 90 extending substantially parallel to the length B of the body 76.

Preferably, the curved plate 84 subtends an arc $A_1$ between the opposite edges 90 of at least 200 degrees, and most preferably 270 degrees. In a specific embodiment, the second plate portion 86 and specifically the second concave surface 81' subtends an angle that decreases along the length of the retractor. Thus, in one embodiment, the second concave surface 81' subtends an angle of about 200 degrees adjacent the first plate portion 85, decreasing to an angle of less than about 10 degrees at end 78.

Figure 7A:
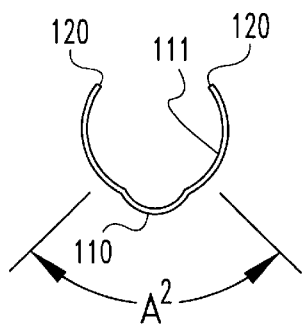
FIG. 7A is an end cross-sectional view of the retractor of FIG. 7 taken along lines A—A.
Figure 7B:
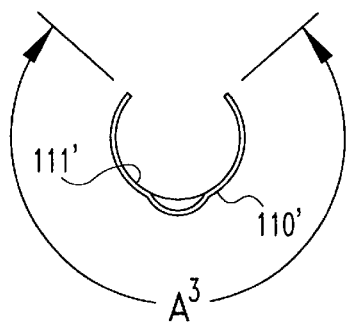
FIG. 7B is an end cross-sectional view of the retractor of FIG. 7 taken along lines B—B.
Figure 7:
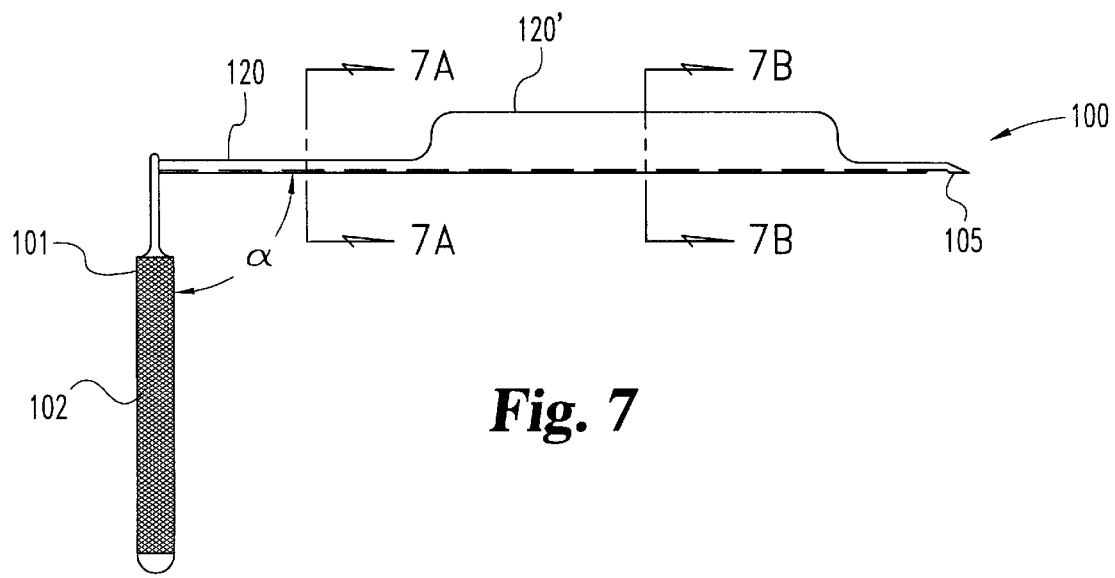
FIG. 7 is a side elevational view of a retractor according to another embodiment of this invention.
Figure 8:
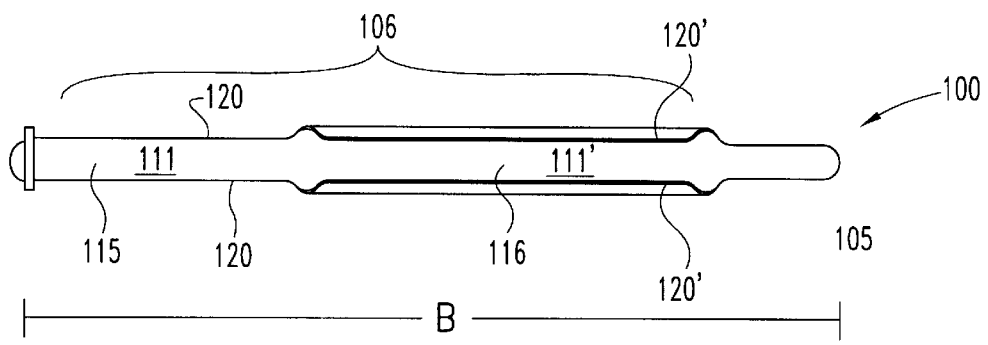
FIG. 8 is a top elevational view of the retractor shown in FIG. 7.

An alternate embodiment of a tissue retractor according to this invention is depicted in FIGS. 7–8. This retractor 100 has a body 106 which includes a first plate portion 115 defining a first convex surface 110 and an opposite first concave surface 111 and includes first opposite edges 120 extending substantially parallel to the length B of the body 106. The first plate portion 115 subtends a first arc $A_2$ between the first opposite edges 120. The retractor body 106 also includes a second plate portion 116 which is integral with the first plate portion 115 and is disposed between the first plate portion 115 and a working tip 105. The second plate portion 116 defines a second convex surface 110' and an opposite second concave surface 111' and includes second opposite edges 120' extending substantially parallel to the length B. The second plate portion 116 subtends a second arc $A_3$ between the second opposite edges 120' that is different from the first arc $A_2$ in this embodiment. Preferably, the first arc $A_2$ subtends an angle of less than 180 degrees and the second arc $A_3$ subtends an angle of more than 180 degrees. Most preferably, the first arc $A_2$ subtends an angle of about 90 degrees and the second arc $A_3$ subtends an angle of about 270 degrees.

The retractors of this invention may be provided with means for engaging the retractors 70, 100 within the working channel 25 of the cannula 20. For example, the convex surfaces 80, 110 can be configured to have a diameter that is greater than the diameter $D_I$ of the inner cylindrical surface 26 of the cannula 20. In that case, the body 76, 106 may be formed of a resilient material that is deformable to be insertable into the cannula 20 so that the convex surface 80, 110 is in contact with the inner cylindrical surface 26 of the cannula 20. When the body 76, 106 is deformed, it exerts an outward force against the surface 26 to frictionally hold the retractor in its selected position.

The preferred components provided by this invention are configured so that multiple tools and instruments can be accepted and manipulated within the working channel 25 of the cannula 20. The components are also configured so that more than one surgeon may manipulate instruments through the working channel 25 of the cannula 20 at one time. For example, one surgeon may be manipulating the retractor while another surgeon is drilling into a bone. The curvature of the body 76, 106 of the retractors 70, 100 provides more working space and increases visibility. Another feature is that the long axis of the component can be placed in the working channel 25 while a bend in the handle portion keeps hands away from the channel 25 so that more than one surgeon can work in the channel 25 and more tools can be placed in the channel 25. The retractors shown in FIGS. 4–8 each comprise an arm 71, 101 attached to the proximal first end 77, 107 of the body 76, 106. Preferably, as shown in FIGS. 4–8, the arm 71, 101 is at an angle α is about 90 degrees so that the arm 71, 101 is substantially perpendicular to the length L of the body 76, 106. Preferably, the arm 71, 101 has a gripping surface 72, 102 to facilitate manipulation of the retractor 70, 100.

Figure 9:
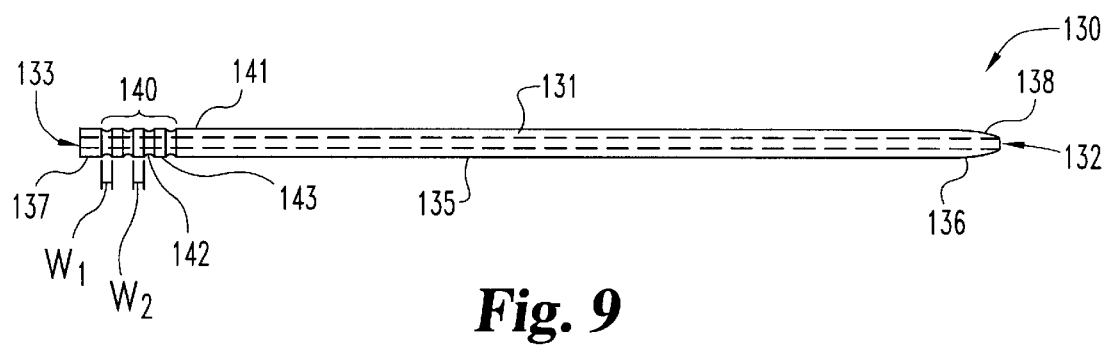
FIG. 9 is a side elevational view of a dilator according to this invention.

The present invention also provides tissue dilators usable with the device 10. Any dilator which is insertable into the working channel 25 of the cannula 20 is contemplated; however, as preferred dilator provided by this invention is depicted in FIG. 9. A dilator 130 preferably includes a hollow sleeve 135 defining a channel 131. The channel 131 allows the dilator 130 to be placed over a guidewire (not shown) or other dilators. The hollow sleeve 135 has a working end 136 defining a first opening 132 in communication with the channel 131 and an opposite end 137 defining a second opening 133. The working end 136 is tapered to a tapered tip 138 to atraumatically displace tissue. Preferably, a gripping portion 140 is provided on the outer surface 141 of the sleeve 135 adjacent the opposite end 137. In one embodiment, the gripping portion 140 is defined by a plurality of circumferential grooves 142 defined in the outer surface 141. The grooves 142 are configured for manual gripping of the dilator 130 to manipulate the dilator 130 through tissue. Preferably, the grooves 142 are partially cylindrical. In the embodiment shown in FIG. 9, the gripping portion 140 includes a number of circumferential flats 143 adjacent each of the circumferential grooves 142. The grooves 142 have a first width $W_1$ along the length of the sleeve 135 and the flats 143 have a second width $W_2$ along the length. Preferably, the first and second width $W_1$ and $W_2$ are substantially equal.

The present invention has application to a wide range of surgical procedures, and particularly spinal procedures such as laminotomy, laminectomy, foramenotomy, facetectomy and discectomy. Prior surgical techniques for each of these procedures has evolved from a grossly invasive open surgeries to the minimally invasive techniques represented by the patents of Kambin and Shapiro. However, in each of these minimally invasive techniques, multiple entries into the patent is required. Moreover, most of the prior minimally invasive techniques are readily adapted only for a posterolateral approach to the spine. The devices and instruments of present invention have application in an inventive surgical technique that permits each of these several types of surgical procedures to be performed via a single working channel.

This invention can also be used from any approach and in other regions besides the spine. For instance, the invention contemplates apparatus appropriately sized for use in transnasal, transphenoidal and pituitary surgeries.

The steps of the spinal surgical procedure in accordance with one aspect of the present invention are depicted in FIG. 10. As can be readily seen from each of the depicted steps (a)–(i), the present embodiment of the invention permits a substantially mid-line or medial posterior approach to the spine. Of course, it is understood that many of the following surgical steps can be performed from other approaches to the spine, such as posterolateral and anterior. In a first step of the technique, a guidewire 150 can be advanced through the skin and tissue into the laminae M of a vertebral body V. Preferably, a small incision is made in the skin to facilitate penetration of the guidewire through the skin. In addition, most preferably the guidewire, which may be a K-wire, is inserted under radiographic or image guided control to verify its proper positioning within the laminae M of the vertebra V. It is, of course, understood that the guidewire 150 can be positioned at virtually any location in the spine and in any portion of a vertebra V. The positioning of the guidewire is dependent upon the surgical procedure to be conducted through the working channel cannula of the present invention. Preferably, the guidewire 150 is solidly anchored into the vertebral bone, being tapped by a mallet if necessary.

In subsequent steps of the preferred method, a series of tissue dilators are advanced over the guidewire 150, as depicted in steps (b)–(d) in FIG. 10. Alternatively, the dilators can be advanced through the incision without the aid of a guidewire, followed by blunt dissection of the underlying tissues. In the specific illustrated embodiment, a series of successively larger dilators 151, 152 and 153 are concentrically disposed over each other and over the guidewire 150 and advanced into the body to sequentially dilate the perispinous soft tissues. Most preferably, the tissue dilators are of the type shown in FIG. 9 of the present application. In a specific embodiment, the dilators have successively larger diameters, ranging from 5 mm, to 9 mm to 12.5 mm for the largest dilator. Other dilator sizes are contemplated depending upon the anatomical approach and upon the desired size of the working channel.

In the next step of the illustrated technique, the working channel cannula 20 is advanced over the largest dilator 153, as shown in step (e), and the dilators and guidewire 150 are removed, as shown in step (f). Preferably, the working channel cannula 20 has an inner diameter $D_1$ of 12.7 mm so that it can be easily advanced over the 12.5 mm outer diameter of the large dilator 153. Larger working channel cannulas are contemplated depending upon the anatomical region and surgical procedure.

With the cannula 20 in position, a working channel is formed between the skin of the patient to a working space adjacent the spine. It is understood that the length of the cannula 20 is determined by the particular surgical operation being performed and the anatomy surrounding the working space. For instance, in the lumbar spine the distance between the laminae M of a vertebra V to the skin of the patient requires a longer cannula 20 than a similar procedure performed in the cervical spine where the vertebral body is closer to the skin. In one specific embodiment in which the cannula 20 is used in a lumbar discectomy procedure, the cannula has a length of 87 mm, although generally only about half of the length of the cannula will be situated within the patient during the procedure.

Figure 10A:
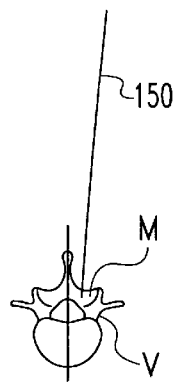
FIGS. 10(a)–(i) depicts the steps of a method according to this invention.
Figure 10B:
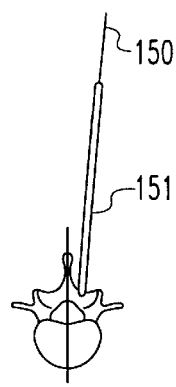
Figure 10C:
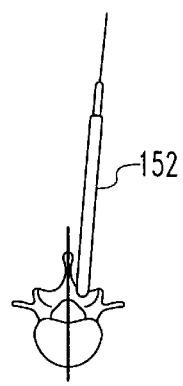
Figure 10D:
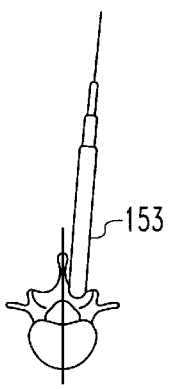
Figure 10E:
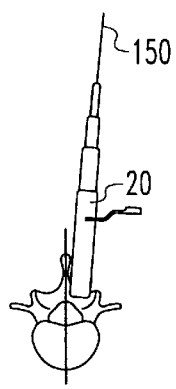
Figure 10F:
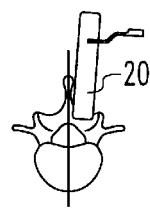
Figure 10G:
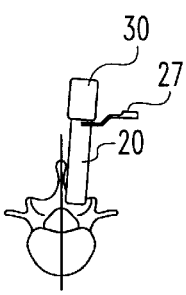
Figure 10H:
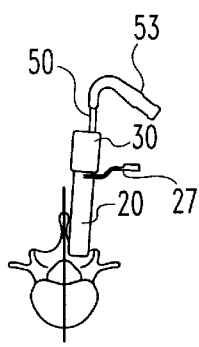
Figure 10I:
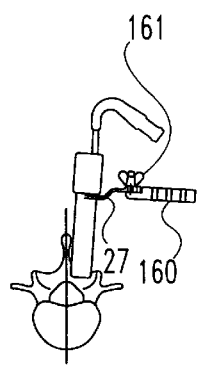

In accordance with the present surgical technique, the working channel cannula 20 is at least initially only supported by the soft tissue and skin of the patient. Thus, in one aspect of the preferred embodiment, the cannula 20 can include a mounting bracket 27 affixed to the outer surface of the cannula (FIG. 10(f), FIG. 11). This mounting bracket 27 can be fastened to a flexible support arm 160, which can be of known design. Preferably, the flexible support arm 160 is engaged to the bracket 27 by way of a bolt and wing nut 161, as shown in FIG. 10(i) and in more detail in FIG. 11, although other fasteners are also contemplated. This flexible arm 160 can be mounted to the surgical table and can be readily adjusted into a fixed position to provide firm support for the cannula 20. The flexible arm 160 is preferred so that it can be contoured as required to stay clear of the surgical site and to allow the surgeons adequate room to manipulate the variety of tools that would be used throughout the procedure.

Returning to FIG. 10, once the cannula 20 is seated within the patient, the fixture 30 can be engaged over the proximal end of the cannula 20. The fixture 30, as shown in FIGS. 2 and 3 and as described above, provides an optics bore 60 for supporting an elongated viewing element, such as element 50 shown in step h. In accordance with the invention, the viewing element 50 is advanced into the fixture 30 and supported by the optics bore 60 (FIG. 2). In one specific embodiment, the element 50 is most preferably a fiber optic scope, although a rod lens scope, "chip on a stick" or other viewing scopes may be utilized. In the final step (i) of the procedure shown in FIG. 10, the flexible arm 160 is mounted to the bracket 27 to support the cannula 20 which in turn supports the optical viewing element 50. This final position of step (i) in FIG. 10 is shown in more detail in FIG. 11. The viewing element 50 can be a variety of types, including a rigid endoscope or a flexible and steerable scope.

Figure 11:
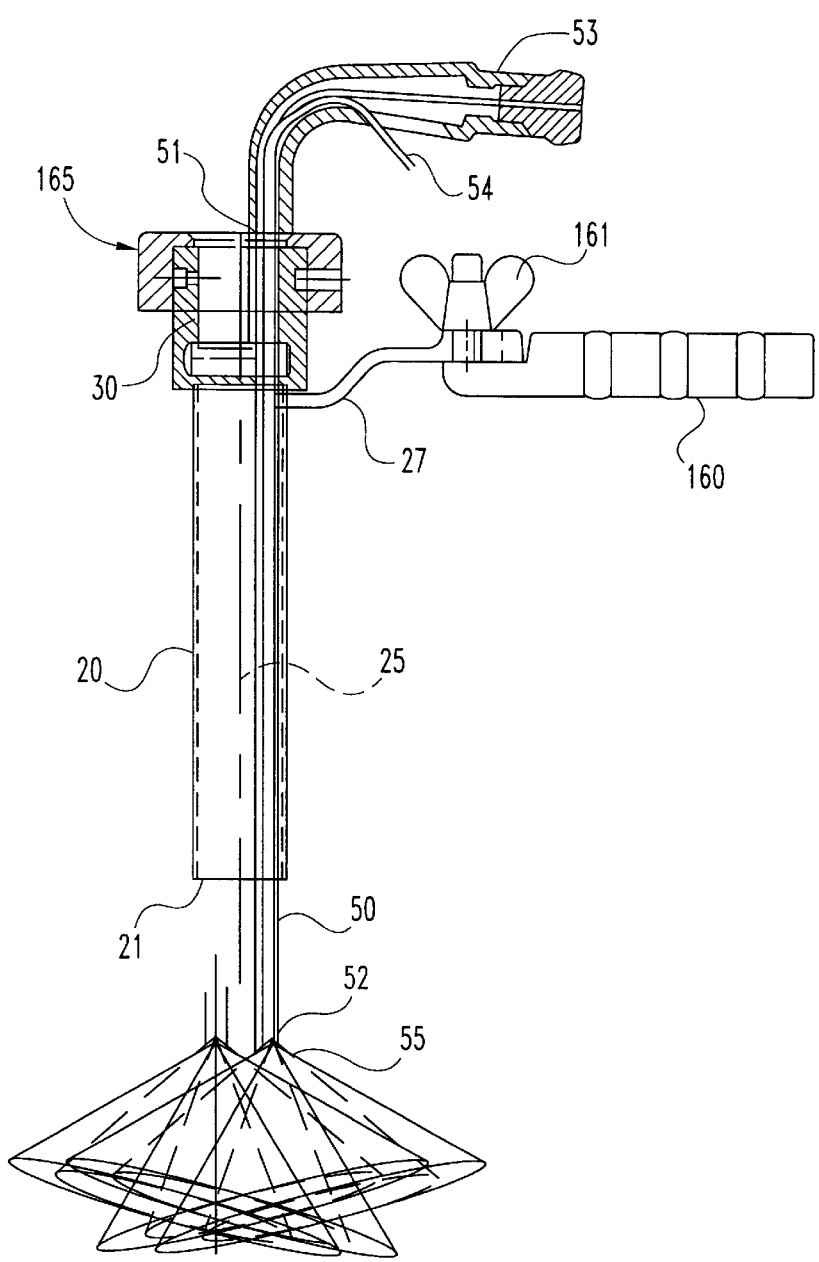
FIG. 11 is a side cross-sectional view of a device according to one embodiment of this invention.

With the viewing element or scope 50 supported by the fixture 30 the surgeon can directly visualize the area beneath the working channel 25 of the cannula 20. The surgeon can freely manipulate the viewing element 50 within the working channel 25 or beyond the distal end of the cannula into the working space. In the case of a steerable tip scope, the second end 52 of the viewing element 50, which carries the lens 55, can be manipulated to different positions, such as shown in FIG. 11. With virtually any type of viewing element, the manipulation and positioning of the scope is not limited by the procedure to be performed. For instance, in the case of a laminotomy, laminectomy, foramenotomy or facetectomy, a variety of rongeurs, curettes, and trephines can be extended through the working channel opening 35 (see FIG. 2) and through the working channel 25 of the cannula 20 (see FIG. 11) into the working space. It is understood that these various tools and instruments are designed to fit through the working channel. For instance, in one specific embodiment, the working channel 25 through the cannula 20 can have a maximum diameter $d_2$ of 12.7 mm. However, with the viewing element 50 extending into the working channel 25, the effective diameter is about 8 mm in the specific illustrated embodiment, although adequate space is provided within the working channel 25 around the viewing element 50 to allow a wide range of movement of the tool or instrument within the working channel. The present invention is not limited to particular sizes for the working channel and effective diameter, since the dimensions of the components will depend upon the anatomy of the surgical site and the type of procedure being performed.

Preferably, each of the tools and instruments used with the working channel cannula 20 are designed to minimize obstruction of the surgeon's visualization of and access to the working space at the distal end of the working channel cannula. Likewise, the instruments and tools are designed so that their actuating ends which are manipulated by the surgeon are displaced from the working channel cannula 20. One such example is the tissue retractor shown in FIGS. 4–8. With these retractors, the handles that are manually gripped by the surgeon are offset at about a 90 degree angle relative to the longitudinal axis of the tool itself.

In accordance with once aspect of the present invention, the surgical procedures conducted through the working channel cannula 20 and within the working space at the distal end of the cannula are performed "dry"—that is, without the use of irrigation fluid. In prior surgical techniques, the working space at the surgical site is fluid filled to maintain the working space and to assist in the use of the visualization optics. However, in these prior systems the visualization optics were fixed within the endoscope. In contrast, the device 10 of the present invention allows a wide range of movement for the viewing element 50 so that the lens 55 can be retracted completely within the working channel 25 of the cannula 20 to protect it from contact with the perispinous tissue or blood that may be generated at the surgical site.

Moreover, since the viewing element 50 is removable and replaceable, the element 50 can be completely removed from the fixture 30 so that the lens 55 can be cleaned, after which the viewing element 50 can be reinserted into the fixture and advanced back to the working space. Under these circumstances, then the need for irrigation is less critical. This feature can be of particular value when cutting operations are being performed by a power drill. It has been found in prior surgical procedures that the use of a power drill in a fluid environment can cause turbulence or cavitation of the fluid. This turbulence can completely shroud the surgeon's view of the surgical site at least while the drill is being operated. With the present invention, the dry environment allows continuous viewing of the operation of the power drill so that the surgeon can quickly and efficiently perform the necessary cutting procedures.

While the present invention permits the surgeon to conduct surgical procedures in the working space under a dry environment, irrigation may be provided separately through the working channel 25. Alternatively, the viewing device 50 itself may include a tube 54 supported by the fitting 53 through which modest amount of fluid can be provided to keep the visualization space clear. In addition, during a discectomy, aspiration of the excised tissue is preferred, and irrigation will frequently assist in rapid removal of this tissue. Thus, separate irrigation and aspiration elements can also be inserted through the working channel 25 as required by the procedure.

Figure 12:
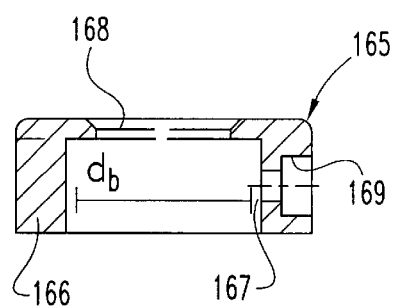
FIG. 12 is a side cross-sectional view of an aspiration cap as shown in FIG. 11.
Figure 13:
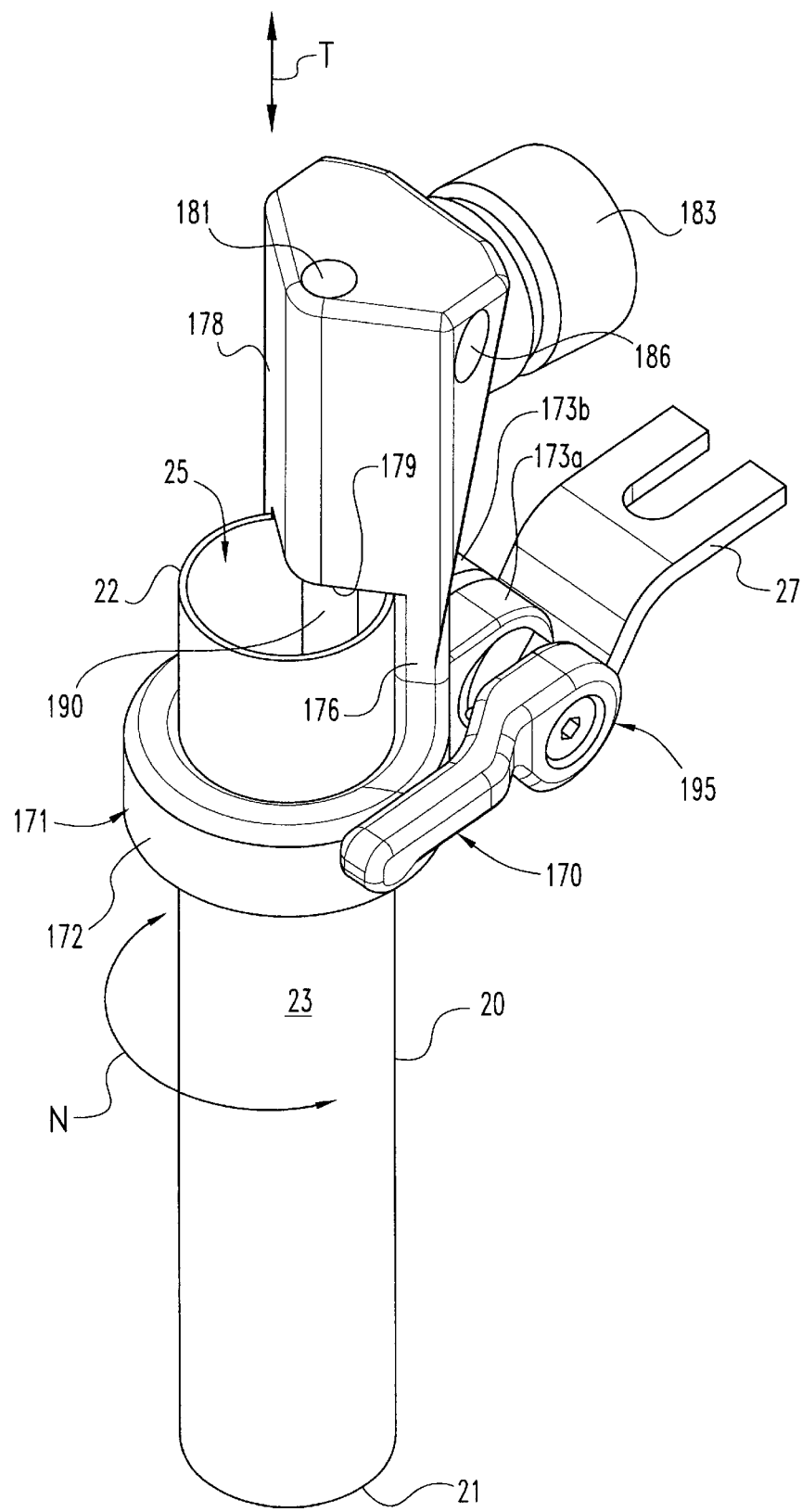
FIG. 13 is a top perspective view of a device according to another embodiment of the present invention.

As necessary, aspiration can be conducted directly through the working channel 25 of the cannula 20. In one specific embodiment, an aspiration cap 165 is provided as shown in FIGS. 11 and 12. The cap 165 includes a body 166 which defines a mating bore 167 having an inner diameter $d_b$ larger than the outer diameter $D_h$ of the housing 31 of fitting 30. A tool opening 168 is provided in communication with the mating bore 167. When the aspiration cap 165 is mounted over the housing 31, as shown in FIG. 11, the tool opening 168 communicates directly with the upper bore 41 and provides the same entry capabilities as the working channel opening 35 of the housing 31. The aspiration cap 165 is also provided with a tube receiver bore 169 which intersects the mating bore 167. The receiver bore 169 is configured to receive an aspiration tube through which a vacuum or suction is applied. In certain instances, the tool opening 168 may be covered while suction is applied through the tool receiver bore 169 and mating bore 167, and ultimately, through the working channel 25. Covering the opening 168 can optimize the aspiration effect through the working channel.

Returning again to the surgical technique of one embodiment of the present invention, once the working channel cannula 20 and the optics 50 are in position, as depicted in FIG. 10 step (i) and FIG. 11, the paraspinous tissue can be retracted using instruments as described above, and a laminectomy performed using various rongeurs, curettes and drills. As necessary, the cannula 20 can be angled to allow a greater region of bone removal, which may be necessary for access to other portions of the spinal anatomy. In some instances, access to the spinal canal and the posterior medial aspects of the disc annulus may require cutting a portion of the vertebral bone that is greater than the inner diameter of the working channel 25. Thus, some manipulation of the cannula 20 may be necessary to permit removal of a greater portion of bone. In other operations, multi-level laminectomies or foramenotomies may be necessary. In this instance, these multi-level procedures can be conducted by sequentially inserting the working channel cannula 20 through several small cutaneous incisions along the spinal mid-line. Alternatively, several working channel cannulas 20 can be placed at each of the small cutaneous incisions to perform the multi-level bone removal procedures.

Again, in accordance with the preferred illustrated surgical technique, an opening is cut into the laminae M of the vertebra V providing direct visual access to the spinal canal itself. As necessary, tissue surrounding the spinal nerve root can be removed utilizing micro-surgical knives and curettes. Once the spinal nerve root is exposed, a retractor, such as the retractors shown in FIGS. 4–8, can be used to gently move and hold the nerve root outside the working space. In one importance aspect of the two retractors 70, 100, the portion of the retractor passing through the working channel 25 generally conforms to the inner surface of the cannula 20 so that the working channel 25 is not disrupted by the retractor tool. Specifically, the effective diameter within the working channel 25 is reduced only by the thickness of the curved plates 84, 114 of the retractors 70, 100. In one specific embodiment, this thickness is about 0.3 mm, so it can be seen that the tissue retractors do not significantly reduce the space available in the working channel 25 for insertion of other tools and instruments.

With the tissue retractor in place within the working channel 25, bone within the spinal canal, such as may occur in a burst fracture, can be removed with a curette or a high speed drill. Alternatively, the fractured bone may be impacted back into the vertebral body with a bone impactor. At this point, if the spinal procedure to be performed is the removal of epidural spinal tumors, the tumors can be resected utilizing various micro-surgical instruments. In other procedures, the dura may be opened and the intradural pathology may be approached with micro-surgical instruments passing through the working channel cannula 20. In accordance with the specific illustrated technique, the nerve root retracted posterior medial disc herniations can be readily excised directly at the site of the herniation.

Figure 14:
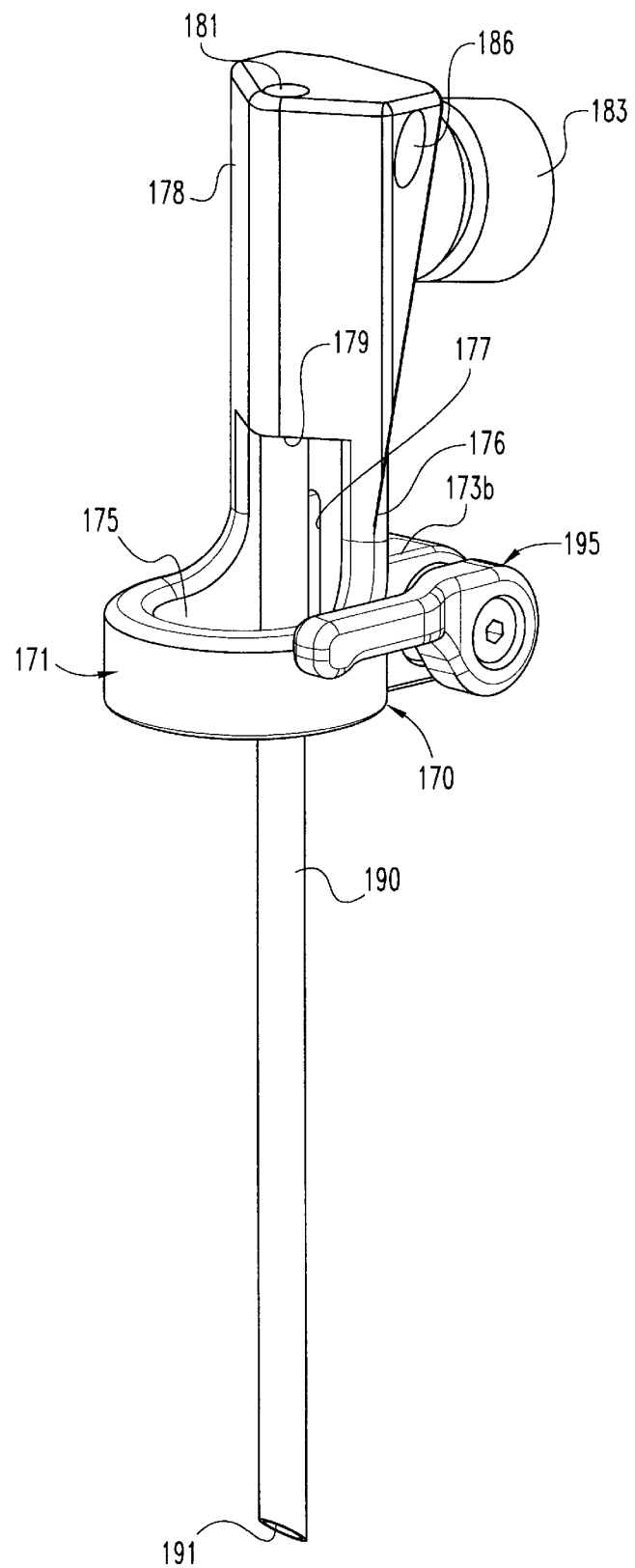
FIG. 14 is a side perspective view of a fixture for supporting a viewing device forming part of the device shown in FIG. 13.

In another embodiment of the invention, a working channel cannula, such as cannula 20, is provided with a fixture 170 for supporting optics and irrigation/aspiration components. In accordance with this embodiment, the fixture 170 includes a scope body 171 which is shown most clearly in FIGS. 13, 14, 16, and 17. The scope body 171 includes a clamping ring 172 configured to encircle the outer surfaces 23 of the cannula 20. In particular, the clamping ring 172 includes an inner clamping surface 175 (see FIG. 14). The clamping surface 175 has substantially the same configuration and dimension as the outer surface 23 of the cannula 20. The clamping ring 172 includes clamp arms 173a, b at the free ends of the ring. The clamp arms 173a, b define a slot 174 (see FIG. 17) therebetween.

The clamping ring 172 is integral with a support column 176 forming part of the scope body 171. A column slot 177 is formed in the support column 176, with the column slot 177 being contiguous with the slot 174 between the clamp arms 173a, b. As described in more detail herein, the slots 174 and 177 permit the clamp arms 173a, b to be compressed toward each other to thereby compress the clamping surface 175 of the ring 172 about the outer surface 23 of the cannula 20. In this manner, the fixture 170 can be affixed at a specific position on the cannula 20. It is understood that when the clamping ring 172 is loosened, the fixture 170 is free to rotate about the circumference of the cannula 20 in the direction of the arrow N. In addition, the fixture 170 can translate along the longitudinal length of the cannula 20 in the direction of the arrow T. Of course, the direction of the travel distance of the fixture 170 along the length of the cannula 20 is limited by the proximal end 22 and the bracket 27 used to engage a supporting flexible arm 160 as described above.

Returning to FIGS. 13–17, additional details of the fixture 170 can be discerned. In particular, the fixture 170 includes an optics mounting body 178 that is supported by and preferably integral with the support column 176. The optics mounting body 178 defines a stop edge 179 at the interface between the support column 176 and the mounting body 178. This stop edge defines the height of the support column from the clamping ring 172 to the stop edge 179. The stop edge 179 of the optics mounting body 178 can be used to limit the downward travel of the fixture 171 in the direction of the arrow T, which can be particularly important in embodiments of the cannula 20 that do not include the bracket 27.

Figure 15:
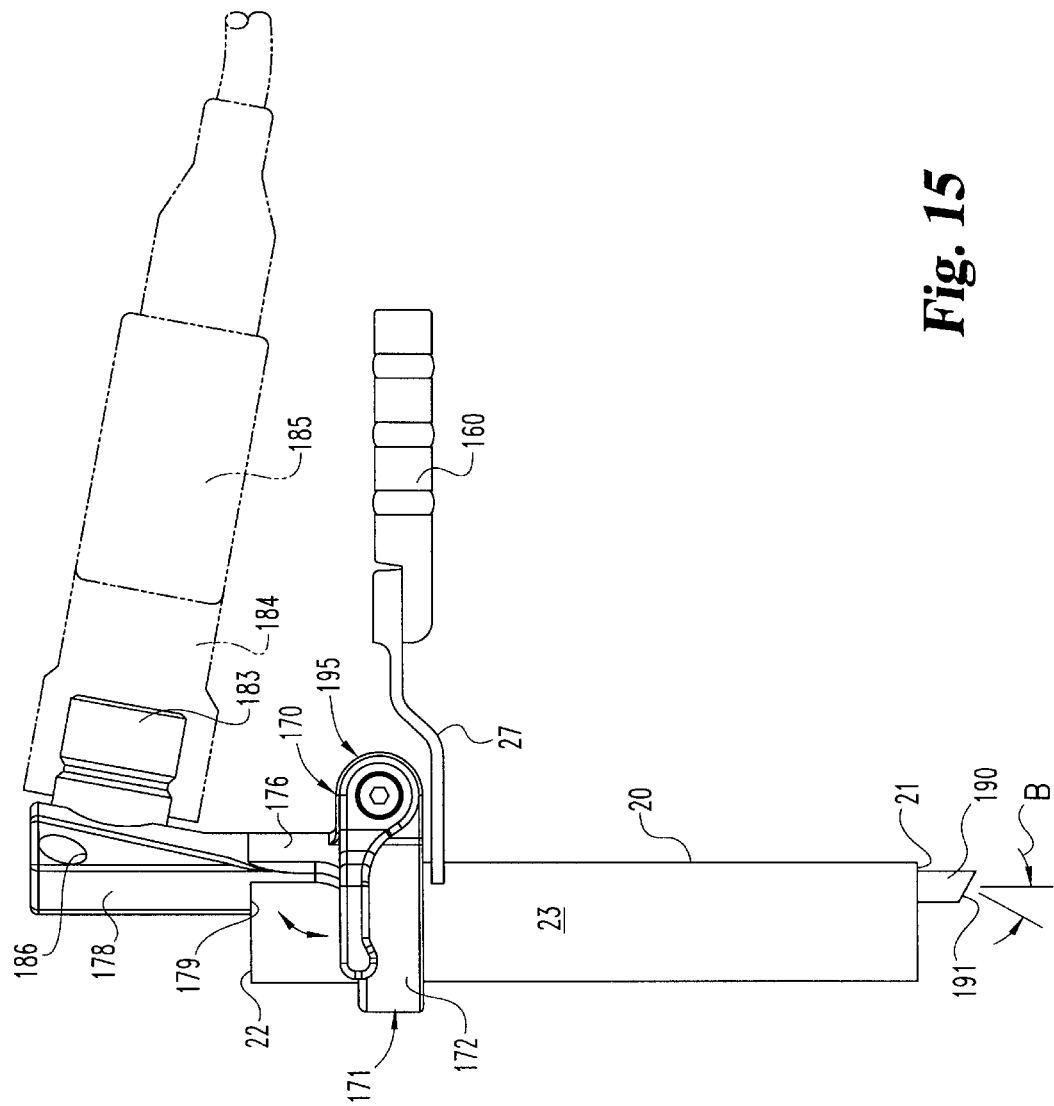
FIG. 15 is a side elevational view of the device depicted in FIG. 13 with the device shown connected to optical equipment depicted in phantom lines.

In accordance with the present embodiment, the optics mounting body 178 defines an optics bore 180 which is configured to receive and support an optics cannula 190. The optics bore 180 can communicate with an illumination port 181 which can receive an illumination source, such as a fiber optic light cable. The optics bore 180 also communicates with an optics coupling bore 182 projecting from a front face of the fixture 170. In accordance with one specific embodiment, the fixture 170 also includes a coupling body 183 that is preferably press-fit within the optics coupling bore 182. As shown in FIG. 15, the coupling body 183 can be engaged by a coupler 184 to support a camera 185 thereon.

Figure 23:
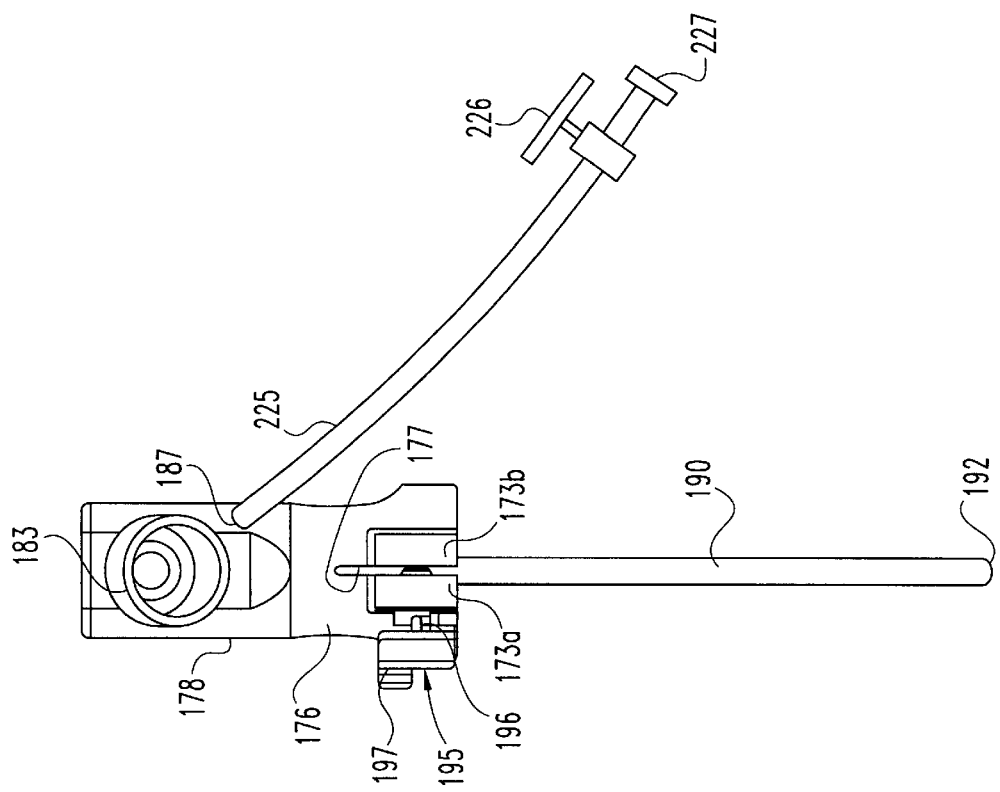
FIG. 23 is a side elevational view of a scope body as depicted in FIG. 14 connected to an aspiration circuit.
Figure 22:
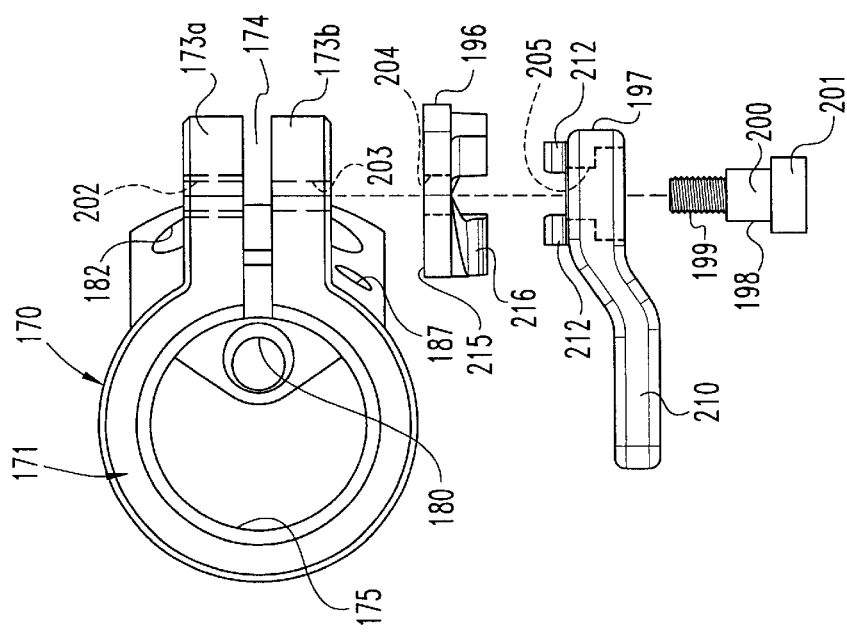
FIG. 22 is a bottom assembly view showing the assembly of the lever arm of FIGS. 18–19, the barrel cam of FIGS. 20–21 with the scope body shown in FIG. 14.

In a further aspect of the optics mounting body 178, an aspiration port 186 and an irrigation port 187 can be provided that communicates with the optics bore 180. Preferably, the optics cannula 190 includes channels along its length to correspond to the various ports in the optics mounting body 178. In one specific embodiment, the port 181 is not used, with the port 186 being used to receive an illumination element. As shown more particularly in FIG. 23, the port 187 can be connected to an aspiration circuit. In particular, the port 187 can be engaged to an aspiration tube 225 which carries a flow control valve 226 and Luer® fitting 227 at its free end. The Luer® fitting 227 can engage a source of irrigation fluid or aspiration vacuum pressure depending upon the particular use envisioned for the port 187 and a corresponding channel within the optics cannula 190.

In accordance with a method of the present invention, the port 187 is used as an aspiration port with the Luer® fitting 227 connected to a vacuum source. It is understood that the port 187 is in fluid communication with a corresponding channel in the optics cannula 190 so that suction applied through the tube 225 and port 187 is drawn through the distal or working end 192 of the optics cannula 190. The working end 192 is at the surgical site so that the suction draws air through the working channel 25 of the cannula 20, to the surgical site and through the aspiration/irrigation channel in the optics cannula 190. It has been found that providing aspiration suction in this manner eliminates smoke that may be developed during operation of certain instruments, such as a Bovie. Moreover, the suction applied through the port 187 can draw air across the lens 191 (see FIGS. 14, 15) of the optics cannula 190, to prevent fogging of the lens. If a separate aspiration tube is extended through the working channel, defogging of the lens 191 is best achieved with the opening of the aspiration tube adjacent the lens. In this manner, the provision of aspiration vacuum through the working channel and working space virtually eliminates the need to retract the optics cannula 190 to clean the lens 191. This is in contrast to prior devices in which either the lens had to be removed from the surgical site for cleaning or devices in which substantial flow of fluid is required to keep the lens clean and clear.

Looking now to FIGS. 18–22, details of a barrel clamp mechanism 195 are shown. The barrel clam mechanism 195 compresses the arms 173a, b of the clamping ring 172 together to clamp the fixture 170 to the cannula 20. The barrel clamp mechanism 195 includes a barrel cam 196 disposed immediately adjacent one of the clamp arms 173b, and a lever arm 197 that operates to compress the barrel cam 196 against the clamp arm 173. A shoulder screw 198 fixes each of these components together. Specifically, the shoulder screw 198 includes a threaded shank 199 that is configured to engage a mating threaded bore 202 in one of the clamp arms 173a. The shoulder screw 198 includes a bearing shank 200 that is smooth or non-threaded. The bearing shank 200 is received within a bearing bore 203 in the clamp arm 173b, a colinear bearing bore 204 in the barrel cam 196, and a bearing bore 205 in the lever arm 197. The shoulder screw 198 further includes an enlarged head 201 which is preferably received within a head recess 206 in the lever arm 197 (see FIG. 19). Preferably, the enlarged head 201 of the shoulder screw includes a driving tool recess to mate with a driving tool to thread the threaded shank 199 of the screw into the mating threaded bore 202 of the clamp arm 173a. It is understood that the barrel cam 196 and lever arm 197 are free to rotate about the bearing shank 200 of the shoulder screw 198.

Referring specifically to FIGS. 18–19, the lever arm 197 includes an arm 210 that is integral with a body 211. The bearing bore 205 and head recess 206 are defined in the body 211. The body 211 defines a pair of projections 212 on opposite sides of the bearing bore 205. As depicted in FIG. 19, each of the projections 212 includes a rounded tip 213 to provide a smooth sliding surface.

Referring specifically to FIGS. 20–21, the barrel cam 196 includes a flat face 215 that faces the clamp arm 173b. Preferably, the flat face provides for smooth rotation of the barrel cam 196 relative to the stationary arm 173b. The opposite face of the barrel cam 196 is a cam face 216 that includes a pair of diametrically opposite cam portions 217. In accordance with the preferred embodiment, the cam portions 217 define a ramp 218 that is inclined upward to a detent recess 219. Each detent recess 219 terminates in a stop 220 that is higher relative to the base detent recess 219 than the ramp 218.

In the assembled configuration, the barrel clamp mechanism 195 operates to compress the arms 173a, b of the clamping ring 172 together when the lever arm 197 is rotated about the shoulder screw 198. Specifically, as the lever arm 197 is rotated, the projections 212 slide on their rounded tip 213 along the ramps 218 until the rounded tips 213 fall within the opposite detents 219. As the projections 212 move up the ramps 218, the projections 212 push the barrel cam 196 toward the clamp arms 173a, b. More specifically, since the opposite clamp arm 173a is held relatively fixed by the threaded shank 199 of the shoulder screw 198, the movement of the barrel cam 196 presses the clamp arm 173b against the relatively stationary clamp arm 173a. As this occurs, the clamping ring 172 is tightened around the outer surface 23 of the cannula 20. When the projections 212 are seated within the recesses 219 of the barrel cam 196, the fixture is locked onto the cannula 20. It is understood that the recesses 219 are shallow enough to permit ready manual disengagement of the projections 212 from the recesses 219 as the lever arm 197 is rotated in the opposite direction.

In one specific embodiment, the detent recesses 219 are 180° opposite each other. The ramps 218 are curved and subtend an angle of about 90°. Thus, the lever arm 197 rotates through 90° to move the projections 212 from one end of the cam ramps 218 to the recesses 219. In the preferred embodiment, the lever arm ninety degree movement (arrow J in FIG. 15) moves the arm from a first position in which the arm 197 is substantially parallel to the cannula, to a second position in which the arm is substantially perpendicular to the cannula. Most preferably, in the second position the arm is oriented immediately adjacent the cannula, rather than projecting away. In the first and second positions, the lever arm 197 maintains a low profile so as not to interfere with the surgeon's manipulation of tools and instruments through the working channel. In a specific embodiment, the first position of the lever arm corresponds to the loose or unlocked position of the barrel clamp mechanism 195, while the second position corresponds to the locked configuration.

In order for the barrel clamp mechanism 195 to function properly, it is preferred that the barrel cam 196 remain stationary relative to the moveable lever arm 197, with the exception that the barrel cam 196 is free to translate along the length of the shoulder screw 198. Consequently, the clamp arm 173b includes a recess 222 that has a configuration substantially similar to the outer periphery of the barrel cam 196. In this manner, the barrel cam can be slightly indented within the clamp arm 173b so that the cam is unable to rotate about the shoulder screw 198 as the lever arm 197 is pivoted.

In accordance with one specific embodiment of the invention, the components of the fixture 170 are formed of a flexible and resilient material. For example, the scope body 171 can be formed of a plastic, such as polycarbonate. The scope body 171 lends itself particularly well to typical plastic molding techniques. Likewise, the barrel cam 196 and lever arm 197 can be molded from a plastic material. In one specific embodiment, these components are formed of Delrin®, since Delrin® provides a smooth surface for the relative movement between the projection 212 on the lever arm 197 and the cam face 216 of the barrel cam 196.

It is understood that the travel of the barrel clamp mechanism 195 can be calibrated sufficient to tightly compress the clamping rings 172 about the cannula 20. It is also understood that this compression must not be so great as to compromise the integrity or strength of the cannula 20. In one specific embodiment, the slot 174 is larger than the maximum travel of the barrel clamp mechanism 195 so that the projections 212 of the lever arm 197 can rest solidly within the detent recesses 219 of the barrel cam 196. In accordance with one specific embodiment, the slot 174 has a dimension of 2.0 mm while the throw of the barrel clamp mechanism 195 achieved by the barrel cam 196 is 1.0 mm.

In accordance with the present embodiment of the invention, the fixture 170 supports an optics cannula 190 in a fixed orientation relative to the scope body 171. In other words, in this specific embodiment, the optics cannula 190 is not permitted to rotate about its axis as could the scope 50 of the embodiment shown in FIG. 1. The lens 191 is therefore mounted at an angle B relative to the distal end of the optics cannula 190. In one specific embodiment, the lens 191 is situated at an angle B of 30°. In addition, in the specific embodiment, the lens has an optical axis that is angled toward the center of the working space 25 or the cannula 20. While the lens 191 has a fixed orientation relative to the scope body 171, the lens can still be rotated around the working space by rotation of the fixture 170 about the outer surface 23 of the cannula 20. In addition, the lens 191 and the optical system provide a depth of field of view that allows the surgeon to view anatomy outside the working channel 25.

Even in the present specific embodiments, the fixture 170 allows rotation of the optics cannula 190 around the working space and translation of the optics cannula 190 and 191 along the longitudinal axis of the working channel 25. Of course, it is understood that the surgeon can achieve these motions by releasing the barrel clamp mechanism 195 and then re-engaging the clamp by rotating the lever arm 197 to its locked position. Preferably, the optics cannula 19 is sized so that the lens 191 can project beyond the distal end 21 of the cannula 20. Similarly, in the preferred embodiment, the fixture 170 allows the retraction of the lens 191 and optics cannula 190 within the working channel 25 and cannula 20.

In one specific embodiment, the fixture 170 permits up to 15 mm travel along the direction of the arrow T with 7.5 mm of the travel being within the working space 25 and 7.5 mm of the travel being beyond the distal end 21 of the cannula 20. In accordance with the specific embodiment, this 15 mm travel distance is related to the height of the support column 176 from the top of the clamping ring 172 to the stop edge 179 of the optics mounting body 178. The amount of extension of the lens 191 of the optics cannula 190 beyond the distal end 21 of the cannula 20 is also based upon the overall length of the optics cannula 190 relative to the overall length of the working channel cannula 20. In one specific embodiment, the optics cannula 190 has a length of 100 mm measured from the lens 191 to the stop edge 179 of the optics mounting bore 178. Of course, it is understood that the optics cannula is longer than this 100 mm distance because a portion of the cannula is supported within the optics bore 180 of the optics mounting body 178. Again in the specific embodiment, the cannula 20 has an overall length of 92 mm from its distal end 21 to its proximal end 22 (see FIG. 15).

In a further aspect of the invention, the overall length of the cannula, and consequently the optics cannula 190, is determined, in part, by the spinal anatomy. In particular, for applications of the present invention in the field of spinal surgery, it has been found that placement of the proximal end 22 of the working channel 25 too distant from the surgical site at the distal end 21 causes the surgeon to lose tactile feel while manipulating certain instruments. In other words, when the surgeon passes instruments through the working channel and manipulates them at the surgical site, a certain amount of "feel" is required so that the surgeon can accurately perform the respective operations with the instrument. If the distance between the surgical site and manual end of the instrument is too great, the surgeon will not be able to stably and comfortably operate the instrument.

Figure 24:
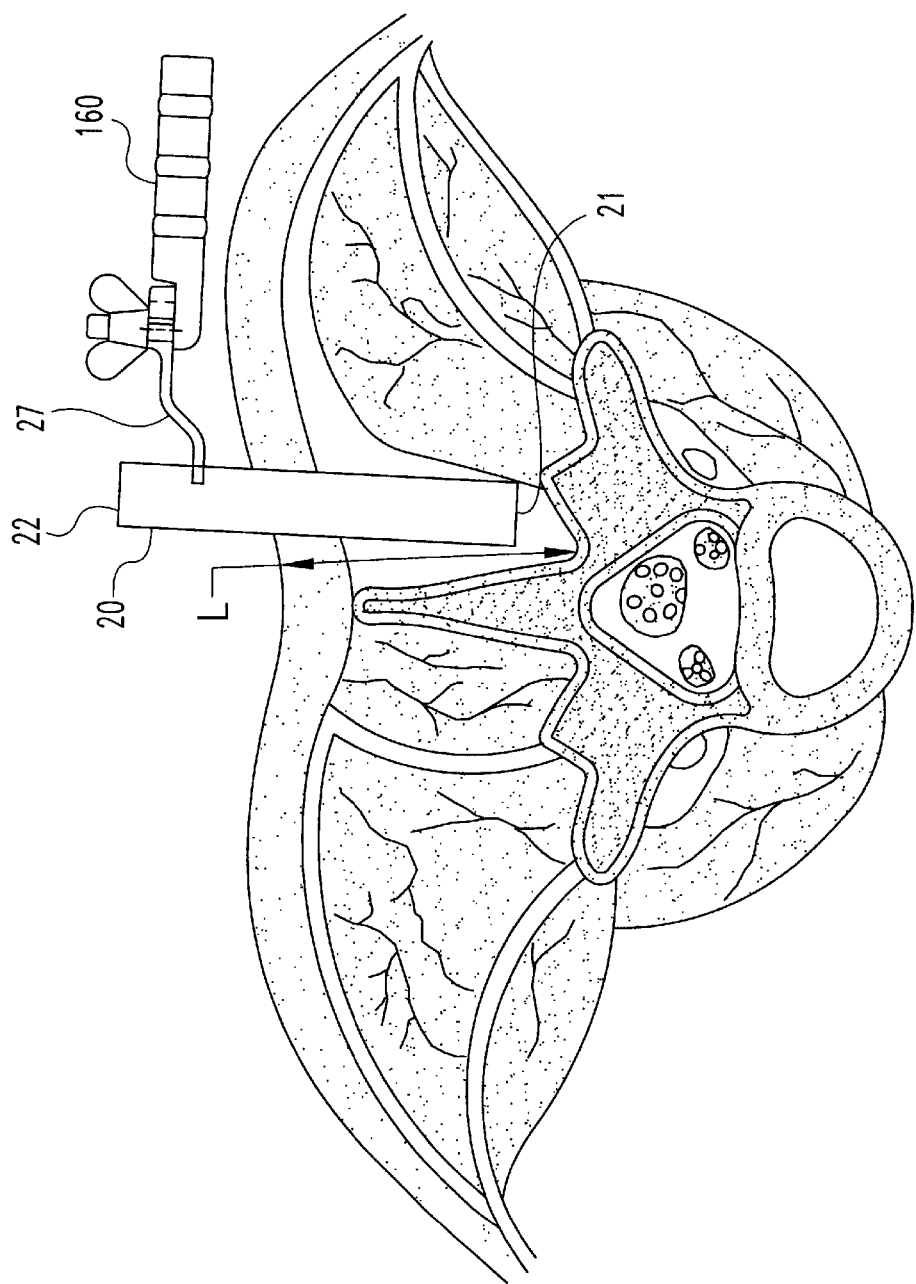
FIG. 24 is a cross-sectional view of a human patient at a lumbar vertebral level with a device according to one embodiment of the invention situated within the patient to define a working channel above the laminae of the vertebra.

In accordance one beneficial aspect of the present invention, it has been found that the working channel cannula 20 must have a length that is limited relative to the distance L (FIG. 24) between the vertebral laminae and the surface of the skin. In the lumbar region of the spine, this distance is approximately 65–75 mm. Consequently, in one embodiment of the invention, the working channel cannula 20 has first portion of its length somewhat less than the anatomic distance. In one specific embodiment, this length of the first portion is about 66 mm from the distal end 21 to the mounting bracket 27. In some surgical applications, the mounting bracket 27 may actually rest against the skin of the patient so that the distal end 21 of the working channel cannula can be closer to the surgical site.

Further in accordance with the present invention, the remaining second portion of the length of the cannula 20 above the mounting bracket 27 is minimized. In accordance with the invention, this distance must be sufficient to permit extension and retraction of the lens 191 relative to the distal end 21 of the cannula 20. As described above, the travel of the optical lens 191 is preferably 15 mm, so that the remaining length of the cannula 20 is about 26 mm to accommodate this travel and to provide adequate surface for engagement by the clamping rings 172. Thus, in the preferred embodiment, the working channel cannula 20 has an overall length of 92 mm. In accordance with one aspect of the invention, it has been found that the relative length between the first portion of the cannula disposed within the patient to the second portion of the cannula length situated outside the patient have a ratio of 2:1 to 3:1. In other words, the length of the first portion is between two to three times longer than the length of the second portion.

It has also been found that it is desirable to minimize the height of the fixture 170 beyond the end of the working channel cannula 20. In accordance with the present invention, the optics mounting body 178 has a height of about 21 mm between the stop edge 179 and the top face of the body 178. This distance is not so great that the surgeon has restrained from manipulating instruments directly above the fixture 170. Of course, it is preferable that the surgeon manipulate the instruments directly above the proximal end 22 of the working channel 20 immediately adjacent to the fixture 170.

In the present preferred embodiment, the working channel cannula has an inner diameter of about 15 mm and an outer diameter of about 16 mm. Alternatively, the cannula can be provided in a smaller size for other regions of the spine. In a further specific embodiment, the cannula inner diameter is 12.7 mm with a 14 mm outer diameter. In another aspect of the invention, the overall length and diameter of the working channel cannula 20 is calibrated again relative to the distance L of the spinal anatomy. With the larger diameter working channel, the surgeon can orient certain instruments at an angle relative to the longitudinal axis of the cannula 20. In specific embodiments, this angle is approximately 5–6°. It has been found that this angle, together with the large working channel 25, gives the surgeon greater flexibility and mobility within the surgical site to perform various operations. To that end, the length and diameter of the working channel cannula 20 is appropriately sized to maintain this flexibility, without getting too large. A working channel cannula 20 that has too large a diameter is less adaptable to the spinal anatomy.

In accordance with preferred methods using the devices of the present invention, the working space is generally limited to the region directly adjacent the laminae of a vertebra. A cannula having a diameter that is too large will interfere with the spinous process when the working space is created, and will require resection of greater amounts of tissue than is preferred for an optimal percutaneous procedure. Therefore, in accordance with one aspect of the invention, the working channel cannula has a relationship between its length and its diameter to permit tool angles through the cannula of between 5–8°. In accordance with one specific aspect of the present invention, the cannula can have a length to diameter ratio of between about 5.5:1 to 7:1. Further in accordance with the present invention, the working channel cannula has a length that is no more than 20–30 mm greater than the distance L (FIG. 24) between the laminae and the skin of the patient.

One important feature of the present invention is achieved by the large diameter of the working channel 25 in the cannula 20. This large diameter allows the surgeon or surgeons conducting the surgical procedure to introduce a plurality of instruments or tools into the working space. For example, as described above, a tissue retractor and discectomy instruments can be simultaneously extended through the working channel. In the illustrated embodiment, the discectomy instruments could include a trephine for boring a hole through the disc annulus and a powered tissue cutter for excising the herniated disc nucleus. Likewise, the present invention contemplates the simultaneous introduction of other types of instruments or tools as may be dictated by the particular surgical procedure to be performed. For example, an appropriately sized curette and a rongeur may be simultaneously extended through the working channel into the working space. Since all operations being conducted in the working space are under direct visualization through the viewing element, the surgeon can readily manipulate each of the instruments to perform tissue removal and bone cutting operations, without having to remove one tool and insert the other. In addition, since the surgical procedures can be conducted without the necessity of irrigation fluid, the surgeon has a clear view through the working space of the target tissue. Furthermore, aspects of the invention which permit a wide range of motion to the viewing element allow the surgeon to clearly visualize the target tissue and clearly observe the surgical procedures being conducted in the working space.

The surgeon can capitalize on the same advantages in conducting a wide range of procedures at a wide range of locations in the human body. For example, facetectomies could be conducted through the working channel by simply orienting the working channel cannula 20 over the particular facet joints. The insertion of vertebral fixation elements can also be accomplished through the devices. In this type of procedure, an incision can be made in the skin posterior to the location of the vertebra at which the fixation element is to be implanted. Implementing the steps shown in FIG. 10, the cannula 20 can be positioned through the incision and tissue directly above the particular location on the vertebra to be instrumented. With the optics extending through the working channel, an insertion tool holding the vertebral fixation element can be projected through the cannula 20 and manipulated at the vertebra. In one specific embodiment, the fixation element can be a bone screw. The working channel 25 has a diameter that is large enough to accept most bone screws and their associated insertion tools. In many instances, the location of the bone screw within the vertebra is critical, so identification of the position of the cannula 20 over the bony site is necessary. As mentioned above, this position can be verified fluoroscopically or using stereotactic technology.

In many prior procedures, cannulated bone screws are driven into the vertebra along K-wires. The present invention eliminates the need for the K-wire and for a cannulated screw. The working channel itself can effectively operate as a positioning guide, once the cannula 20 is properly oriented with respect to the vertebra. Moreover, the devices allow insertion of the bone screw into the vertebra to be conducted under direct vision. The surgeon can then readily verify that the screw is passing into the vertebra properly. This can be particularly important for bone screws being threaded into the pedicle of a vertebra. The working channel cannula 20 can be used to directly insert a self-tapping bone screw into the pedicle, or can accept a variety of tools to prepare a threaded bore within the pedicle to receive a bone screw.

The devices can also be used to prepare a site for fusion of two adjacent vertebrae, and for implantation of a fusion device or material. For example, in one surgical technique, an incision can be made in the skin posterior to a particular disc space to be fused. The incision can be made anteriorly, posteriorly or posterior laterally. If the incision is made anteriorly for anterior insertion of the working channel, it is anticipated that care will be taken to retract tissues, muscle and organs that may follow the path of the incision to the disc space. However, the devices of the present invention allow this tissue retraction to occur under direct vision so that the surgeon can easily and accurately guide the cannula 20 to the disc space without fear of injury to the surrounding tissue. As the tissue beneath the skin is successively excised or retracted, the working channel cannula 20 can be progressively advanced toward the anticipated working space adjacent the vertebral disc. Again under direct vision, the disc space can be prepared for implantation of fusion materials or a fusion device. Typically, this preparation includes preparing an opening in the disc annulus, and excising all or part of the disc nucleus through this opening.

In subsequent steps, a bore is cut through the disc annulus and into the endplates of the adjacent vertebrae. A fusion device, such as a bone dowel, a push-in implant or a threaded implant can then be advanced through the working channel of the cannula 20 and into the prepared bore at the subject disc space. In some instances, the preparatory steps involve preparing the vertebral endplates by reducing the endplates to bleeding bone. In this instance, some aspiration and irrigation may be beneficial. All of these procedures can be conducted by tools and instruments extending through the working channel cannula 20 and under direct vision from the viewing element.

In some instances, graft material is simply placed within the prepared bore. This graft material can also be passed through the working channel cannula 20 into the disc space location. In other procedures, graft material or bone chips are positioned across posterior aspects of the spine. Again, this procedure can be conducted through the working channel cannula particularly given the capability of the cannula to be moved to different angles from a single incision site in the skin.

The present invention provides instruments and techniques for conducting a variety of surgical procedures. In the illustrated embodiments, these procedures are conducted on the spine. However, the same devices and techniques can be used at other places in the body. For example, an appropriately sized working channel device 10 can be used to remove lesions in the brain. The present invention has particular value for percutaneous procedures where minimal invasion into the patient is desirable and where accurate manipulation of tools and instruments at the surgical site is required. While the preferred embodiments illustrated above concern spinal procedures, the present invention and techniques can be used throughout the body, such as in the cranial cavity, the pituitary regions, the gastro-intestinal tract, etc. The ability to reposition the viewing optics as required to visualize the surgical site allows for much greater accuracy and control of the surgical procedure. The present invention allows the use of but a single entry into the patient which greatly reduces the risk associated with open surgery or multiple invasions through the patient's skin.

In accordance with yet another aspect of the present invention, a tissue retractor apparatus 230 is provided that combines a tissue retractor 231 with an optical viewing device 232. Referring to FIGS. 25–26, the retractor apparatus 230 includes a retractor plate 234 that is affixed to a grip 235 for manual support of manipulation of the retractor. The grip 235 is at the proximal end 236 of the plate. The distal end 237 of the retractor plate preferably has a blunt tip 238 to avoid trauma upon insertion and manipulation of the tissue retractor. Preferably, the blunt tip 238 is angled slightly away from the plate 234. The retractor plate 234 defines an outer retraction surface 239 that can be configured according to the type of surgery being performed. In a preferred embodiment, the plate 234 is semi-cylindrical in configuration to permit atraumatic retraction of tissue adjacent a surgical site. In addition, the retractor plate 234 defines a channel 240 that helps define a working channel. As thus far described, the retractor 231 is substantially similar to the retractor 70 depicted in FIGS. 4–6 and as described above.

In accordance with this embodiment of the invention, an optical viewing device 232 is supported within the retractor 231 by way of a number of C-clips 245. Preferably, the C-clips 245 are formed of a resilient material, such as plastic or thin flexible metal, and are affixed to the channel 240 of the retractor plate 234. In accordance with one specific embodiment, two such C-clips 245 are provided to stably mount the optical viewing device 232 relative to the retractor 231. Preferably, the clips 245 are sized to support an optical viewing device 232 that is configured substantially identical to the viewing device 50 described above. In the preferred embodiment, the viewing device 232 has a distal tip 52 with an angled lens 54. In accordance with this embodiment, the C-clips 245 provide a resilient friction fit to the optical viewing device 232 while still permitting relative sliding and rotation of the viewing device 232 relative to the retractor 231.

In accordance with the present invention, the tissue retractor apparatus 230 can be used in a variety of applications, including non-spinal applications. For example, this tissue retractor can have application in transnasal and transphenoidal surgeries, and in pituitary procedures. In surgeries of this type, it is not necessarily desirable to provide a closed cannula, such as a working channel cannula 20. Moreover, the smaller working space does not lend itself to the use of a closed cannula which would tend to restrict the space available for manipulation of surgical instruments. Consequently, a tissue retractor or speculum of the type shown in FIGS. 25–26 may be very adequate for surgeries of this type. In this instance, then the working channel is defined in part by the patient's body itself, and in part by the tissue retractor. The optical viewing device 232 is supported relative to the retractor to permit the same degrees of motion as are available with the device 10 described above.

Figure 27:
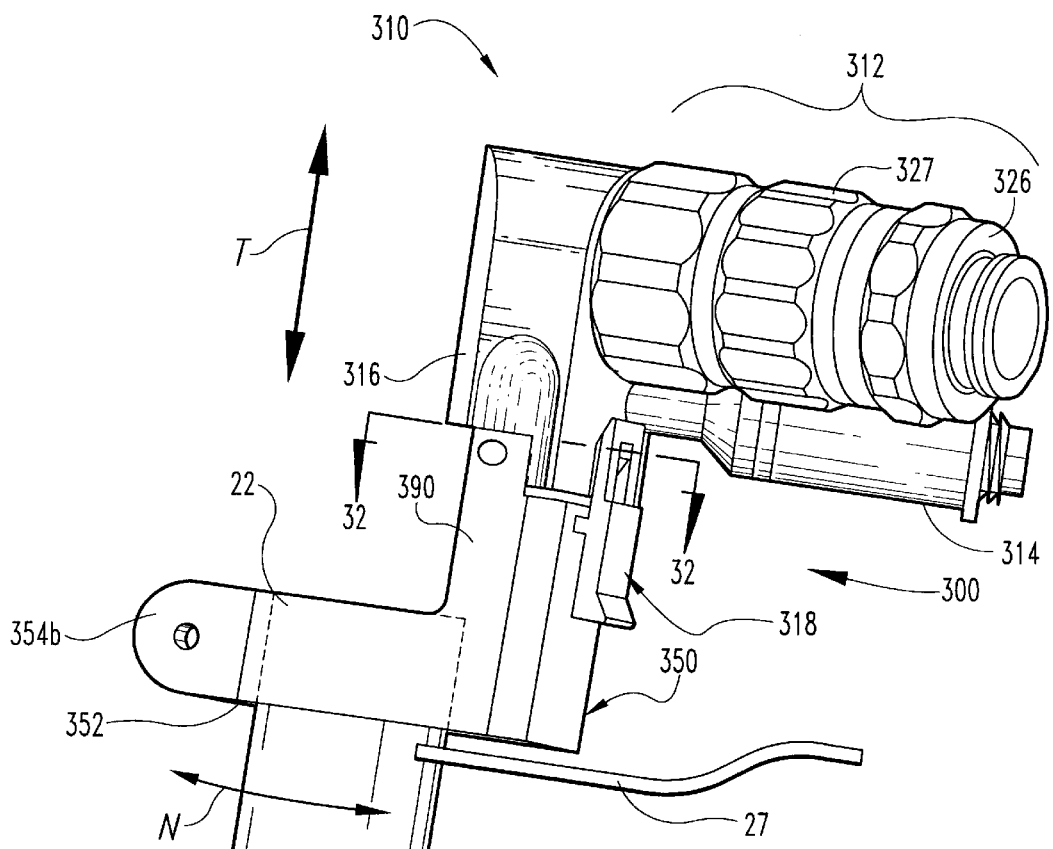
FIG. 27 is a side perspective view of a device according to another embodiment of the present invention.

In another embodiment of the invention and referring to FIG. 27, a modular clamp assembly 300 for supporting viewing optics and/or irrigation/aspiration components is provided with the cannula 20. This embodiment is mounted on a cannula 20 having features similar to those previously described, and similar features are referenced by the same numerals. In accordance with this embodiment, the assembly 300 is provided with a viewing element 310 and a clamp assembly 350, which are shown most clearly in FIGS. 28, 29, and 30. The viewing element 310 includes a viewing portion 312 and an illumination element 314 coupled to a body portion 316. As shown more clearly in FIG. 28, body portion 316 has an optics cannula 320 and dovetail 330 extending therefrom towards the cannula 20 when placed thereon. Preferably, dovetail 330 is integrally formed with the body portion 316. When engaged to the cannula 20, optics cannula 320 extends from a proximal end 22 of cannula 20 to distal working end 21, as shown in FIG. 27.

Figure 27A:
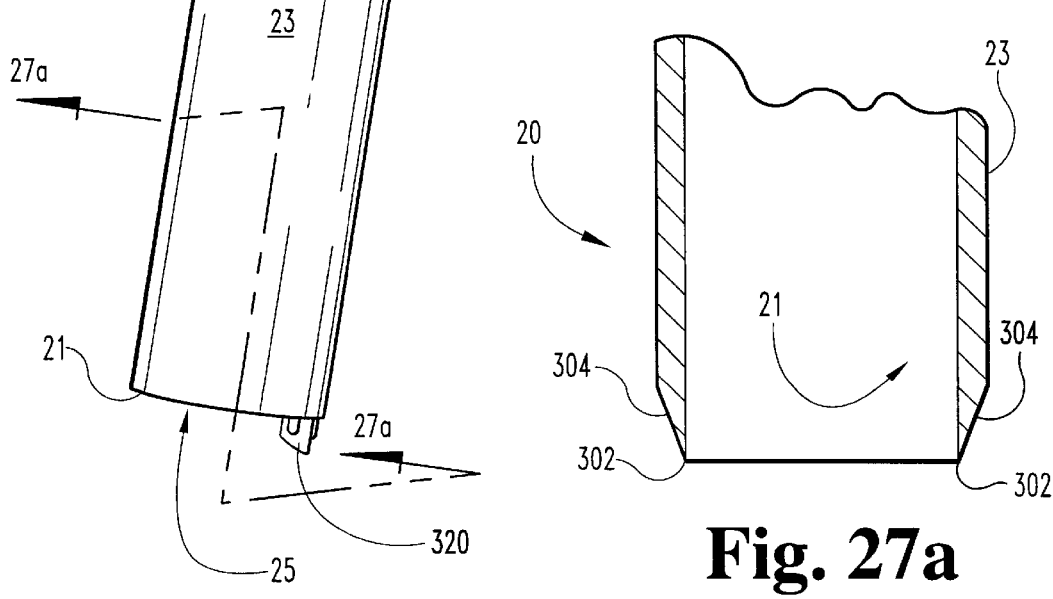
FIG. 27a is a section view along line 27a—27a of FIG. 27.

In the embodiment of the present invention, illustrated in FIG. 27a, the distal working end 21 is beveled and includes a cutting edge 302 for penetrating bone and soft tissue. A sloped retraction surface 304 extends from edge 302 to outer surface 23 of cannula 20. Retraction surface 304 acts to gradually separate tissue while minimizing damage thereto as the cannula is advanced to the desired depth at the surgical site.

Body portion 316 defines an optics bore (not shown) for receiving and supporting optics cannula 320, and to provide visual communication to viewing portion 312. In one embodiment, the optics bore communicates with illumination element 314, which is configured to communicate with an illumination source. In a preferred embodiment, components of the viewing portion 312, such as the eyepiece component 326 and focus adjustment knob 327, are integrally formed with the body portion 316. In an alternate embodiment, the viewing portion 312 is threadingly coupled to body portion 316.

Referring now to the clamp assembly 350, there is included a clamp ring 352 and a viewing element receiving portion 390 extending from clamp ring 352. Receiving portion 390 defines a dovetail receptacle 396 for receiving an insertion end 332 of dovetail 330 in sliding engagement. It should be understood that the receptacle 396 may alternately be defined by body portion 316 of viewing element 310, and dovetail 330 may extend from receiving portion 390 to engage the receptacle 396.

Clamp ring 352 substantially encircles an outer surface 23 of cannula 20. In particular, clamp ring 352 includes a clamping surface 356 (see FIG. 28). In a preferred embodiment, clamping surface 356 has substantially the same configuration and dimension as outer surface 23 of cannula 20. The clamping ring 352 includes clamping arms 354a and 354b at the free ends of the ring 352. The clamping arms 354a and 354b define a slot 358 therebetween. As described below in more detail, the slot 358 permits arms 354a and 354b to be compressed toward each other to thereby compress clamping surface 356 of the ring 352 about the outer surface 23 of the cannula. It is understood that when clamping ring 352 is loosened, the clamp assembly 350, and if engaged thereto, the viewing element 310 are free to rotate about the circumference of the cannula 20 in the direction of arrow N. Additionally, the clamp assembly 350 can translate along the longitudinal length of the cannula 20 in the direction of the arrow T. The length of travel is limited by the bracket 27 used to engage the flexible support arm 160 as described previously.

Extending from and integrally formed with clamp ring 352 is receiving portion 390. In a preferred embodiment, receiving portion 390 includes a surface 392 that abuttingly engages a stop surface 328 of body portion 316 when dovetail 330 is fully received within receptacle 396. In one embodiment, stop surface 328 of the viewing element 310 limits the downward travel of the assembly 300 along the cannula 20 by engaging proximal end 22 of cannula 20.

In a further aspect of the clamp assembly 350, an irrigation port 393, shown in FIG. 29, can be provided through receiving portion 390 to allow connection of irrigation cannula 324 to an irrigation tube 225b via irrigation port 393. Luer® lock fitting 227b couples tube 225b to an irrigation source (not shown). An aspiration port 392 may also be provided through clamp assembly 350 to allow connection of aspiration cannula 322 to an aspiration tube 225a through aspiration port 392. Luer® lock fitting 227a couples tube 225a to an aspiration source (not shown). It should be understood that the clamp assembly 350 may be provide with both an irrigation cannula 324 and an aspiration cannula 322 with corresponding ports 393 and 392 through receiving portion 390. In one embodiment, only one of the irrigation/aspiration cannulas and its corresponding port is provided. In another embodiment, no irrigation or aspiration cannulas or ports are provided. In yet another embodiment, a single irrigation/aspiration cannula and port is provided and irrigation and aspiration is performed alternately through the single tube and port. It should be understood that the irrigation/aspiration cannula(s) may be used according to the methods described above.

Figure 31:
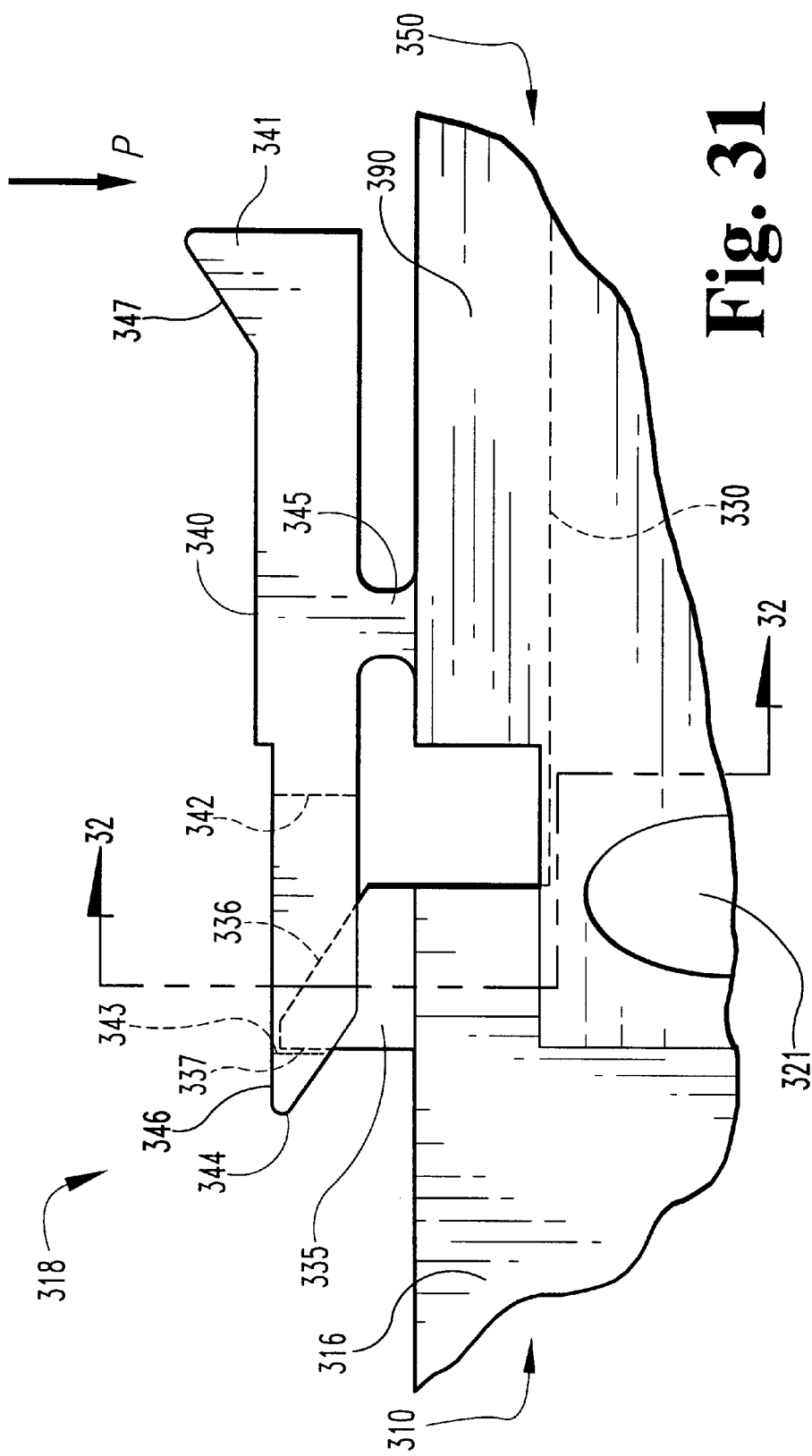
FIG. 31 is a side elevational view of a coupling mechanism forming a part of the assembly of FIG. 28.

Clamp assembly 350 and viewing element 310 are releasably engaged via connection assembly 318. Connection assembly 318 is shown to be preferably positioned on clamp assembly 350; however, it should be understood that in alternate embodiments connection assembly 318 may be provided on viewing element 310. Referring now to FIG. 31, connection assembly 318 includes a clip 340 pivotably mounted to viewing element receiving portion 390 of clamp assembly 350 via resilient hinges 345. In the illustrated embodiment, clip 340 is mounted via two resilient hinges 345. In an alternate embodiment, only one hinge 345 is used to mount clip 340.

Resilient hinge 345 biases clip 340 to a position, as shown in FIG. 31, where the body of clip 340 is substantially parallel to body portion 316 and receiving portion 390. A protuberance 335 projects from and is preferably integrally formed with body portion 316 of viewing element 310. Clip 340 defines an aperture 342, 343 configured and positioned to receive protuberance 335 when dovetail 330 is fully received within receptacle 396, placing the viewing element 310 and the clamp assembly 350 in an assembled position (as shown in FIG. 27.) In the assembled position, stop surface 328 is proximate engagement surface 392. In one embodiment, stop surface 328 engages engagement surface 392. In another embodiment, a space is left between stop surface 328 and engagement surface 392 when the viewing element 310 is coupled to clamp assembly 350.

Figure 28:
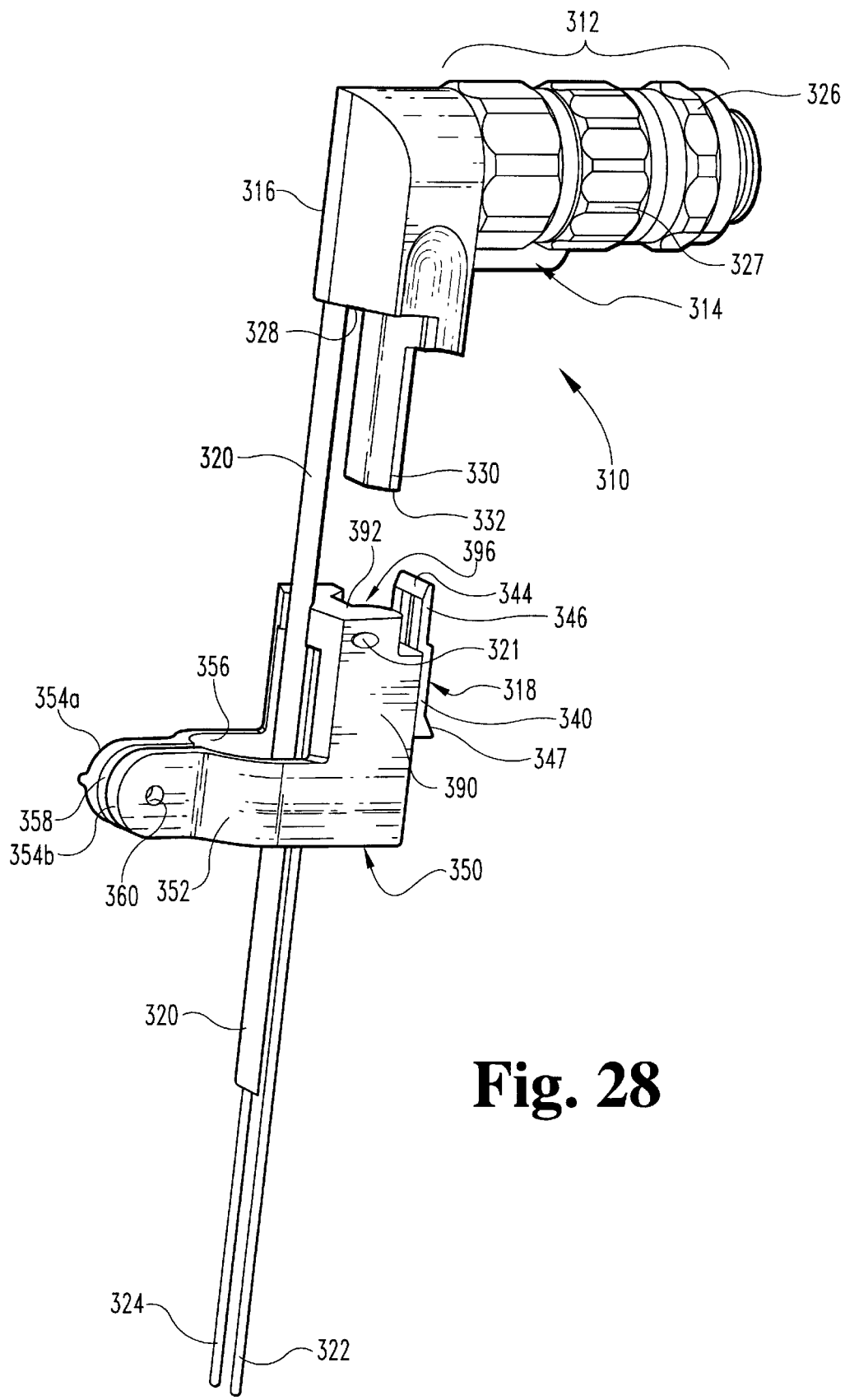
FIG. 28 is a side perspective view of a modular clamp and endoscope assembly forming part of the device of FIG. 27.

Clip 340 has a first end 346 defining a nose portion 344 extending toward viewing element 310 when it and clamp assembly 350 are positioned as shown in FIG. 28. Protuberance 335 defines an inclined surface 336 that opposes nose portion 344. Nose portion 344 slidingly engages the inclined surface 336 as dovetail 330 is placed in receptacle 396. This protuberance acts as a cam to rotate the nose portion 344 as it moves along inclined surface 336, causing the clip 340 to rotate in a direction indicated by arrow P. As the dovetail 330 is further positioned within receptacle 396, the wall 343 of aperture 342, 343 eventually communicates with engagement surface 337 of protuberance 335. Hinge 345 then biases the clip 340 to the position shown in FIG. 31, where the engagement surface 337 engages an endwall 343 that defines a portion of the aperture 342, 343.

Once coupled the viewing element 310 and clamp assembly 350 are effectively held in such position by the clip 340. In order to uncouple the scope/clamp assembly, clip 340 is rotated by depressing second end 347 via handle portion 341 in the direction of arrow "P" to rotate the clip 340 about hinge 345. Nose portion 344 is thus rotated in the direction opposite arrow P until endwall 343 no longer engages engagement surface 337. The viewing element 310 may then be removed from the clamp assembly 350 by sliding dovetail 330 out of the receptacle 396.

It should be understood that the present invention contemplates other structures for coupling viewing element 310 to clamp assembly 350. For example (by way of illustration and not limitation), dovetail 330 may be replaced by one or more guide pins extending from viewing element 330 to be received within corresponding slots on receiving portion 390. Alternatively, the clip 340 may be provided on one or both of the side portions of the receiving portion 390.

Figure 32:
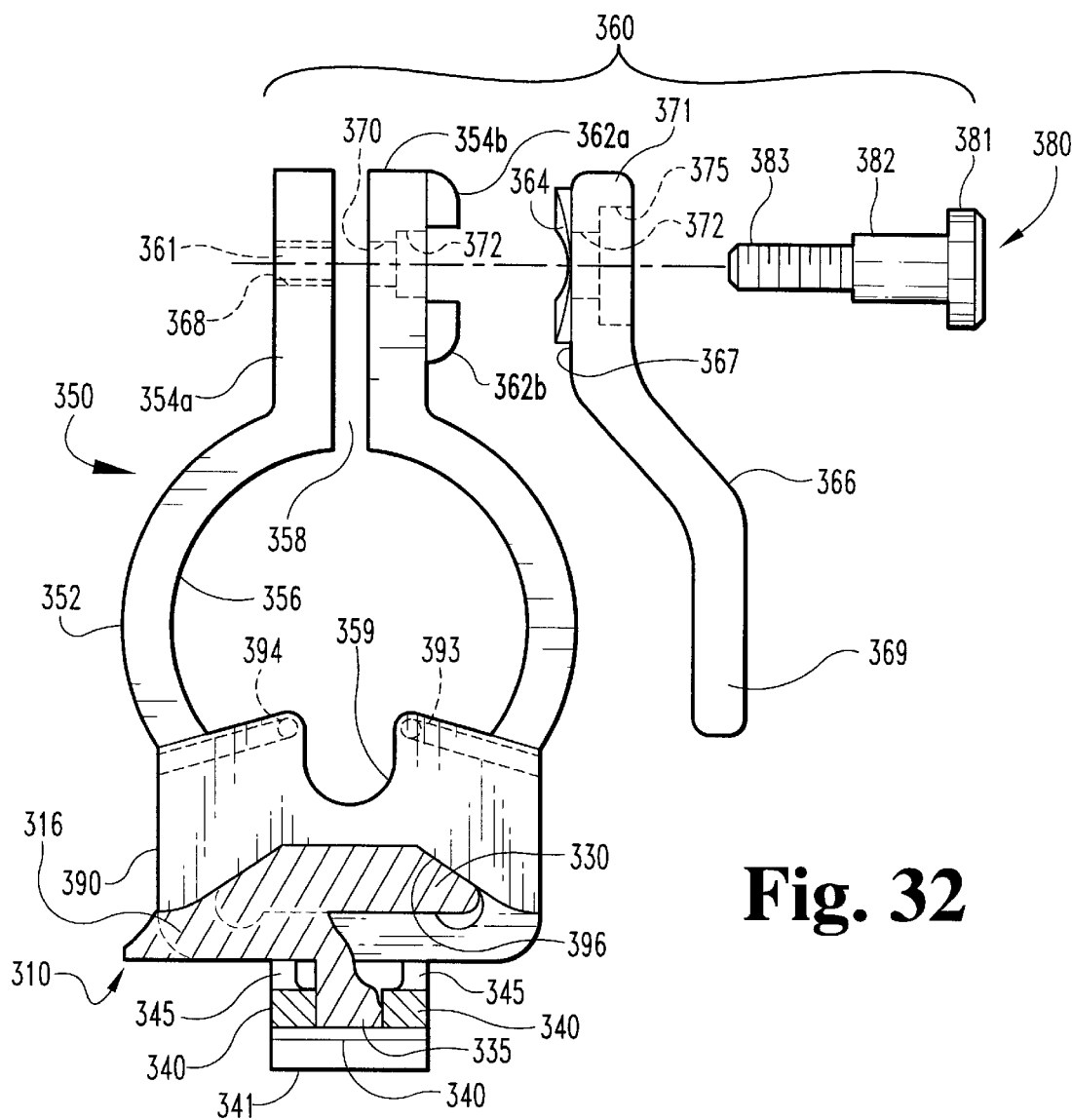
FIG. 32 is a partially fragmented cross-sectional view of the device taken along line 32—32 of FIG. 27.

With reference now to FIG. 32, there is illustrated a plan view of clamp assembly 350 and a portion of a section through viewing element 310. Clamp assembly 350 is shown removed from cannula 20 for clarity. Dovetail 330 is shown positioned within receptacle 396, and protuberance 335 is received within the aperture 342, 343 of clip 340. Receiving portion 390 further defines an optics recess 359 for receiving optics cannula 320 between irrigation port 393 and aspiration port 394. Optics recess 359 allows placement of the optics cannula 320 adjacent the working channel 25 of the cannula 20.

The clamp assembly 350 may be loosened and rotated or translated about the cannula 20 via the lever arm assembly 360, shown in exploded view in FIG. 32. Lever arm assembly 360 includes fastener 380 coupling a lever arm 366 to clamping arms 354a and 354b. Fastener 380 includes an enlarged head 381, a shank portion 382 integrally formed therewith and extending therefrom. Shank portion 382 defines a threaded portion 383 remote from the head 381.

Lever arm 366 has a first end 369 and a second end 371. In proximate second end 371 there is a portion of a bearing bore through lever arm 366 which has a shank receiving portion 372 and a colinear head receiving portion 375. Lever arm 366 also includes an inside face 367 adjacent arm 354b. Projecting from face 367 and integrally formed therewith is cam portion 364. Referring to FIG. 33, cam portion 364 has one or more arcuate inclined ramps 377a, 377b, 377c, 377d, collectively designated as ramps 377. Each ramp 377 is inclined upward from a low portion 378 to a high portion 379. Between low portions 378 and high portions 379 of adjacent ramps 377 are detents 374.

Referring back to FIG. 32, clamping arms 354a and 354b have a bore 361 which includes a threaded portion 368 in arm 354a, and the other portion of the bearing bore having a bearing portion 370 and a colinear shank receiving portion 372 in arm 354b. Arm 354b also includes projections 362a and 362b extending therefrom and integrally formed therewith. Projections 362a and 362b are configured to releasably engage and be received within a corresponding one of the detents 374.

When lever arm assembly 360 is assembled, threaded portion 383 of fastener 380 threadingly engages clamp arm 354a to secure lever arm 366 thereto. Shank portion 382 is rotatably received within shank receiving portions 372, and head 381 is received within head receiving portion 375. By rotating lever arm 366 about shank 382 of fastener 380, lever arm 366 is operable to selectively compress or release arms 354a and 354b to allow clamping surface 356 to engage outer surface 23 of cannula 20. Thus rotation of the assembly 300 is accomplished in the N direction or translation in the T direction (FIG. 27) along cannula 20 by releasing clamping ring 352. In order to release clamp ring 352, lever arm 366 is positioned so that projections 362 releasably engage a corresponding one of detents 374 adjacent low portions 378. It is understood that the detents 374 are configured to allow disengagement of projections 362 by a reasonable force applied to first end 369 of lever arm 366. Once clamp ring 352 is in the desired position, the lever arm 366 is rotated so that the projections slide up corresponding ones of the ramps 377 until the projection falls into a detent between the high portions 379 of adjacent ramps 377, thus compressing and then holding clamp ring 352 about the outer surface 23 of the cannula 20.

FIG. 34 illustrates an alternate configuration cam 364' of lever arm 366. In this embodiment, there is provided two ramps 377a and 377b. Adjacent high portions 379a, 379b of each ramp 377a, 377b is a corresponding detent 374a, 374b, respectively. Stops 386a and 386b are provided adjacent a corresponding one of the detents 374a, 374b opposite the high portions 379a, 379b. A first side 387a, 387b of stops 386a, 386b is configured to prevent detents 374a, 374b from being rotated past projections 362 when clamp 352 is clamped to the cannula 20. When the lever arm 366 is manipulated to release projections 362 from the detents 374a, 374b in order to release clamp 352, the projections slide down ramps 377a, 377b to inside face 367. A back side 388a 388b of stops 386a, 386b engage the projections to limit further rotation of the lever arm 366.

In the embodiment of FIG. 33, the detents 374 are spaced at 90 degrees about the cam 364. Thus, the lever arm 366 moves through an angle of about 90 degrees to move the projections 362 from a detent 374 adjacent to a lower portion of the ramp to a detent 374 adjacent an upper portion of the ramp. In the embodiment of FIG. 34, the detents 374 are spaced at 180 degrees, but the inclined ramps 377a and 377b terminate upon turning through an arc of about 90 degrees. Preferably, when clamp ring 352 is engaged to cannula 20, lever arm 366 extends perpendicular to cannula 20 and is positioned adjacent the clamp ring 352, as illustrated in FIG. 32. This minimizes the profile of clamp assembly 350 and any interference that could be caused by lever arm 366 with the surgeon's manipulation of tools and performance of surgical procedures. In one embodiment, the lever arm is rotated 90 degrees to be parallel to the cannula in order to release clamp 352 to reposition or remove the clamp assembly 350. In another embodiment, the clamp 352 is released when the lever arm 366 is rotated in the range of about 45 degrees to about 135 degrees from its clamped position perpendicular to the axis of the cannula 20.

Referring now to FIG. 35, another embodiment of a clamping assembly of the present invention is illustrated and designated at 400. Clamping assembly 400 has a ring that includes a pair of clamping arms 402 and 404. Arms 402 and 404 are pivotably coupled with one another via clamping mechanism 401. Clamping mechanism 401 includes a pair of lever 408 and 410 coupled to hinge portion 406. Levers 408 and 410 and hinge 406 are coupled to arms 402 and 404, and allowing the arms 402, 404 to be selectively engaged to the outer surface 23 of cannula 20. Clamp mechanism 400 further includes a viewing element receiving portion 412 extending from and integrally formed with one the clamping arms (shown in FIG. 35 connected to arm 402). Receiving portion 412 is similarly configured to function like viewing element receiving portion 390, as illustrated and described with respect to FIGS. 28–29, with like elements being indicated by like reference numerals. Lever arm 402 defines a cannula engaging surface 416, and lever arm 404 defines a cannula engaging surface 418. Free end 403 of lever arm 492 and free end 405 of lever arm 404 define a slot or gap 419 therebetween. The size of gap 419 is not critical, so long as arms 402, 404 are operable to selectively grip the cannula 20.

Arms 402 and 404 are biased by a spring (not shown) coupled to hinge 406 so that clamping surfaces 416, 418 provide a gripping force against outer surface 23 of cannula 20. In order to rotate, translate, or remove the clamping mechanism with respect to the cannula 20, lever arms 408, 410 are pressed towards one another (as indicated by the arrows 408a, 410a in FIG. 35) to separate first ends 403 and 405. The grip of clamping surfaces 416, 418 is then released from outer surface 23, and the mechanism 400 may be moved along the length of the cannula 20 or removed from the cannula 20 according to the need of the surgeon.

It is contemplated that hinge 406 may be any type of hinge suitable for clamping clamp mechanism 400 to cannula 20 as would occur to those skilled in the art. For example, hinge 406 may includes a pin extending through colinear bores defined by the clamping arms 402, 404, with a spring biasing arms 402, 404 to their clamping position.

It should be understoood that clamp assemblies 350 and 400 each allow rotation and translation of optics 190 similarly as described above with respect to fixture 170.

In accordance with one specific embodiment of the invention, portions of viewing element 310 and the components of the clamp assemblies 350 and 400 are formed of a flexible and resilient material. For example, the body portion 316 and receiving portion 390 can be formed of a plastic, such as polycarbonate, and are particularly well-suited to typical plastic molding techniques. Likewise, the lever arm 366 and can be molded from a plastic material. In one specific embodiment, these components are formed of Delrin®, since Delrin® provides a smooth surface for the relative movement between the projections 362 on the clamping arm 354b and the cam faces 364, 364' of lever arm 366.

It is understood that the travel of the barrel clamping mechanism 360 and biasing force of mechanism 401 can be calibrated so as to tightly compress the clamping ring 352 and arms 402, 404 respectively, about the cannula 20. It is also understood that this compression must not be so great as to compromise the integrity or strength of the cannula 20. In one specific embodiment, the slot 358 is larger than the maximum travel of the barrel clamp mechanism 360 along inclined ramps 377 so that the projections 362 can rest solidly within the detents 374 of the lever arm 366. In accordance with one specific embodiment, the slot 358 has a dimension of 2.0 mm while the throw of the barrel clamp mechanism 360 achieved by the cam 364 is 1.0 mm.

From the foregoing description of the embodiments of the present invention illustrated in FIGS. 27–36, several advantages and methods of using the present invention should be understood. The detachability of the viewing element 310 from the clamp assemblies 350 or 400 allows multiple uses of a single viewing element 310. The same viewing element 310 may also be used with clamp assemblies manufactured for different sized and shaped cannulas. Since a single viewing element 310 may be used for multiple sized cannulas and clamp assemblies, the unit cost per procedure is reduced. Also, it is cost-effective to manufacture the viewing element and its components from high-quality materials. For example, optics cannula 320 may be made from stainless steel. High quality materials for optical components often enable the use of smaller-sized components, thus conserving additional area in the working channel of the cannula for surgical working space. In one specific embodiment, optics cannula 320 has a diameter of about 3 mm. Optimum picture quality may also be obtained by use of glass components in the viewing element.

Referring now to FIGS. 36–37, alternate embodiments of cross-sections for the cannula 20 are illustrated. The cannula 20 has been illustrated with having a generally circular cross-section. It is also contemplated that the cannula 20 have non-circular cross-sections. For example, FIG. 36 cannula 430 has an outer surface 432 that defines an oval cross-section. In FIG. 37, the cannula 440 has an outer surface 442 that defines a square cross-section. Of course, it should be understood that corresponding adjustments in the design and configuration of the fixtures and clamping assemblies described herein are also required in order to engage the outer surface of the cannulas illustrated in FIGS. 36–37. In one embodiment, the cannula 20 of the present invention has a variable cross section profile along at least a portion of its length between proximal end 22 and distal end 21. The variable profile provides a larger cross-sectional dimension and/or area at the proximal end 22 than at the distal working end 21. In one form, the variable profile defines a frusto-conical portion along longitudinal axis L of the cannula 20.

Figure 39:
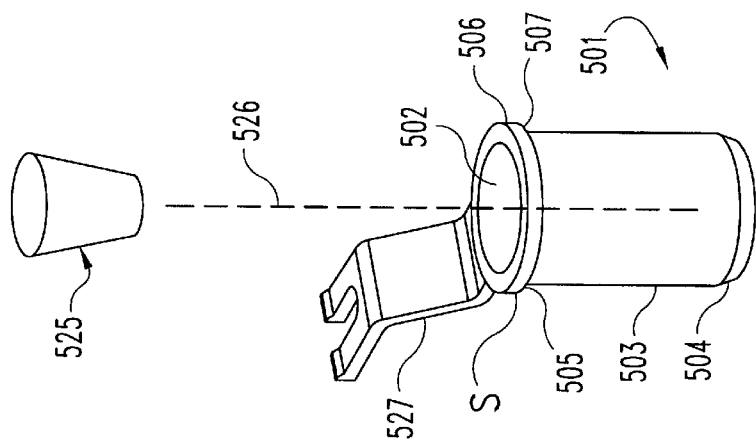
FIG. 39 is a perspective view of a cannula comprising a portion of the device of FIG. 38.
Figure 38:
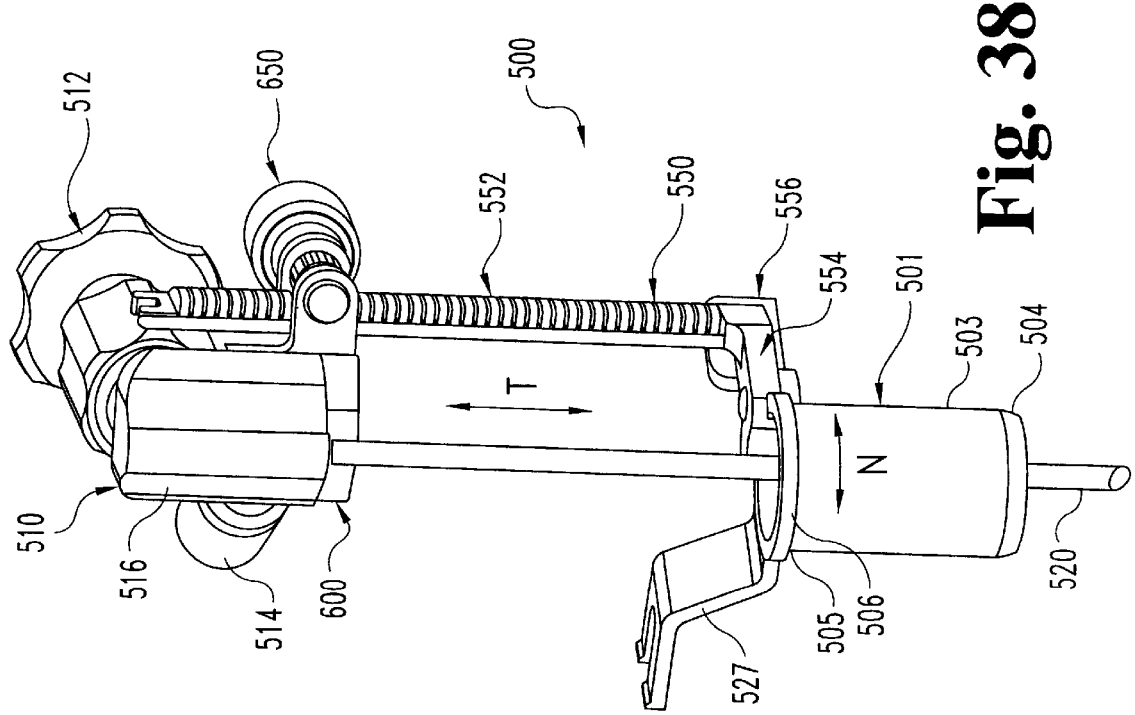
FIG. 38 is a perspective view of a device according to a further embodiment of the present invention.

Referring now to FIGS. 38–48, a device 500 for performing percutaneous surgery is provided according to another embodiment of the present invention. As shown in FIG. 38, device 500 includes a clamp assembly 550 for supporting a viewing element 510 on a tubular retractor or cannula 501. Though not illustrated in FIG. 38, viewing element 510 can be provided with or without irrigation/aspiration components as discussed above with respect to device 300. Clamp assembly 550 is engaged on a proximal end 505 of cannula 501, and can preferably be easily removed from cannula 501 or moved about cannula 501 by the surgeon during surgery to reposition viewing element 510 relative to cannula 501. Since clamp assembly 550 is mounted on the proximal end of cannula 501, cannula 501 can have a length sized to position proximal end 505 at or just slightly above skin level S, as shown in FIG. 39, when distal end 504 is at the desired location in the patient.

As further shown in FIG. 39, cannula 501 has a working channel 502 that extends between a distal end 504 and proximal end 505. Cannula 501 can have any cross-sectional shape as discussed above, including oval, elliptical, or circular cross-sectional shapes, for example. Distal end 504 can be beveled to facilitate percutaneous insertion of cannula 501 as discussed above with respect to cannula 20. A ring 506 is provided around the proximal end 505 of cannula 501 to enlarge proximal end 505. Preferably, ring 506 has an outer diameter that is slightly larger than the diameter at outer surface 503 of cannula 501 such that a lower lip 507 is formed around outer surface 503 by ring 506. A bracket 527 extends outwardly from proximal end 505 and is provided for attachment of a flexible arm thereto to secure cannula 501 to a surgical table such as discussed above.

Referring back to FIG. 38, viewing element 510 includes a viewing port 512 and an illumination element 514 coupled to a body portion 516. Viewing element 510 further includes an optics cannula 520 as discussed above with respect to optics cannula 190 and 320. Body portion 516 defines an optics bore (not shown) for receiving and supporting optics cannula 520, and to provide visual communication between optics cannula 520 and viewing portion 512. The components of viewing portion 512 can include an eyepiece component and focus adjustment knob, which can be integrally formed with the body portion 516 or threadingly coupled thereto.

With viewing element 510 supported by clamp assembly 550, and clamp assembly 550 engaged to cannula 501, optics cannula 520 extends from body portion 516 and at least partially into working channel 502 of cannula 501. As will be discussed further below, clamp assembly 550 can be moved about cannula 501, and can also be engaged/disengaged from cannula 501 when cannula 501 is positioned in the patient. A microscope 525, as shown in FIG. 39, can be positioned over working channel 502 in order to view the working space at the distal end of cannula 501 along viewing axis 526. Preferably, clamp assembly 550 and viewing element 510 are removed when using microscope 525 to increase the field of view and provide additional room for surgical instruments to be used through cannula 501. The present invention gives the surgeon flexibility in selecting the desired viewing system, whether it be endoscopic or microscopic, and to efficiently alternate between viewing systems during the surgical procedure.

In one specific embodiment, it is contemplated that cannula 501 can be provided in lengths ranging from 30 millimeters to 90 millimeters, preferably in increments of 10 millimeters. It is contemplated that cannula 501 can have a diameter of 14, 16, 18 or 20 millimeters. It should be understood, however, that the present invention contemplates that cannula 501 can have other lengths and diameters. The appropriate length for cannula 501 will depend on the depth of the desired location for distal end 504 below the skin S of the patient in order to complete the surgical procedure, the anatomical location of the surgery, and the patient's anatomy. These factors in cannula selection can be evaluated through pre-operative planning prior to surgery by x-rays or other know imaging technique, and can be adjusted during the surgical procedure if necessary since cannulas of differing lengths and diameters can be made available.

Referring now to FIGS. 40 through 48, further details of clamp assembly 550 will now be described. Clamp assembly 550 includes a generally vertical viewing element mounting portion 552 and a foot 554 extending therefrom and oriented generally orthogonally therewith. Foot 554 has a channel 560 sized to receive ring 506 of cannula 501 when foot 554 is placed over proximal end 505 of cannula 501. Preferably channel 560 has a curved inner lip 562 positionable along the inside surface of cannula 501 and a curved outer lip 563 positionable along the outer surface of ring 506. Inner lip 562 preferably has a concave profile to match the profile of the inner surface of cannula 501 to minimize its protrusion into working channel 502. It is further contemplated that the radius of curvature of one or both inner lip 562 and outer lip 563 can substantially differ from the radius of curvature of the adjacent cannula wall surface so that channel 560 of the same clamp assembly 550 can be used with cannulas of differing diameters. For example, inner lip 562 can have a radius of curvature that corresponds approximately to the radius of curvature of the inner surface of a first cannula that has a cannula diameter of 14 millimeters. Outer lip 563 can have a radius of curvature sized to approximately correspond to the radius of curvature of ring 506 of a second cannula that has a cannula diameter of 18 millimeters. This allows the same clamp assembly 550 to be used for cannulas having diameters in the range of 14 millimeters to 18 millimeters.

Figure 46:
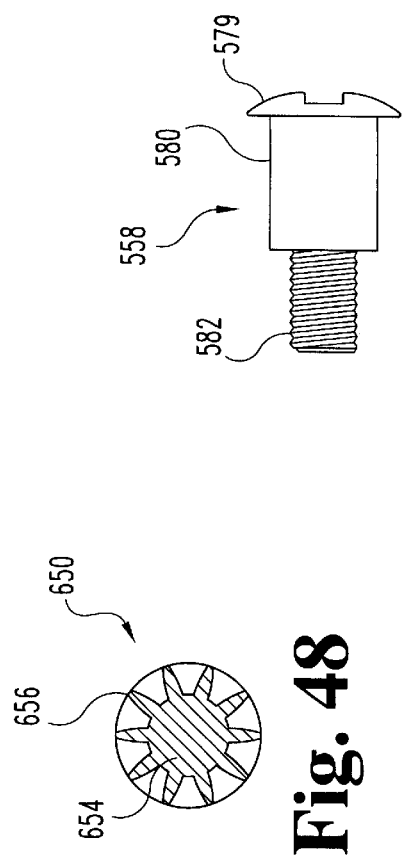
FIG. 46 is an elevational view of a fastener for securing the lever arm of FIG. 44 to the clamp assembly of FIG. 40.

Foot 554 has a lever arm 556 pivotally engaged thereto via fastener 558. Lever arm 556 has a handle 566 and a cam or clamping member 564 integrally formed with and extending from handle 566. As further shown in FIGS. 44 and 45, clamping member 564 has a cam or clamping surface 568 positionable against outer surface 503 of cannula 501 when foot 554 is placed on ring 506 of cannula 501. Clamping member 564 includes a threaded hole 574 extending therethrough engaged by fastener 558. As shown in FIG. 46, fastener 558 has a head 579 with a tool engaging recess, a non-threaded portion 580 adjacent head 579, and a distal threaded portion 582. Non-threaded portion 580 extends through and is freely rotatable in foot 554, while threaded portion 582 pivotably attaches lever arm 556 to foot 554.

Figure 40:
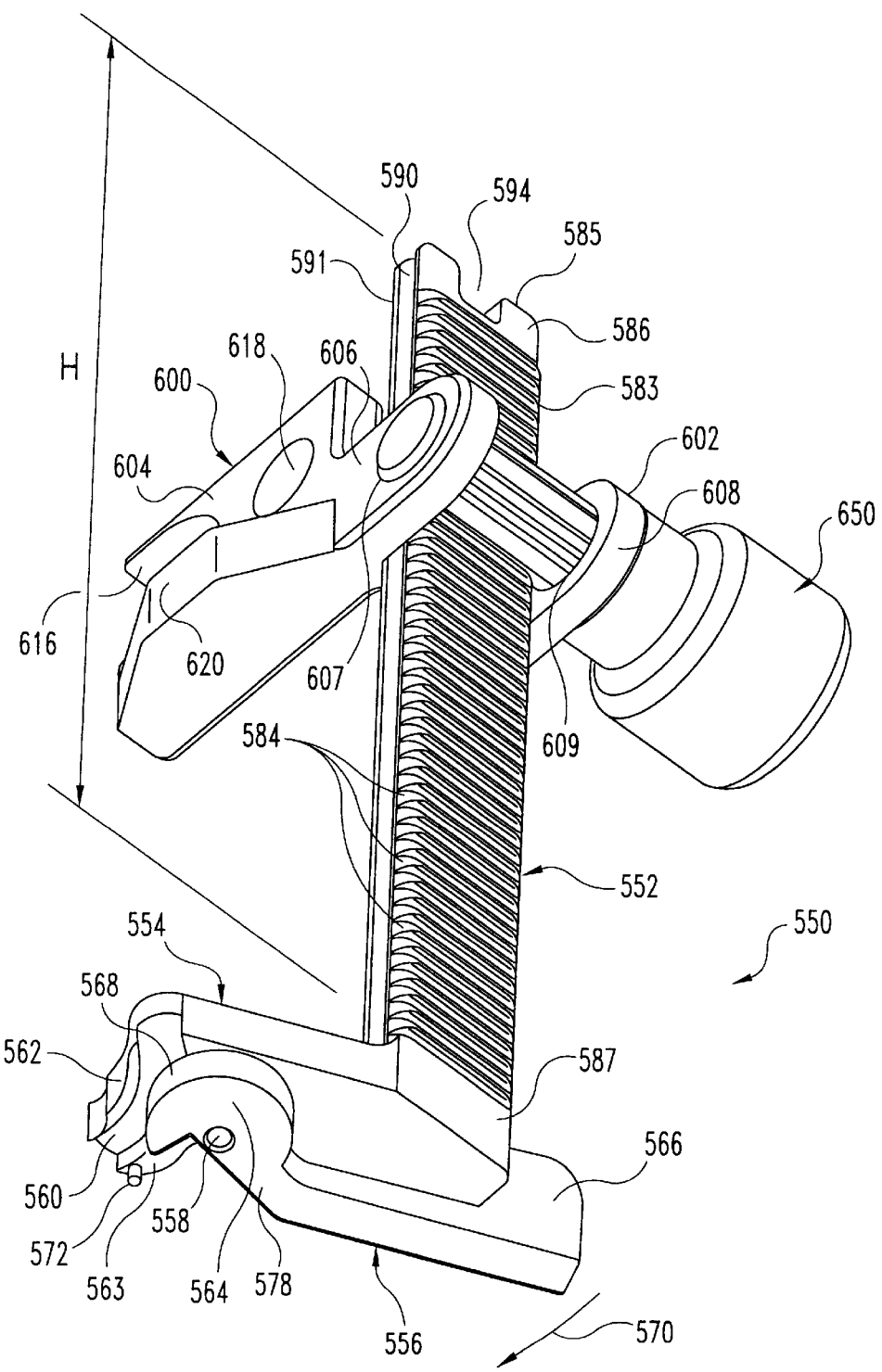
FIG. 40 is a perspective view looking up at a clamp assembly comprising a portion of the device of FIG. 38 detached from the cannula of FIG. 39.
Figure 41:
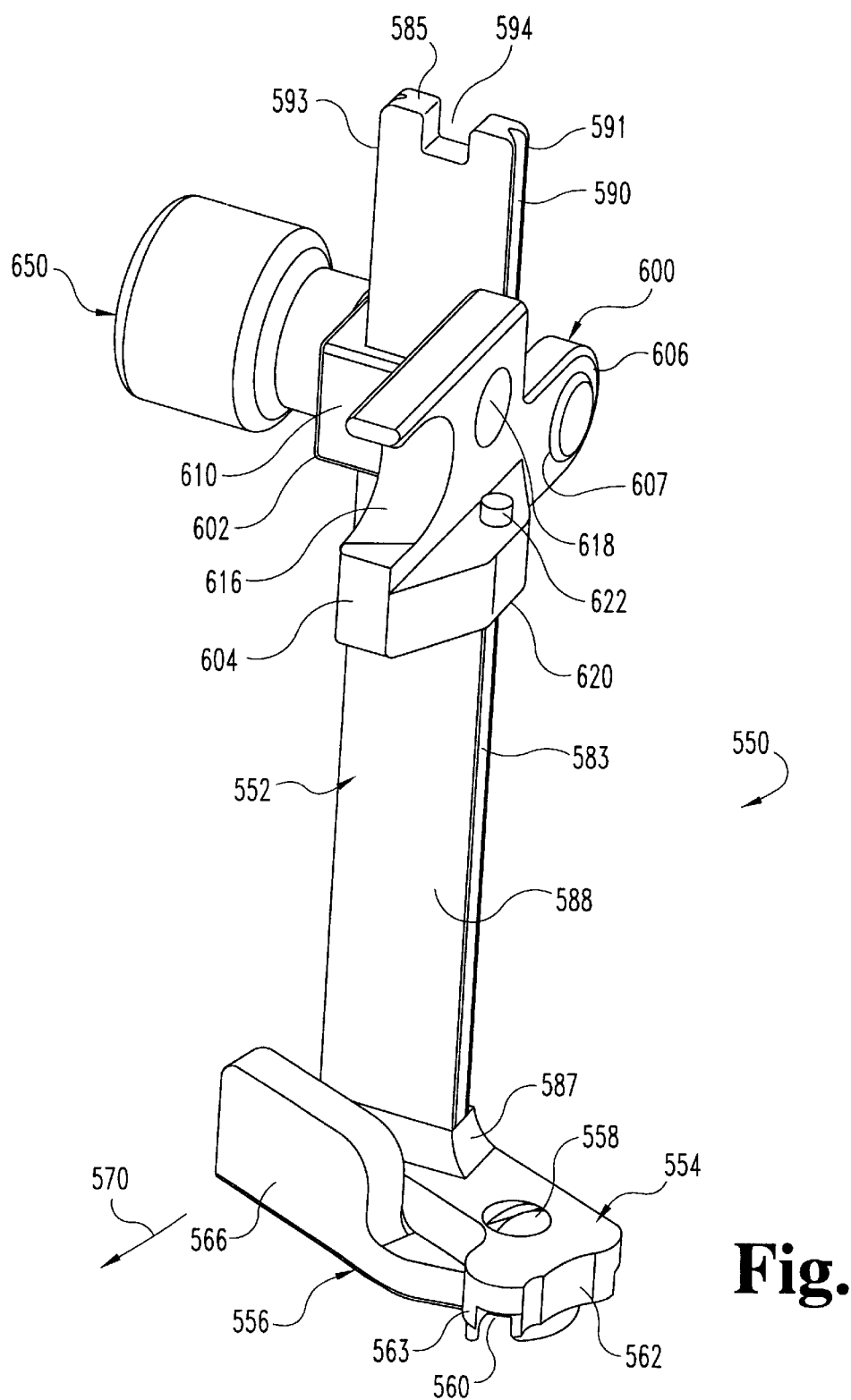
FIG. 41 is another perspective view looking down at the clamp assembly rotated about 90 degrees around its central vertical axis from its position of FIG. 40.
Figure 42:
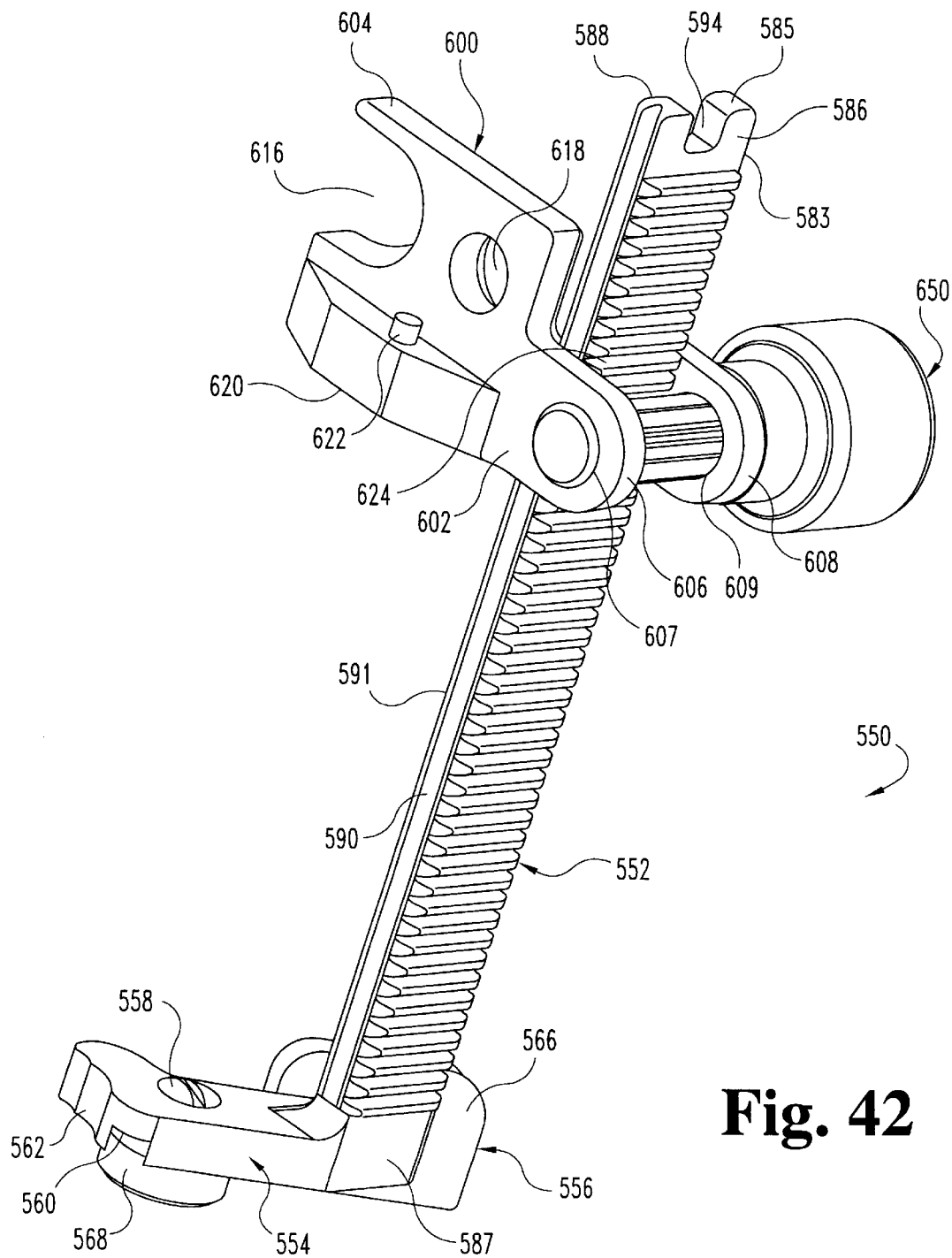
FIG. 42 is a perspective view looking down at the clamp assembly with the clamp assembly having generally the same orientation about its central vertical axis as in FIG. 40.

Lever arm 556 includes an offset 578 that positions clamping member 564 below foot 554 while allowing handle 566 to extend alongside foot 554 and mounting portion 552 when lever arm 556 is in its engaged position (FIG. 40.) Offset 578 further enables lever arm 556 to be rotated in the direction of arrow 570 a sufficient distance and positioned alongside cannula 501 so that there is no interference or contact between clamping member 564 and lip 507, facilitating removal of clamping assembly 550 from cannula 501. Clamping member 564 further has an angled lead-in in the form of ramped surface 576 formed on upper surface 575. Ramped surface 576 facilitates passage of clamping member 564 below ring 506 until upper surface 575 contacts lip 507 to engage clamp assembly 550 to ring 506.

To secure clamp assembly 550 to cannula 501, channel 560 is positioned on ring 506 with inner lip 562 positioned along the inner surface of cannula 501 and outer lip 563 positioned along the outer surface of ring 506. Channel 560 preferably has a depth sufficient to accommodate the height of ring 506 so that upper surface 575 of lever arm 556 is positioned below ring 506. When lever arm 556 is in the engaged position shown in FIG. 40, clamping surface 568 contacts outer surface 503 of cannula 501 and upper surface 575 contacts lip 507. Frictional engagement between outer surface 503 and the engagement with ring 506 secures clamp assembly 550 to cannula 501. In this engaged positioned, handle 566 is positioned adjacent to foot 554, with foot 554 limiting the range of movement of lever arm 556 in the direction opposite arrow 570. It is understood that the dimensional relationship between foot 554, lever arm 556 and cannula 501 can be established so clamping assembly 550 can be immovably engaged to cannula 501. It is also understood that compression forces applied by clamp assembly 550 are not so great as to compromise the integrity or strength of cannula 501.

To disengage clamp assembly 550 from cannula 501, lever arm 556 is moved in the direction of arrow 570 until clamping surface 568 no longer contacts outer surface 503 and clamping member 564 is no longer below lip 507, allowing clamp assembly 550 to be lifted off of cannula 501. A stop member 572 extending downwardly from foot 554 limits rotation of lever arm 556 in the direction of arrow 570. Lever arm 556 can also be rotated in the direction of arrow 570 to disengage clamping surface 568 from cannula 501 without removal of clamp assembly 550 from cannula 501. This allows viewing element 510 to be rotated about the perimeter of the proximal end of cannula 501 in the directions indicated by arrow N of FIG. 38 in order to position the lens at the desired location in working channel 502 with respect to the surgical site.

Additionally, viewing element 510 can be translated along the length of the viewing element mounting portion 552 in the direction of the arrow T in order to position the lens at the desired location with respect to distal end 504 and the surgical site. Viewing element mounting portion 552 includes an elongated body 583 extending between a top end 585 and a bottom end 587. Body 583 is integrally formed with or fixedly attached to foot 554 at bottom end 587 and extends upwardly therefrom to a top end 585. The length of travel of viewing element 510 in the direction of arrow T along mounting portion 552 is limited by height H (FIG. 40.) In one specific embodiment, height H is in the range of 69 to 73 millimeters. It is further contemplated that other embodiments can have heights greater than 73 millimeters or less than 69 millimeters. Preferably, height H is sufficient to position body portion 516 away from the proximal end opening of cannula 501 to provide room for the insertion and manipulation of surgical instruments in working channel 502.

Body 583 includes a first side surface 586 and an opposite second side surface 588. A number of V-shaped grooves 584 are formed in body 583 along first side surface 586 and along height H. Mounting portion 552 further includes a first track 590 along a first end surface 591 and a second track 592 along a second end surface 593. First and second tracks 590, 592 have a V-shape in the illustrated embodiment; however other shapes are also contemplated. A notch 594 is formed in body 583 at top end 585.

Viewing element 510 is mounted to clamp assembly 550 by a bracket assembly 600 and a roller 650. Bracket assembly 600 includes a U-shaped connector 602 positionable around viewing element mounting portion 552, and a viewing element support member 604 extending from connector 602. Connector 602 further includes an end wall 610 extending between a first arm 606 and a second arm 608. First arm 606 includes a first hole 607 formed therethrough, and second arm 608 includes a second hole 609 formed therethrough. Body portion 583 is positioned between arms 606, 608 and adjacent end wall 610, and roller 650 is rotatably mounted in holes 607, 609 and in contact with grooves 584 along first side surface 586. Connector 602 has a first nub 624 extending from first arm 606 that is preferably V-shaped and positionable in first track 590. Connector 602 also includes a second nub 626 extending from second arm 608 that is also preferably V-shaped and positionable in second track 592. Nubs 624, 626 maintains alignment of connector 602 with body 583 as it is moved therealong.

Figure 43:
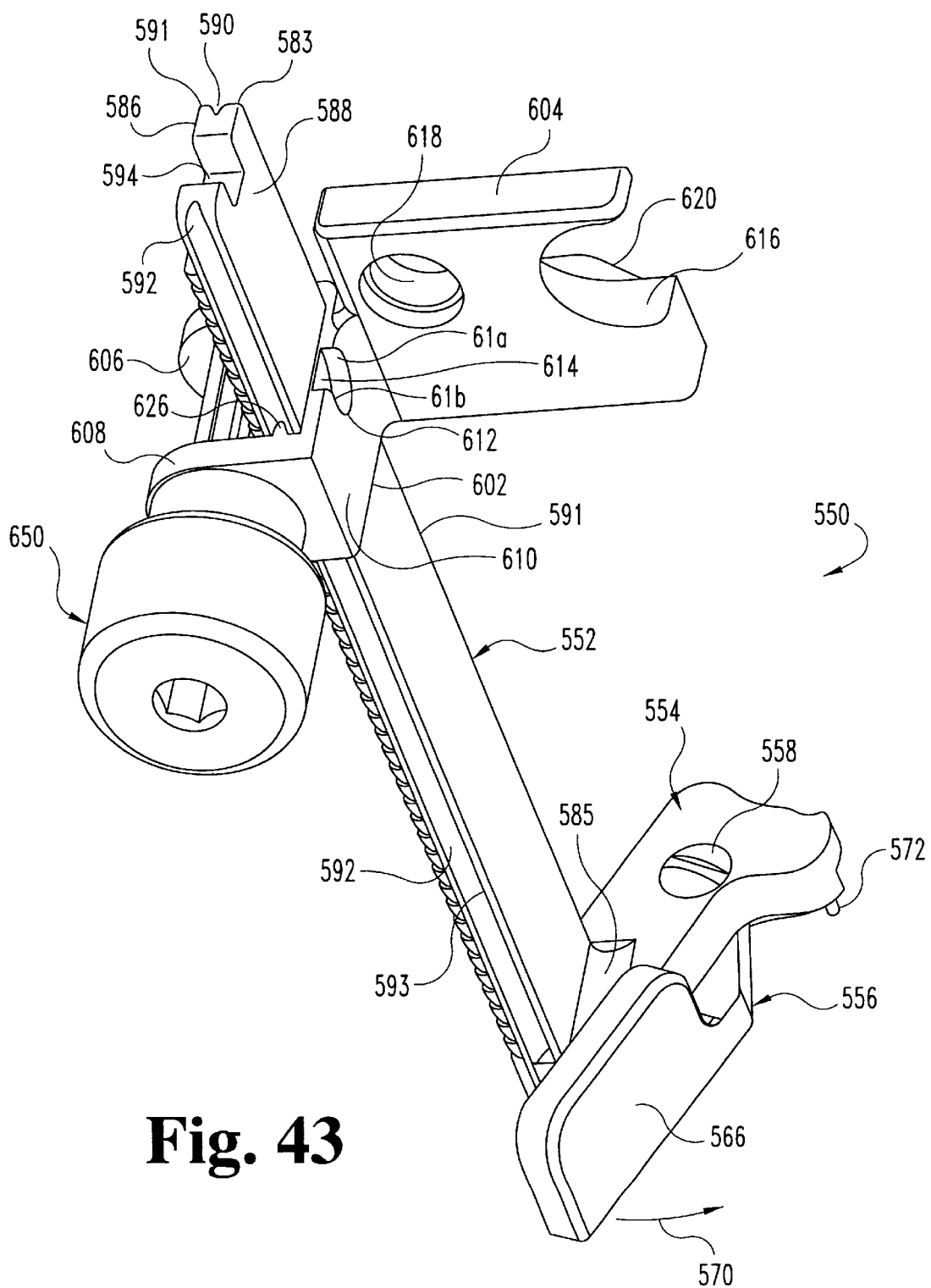
FIG. 43 is another perspective view looking down at the clamp assembly rotated about 180 degrees around its central vertical axis from its position of FIG. 40.

In order to maintain firm contact between roller 650 and grooves 584, connector 602 includes a biasing member 614 that keeps body 583 in firm contact with roller 650. As shown in FIG. 43, biasing member 614 is formed at a reduced thickness portion 612 in endwall 610. Biasing member 614 is connected to end wall 610 only along the bottom U-shaped portion, and its upper ends 614a and 614b are not connected with end wall 610. Ends 614a, 614b can be bent or pushed away from end wall 610 to apply a biasing force against second side 588 of body 583 to keep roller 650 engaged in grooves 684 and to prevent bracket assembly 600 from free-falling along body 583. Other forms for biasing member 614 are also contemplated, such as a spring biased plunger. Notch 594 provided at the top end of body 583 to facilitate assembly of bracket assembly 600 to viewing element mounting portion 552. Notch 594 receives biasing member 614 to allow roller 650 to engage in one of the upper-most grooves 584 before biasing member 614 contacts body 583 when bracket assembly 600 is top-loaded onto body 583.

Figure 47:
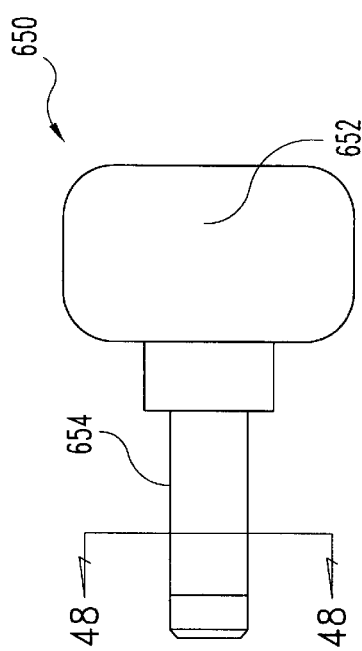
FIG. 47 is an elevational view of a roller pin for moving a viewing element along a portion of the clamp assembly of FIG. 40.
Figure 48:
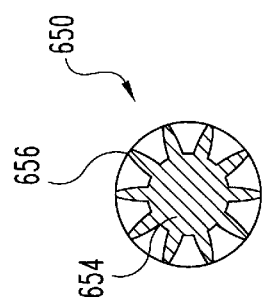
FIG. 48 is a section view taken through line 48—48 of FIG. 47.
Figure 44:
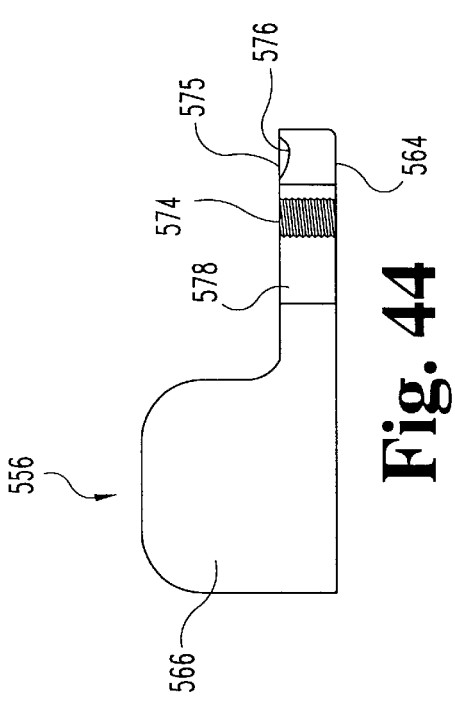
FIG. 44 is side elevational view of a lever arm comprising a portion the clamp assembly of FIG. 40.
Figure 45:
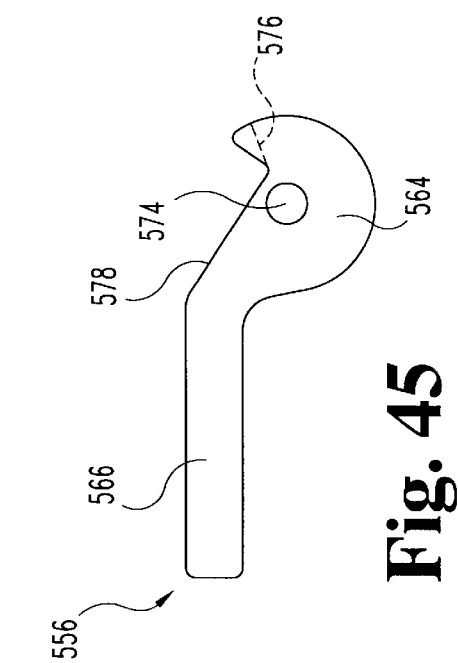
FIG. 45 is a bottom plan view of the lever arm of FIG. 44.

As shown in FIGS. 47 and 48, roller 650 includes a thumb paddle 652 and a wheel 654. Roller 650 is rotatably mounted in the holes 607, 609 formed in the arms 606, 608, respectively, of connector 602. Wheel 654 includes a number of teeth 656 that are V-shaped to fit in the V-shaped grooves 584 formed along body 583 of viewing element mounting portion 552. Teeth 656 engage respective ones of the grooves 584 as roller 650 is rotated by hand via thumb paddle 652 to move bracket assembly 600 and thus viewing element 510 in the directions of arrow T along mounting portion 552.

Viewing element support member 604 includes an illumination element slot 616 angled therethrough to receive the correspondingly angled illumination element 514. Support member 604 further includes a hole 618 for receiving a fastener (not shown) engageable to a hole (not shown) in body portion 516 of viewing element 510, securing viewing element 510 to support member 604. Support member 604 further includes a support ledge 620 extending along a bottom portion thereof. A pin 622 extends upwardly from ledge 620. Viewing element 510 includes a hole (not shown) positionable on pin 622 to resist lateral movement of viewing element 510 with respect to support member 604 while support ledge helps support the weight of viewing element 510.

In accordance with one specific embodiment of the invention, the components of the clamp assembly 550 are made from stainless steel using fabrication techniques known in the art. In another form, it is contemplated that the components of clamp assembly 550 can be formed from plastic material using fabrication techniques known in the art.

Figure 49:
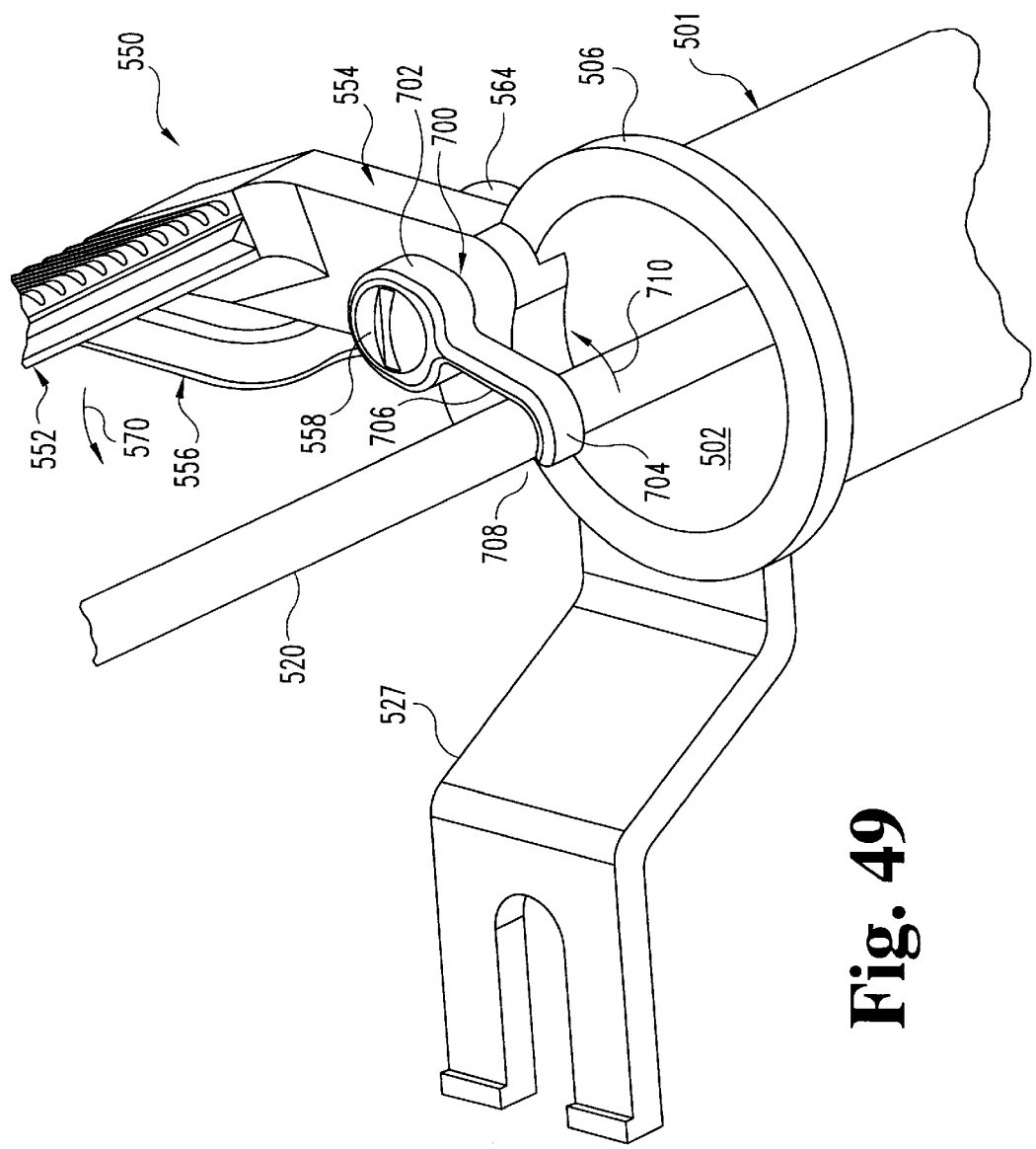
FIG. 49 is a perspective of the device of FIG. 38 according to another embodiment of the present invention.

Referring now to FIGS. 49 and 50, another embodiment of the device 500 is show is shown that includes a viewing element holder 700 mounted on foot 554 of clamp assembly 550. Viewing element holder 700 includes an eyelet 702 and a hook member 704 extending therefrom. Hook member 704 has an arcuate inner surface 706 extending along an inner side thereof and a side opening 708 sized to receive optics cannula 520. Fastener 558 extends through eyelet 702 to couple viewing element holder 700 to foot 554 and lever arm 556. Viewing element holder 700 can be keyed or otherwise interconnected with lever arm 556 to move therewith. When lever arm 556 is in its engaged position as shown in FIG. 49, hook member 704 extends around optics cannula 520 with arcuate surface 706 in contact with optics cannula 520. When lever arm 556 is moved to its unengaged position and pivoted around fastener 558 in the direction of arrow 570, viewing element holder 700 also pivots around fastener 558 in the direction of arrow 710 to displace hook member 704 from around optics cannula 520. Viewing element holder 700 can be moved to its disengaged position to facilitate assembly and disassembly of viewing element 510 from clamp assembly 550.

When in its engaged position, viewing element holder 700 resists lateral movement of optics cannula 520 and maintains its position along the inner sidewall of cannula 501 when optics cannula 520 is contacted by, for example, a surgical instrument. Such movement could interfere with the surgeon's viewing of the surgical site through the viewing element 510. It is preferred that the holding force exerted by hook member 704 is not so great as to prevent extension and retraction of viewing element 510 with roller 650 when viewing element holder 700 is in its engaged position.

From the foregoing description of the embodiments of the present invention illustrated in FIGS. 38–50, several advantages and methods of using the present invention should be understood. The detachability of the viewing element 510 and clamp assembly 550 allows cannula 501 to be used by the surgeon with a microscope or an endoscope. For example, according to one preferred technique of the present invention, a microscope can be used during sequential dilation of the tissue and insertion of cannula 501 to provide working channel access to the surgical site. A microscope can continued to be used for visualization while instruments are inserted through cannula 501 to perform surgical procedures in the working space at the distal end of cannula 501. However, viewing with the microscope can be obstructed by one or more instruments that are inserted into the working channel of cannula 501, or when viewing deep within the patient's body is desired. An endoscopic viewing element, such as viewing element 510, can be mounted to cannula 501 with clamp assembly 550. Viewing obstructions are then eliminated or minimized since viewing element 510 has optics cannula 520 that places the viewing lens adjacent the surgical site. Viewing of the surgical site can be further enhanced by the rotational and translational positioning capability of the endoscope provided by clamp assembly 550.

Further advantages are realized since the same clamp assembly 550 and viewing element 510 may be used with cannulas of differing diameters. Since a single viewing element 510 may be used for multiple sized cannulas, the unit cost per procedure is reduced. Also, it is cost-effective to manufacture the viewing element and its components from high-quality materials. For example, optics cannula 520 may be made from stainless steel. High quality materials for optical components often enable the use of smaller-sized components, thus conserving additional area in the working channel of the cannula for surgical working space. In one specific embodiment, optics cannula 520 has a diameter of about 5 millimeters. Optimum picture quality may also be obtained by use of glass components in the viewing element.

Additional advantages are realized since cannula 501 need not extend beyond the skin level of the patient in order to engage clamp assembly 550 thereto. The shorter length cannula allows greater angulation of instruments that are inserted through the working channel, reducing the diameter required for the cannula and/or increasing the reach of the instruments into the working space beyond the walls of the cannula at its distal end.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. A device for use in spinal surgery, comprising:
   a cannula sized for introduction into a patient, said cannula defining a working channel extending between a distal end and an opposite proximal end, said cannula further defining a first length between said distal end and said proximal end;
   a clamp assembly configured to apply a clamping force to said inner surface and said outer surface of said cannula to releasably engage said clamp assembly thereto, said clamp assembly including a viewing element mounting portion extending proximally from said cannula and having a second length; and a viewing element engageable at various positions along said second length of said viewing element mounting portion.

2. The device of claim 1, wherein said viewing element mounting portion includes a body along said second length, said body having a plurality of grooves formed in a first side thereof.

3. The device of claim 2, wherein said clamp assembly includes a bracket assembly movably mounted to said viewing element mounting portion, said viewing element being attached to said bracket assembly.

4. The device of claim 3, wherein said bracket assembly has a connector and a roller rotatably mounted to said connector, said body being positioned between said connector and said roller with said roller engaged with at least one of said plurality of grooves in said body.

5. The device of claim 4, wherein said bracket assembly further includes a support member extending from said connector, said viewing element being attached to said support member.

6. The device of claim 5, wherein said support member includes a ledge along a bottom portion thereof upon which said viewing element sits.

7. The device of claim 6, wherein said support member has a hole therethrough for receiving a fastener and said ledge includes a pin extending upwardly therefrom, said fastener and said pin engageable to said viewing element to secure said viewing element to said bracket assembly.

8. The device of claim 4, wherein said roller includes a number of teeth formed thereabout having a V-shape, each of said plurality of grooves having a V-shape and sized to receive said teeth.

9. The device of claim 1, wherein said clamp assembly contacts an inner surface and an outer surface of said cannula when engaged thereto.

10. The device of claim 1, wherein said cannula has a circular cross-section.

11. The device of claim 1, wherein said viewing element includes an endoscope positionable in said working channel of said cannula when said viewing element is engaged to said viewing element mounting portion.

12. The device of claim 1, wherein said clamp assembly comprises:
a foot extending from said viewing element mounting portion, said foot having a channel positionable over the proximal end of said cannula; and
a lever arm pivotably attached to said foot, said lever arm having a handle and a clamping member, said clamping member having a clamping surface frictionally engageable to an outer surface of said cannula.

13. The device of claim 12, wherein said cannula has a ring member at said proximal end defining a lip around said outer surface of said cannula, said channel of said foot being positionable on said ring and said clamping member having an upper surface positionable against said lip when said clamp assembly is engaged to said cannula.

14. The device of claim 13, wherein upper surface of said clamping member has a ramped portion facilitating passage of said clamping member below said lip.

15. The device of claim 1, wherein said cannula includes a bracket extending from a proximal end thereof engageable to a flexible arm.

16. A device for supporting a viewing element during surgery in a patient, comprising:
a cannula having a length extending between a proximal end and a distal end, said cannula further having an outer surface and an inner surface defining a working channel extending between said proximal end and said distal end; and
a clamp assembly configured to apply a clamping force to said inner surface and said outer surface of said cannula to releasably engage said clamp assembly thereto, said clamp assembly including a viewing element mounting portion extending proximally from said cannula.

17. The device of claim 16, wherein said clamp assembly comprises:
a foot extending from said viewing element mounting portion, said foot having a channel positionable over the proximal end of said cannula; and
a lever arm pivotably attached to said foot, said lever arm having a clamping member with a clamping surface frictionally engageable to an outer surface of said cannula.

18. The device of claim 17, wherein said foot includes:
an inner lip along one side of said channel positionable adjacent said inner surface of said cannula; and
an outer lip along the opposite side of said channel positionable adjacent said outer surface of said cannula,
wherein one of said inner lip and said outer lip have a radius of curvature that substantially differs from the radius of curvature of the adjacent surface of said cannula.

19. The device of claim 17, wherein said cannula has a ring member at said proximal end defining a lip around said outer surface, said ring being positionable in said channel and said clamping member having an upper surface positionable against said lip when said clamp assembly is engaged to said cannula.

20. The device of claim 19, wherein said upper surface of said clamping member has a ramped portion facilitating passage of said clamping member under said lip.

21. A kit for use in percutaneous surgery, comprising:
an elongated cannula sized for introduction into a patient, said cannula defining a working channel and having a longitudinal axis extending between a distal end and a proximal end, said cannula further defining a length between said distal end and said proximal end;
a clamp assembly engageable to said proximal end of said cannula, wherein said clamp assembly is configured to apply a clamping force to an inner surface and an outer surface of said cannula to engage said clamp assembly thereto, said clamp assembly including a viewing element mounting portion extending proximally from said cannula;
a viewing element supported by said clamp assembly, said viewing element having an optics cannula positionable in said working channel; and
a microscope positionable over said proximal end of said cannula.

22. The device of claim 21, wherein said clamp assembly is engageable at a plurality of locations about the proximal end of said cannula to reposition said optics cannula in said working channel.

23. The device of claim 21, wherein said clamp assembly includes a viewing element mounting portion extending proximally from said cannula when said clamp assembly is engaged to said cannula, said viewing element being engageable at various positions along the length of said viewing element mounting portion to reposition a distal end of said optics cannula with respect to said distal end of said cannula.

24. A kit for use in percutaneous surgery, comprising:
an elongated cannula sized for introduction into a patient, said cannula defining a working channel and having a longitudinal axis extending between a distal end and a proximal end, said cannula further defining a length between said distal end and said proximal end;
a clamp assembly engageable to said cannula, wherein said clamp assembly is engageable at a plurality of locations about the proximal end of said cannula to reposition said optics cannula in said working channel;
a viewing element supported by said clamp assembly, said viewing element having an optics cannula positionable in said working channel; and
a microscope positionable over said proximal end of said cannula.

25. The device of claim 24, wherein said clamp assembly is engaged to said proximal end of said cannula.

26. The device of claim 24, wherein said clamp assembly is configured to apply a clamping force to an inner surface and an outer surface of said cannula to engage said clamp assembly thereto, said clamp assembly including a viewing element mounting portion extending proximally from said cannula.

27. The device of claim 24, said clamp assembly includes a viewing element mounting portion extending proximally from said cannula when said clamp assembly is engaged to said cannula, said viewing element being engageable at various positions along the length of said viewing element mounting portion to reposition a distal end of said optics cannula with respect to said distal end of said cannula.

28. A kit for use in percutaneous surgery, comprising:
an elongated cannula sized for introduction into a patient, said cannula defining a working channel and having a longitudinal axis extending between a distal end and a proximal end, said cannula further defining a length between said distal end and said proximal end;
a clamp assembly engageable to said cannula, wherein said clamp assembly includes a viewing element mounting portion extending proximally from said cannula when said clamp assembly is engaged to said cannula, said viewing element being engageable at various positions along the length of said viewing element mounting portion to reposition a distal end of said optics cannula with respect to said distal end of said cannula;
a viewing element supported by said clamp assembly, said viewing element having an optics cannula positionable in said working channel; and
a microscope positionable over said proximal end of said cannula.

29. The device of claim 28, wherein said clamp assembly is engaged to said proximal end of said cannula.

30. The device of claim 28, wherein said clamp assembly is configured to apply a clamping force to an inner surface and an outer surface of said cannula to engage said clamp assembly thereto, said clamp assembly including a viewing element mounting portion extending proximally from said cannula.

31. The device of claim 28, wherein said clamp assembly is engageable at a plurality of locations about the proximal end of said cannula to reposition said optics cannula in said working channel.

32. A method for performing a surgical procedure at a location in a patient, comprising:
inserting into the patient a cannula having a distal end and a proximal end and a working channel therebetween;
alternately employing during the same surgical procedure an endoscopic viewing system engageable to the proximal end of the cannula and a microscopic viewing system to view the location in the patient through the working channel of the cannula; and
securing a clamp assembly having an endoscopic viewing element mounted thereto to the proximal end of the cannula when employing the endoscopic viewing system.

33. The method of claim 32, further comprising:
sizing the cannula so that the proximal end of the cannula is positioned at the skin level of the patient when the distal end is positioned adjacent the location in the patient.

34. The method of claim 32, further comprising:
removing the clamp assembly before employing the microscopic viewing system.

* * * * *